(12) United States Patent
Gundluru et al.

(10) Patent No.: US 10,149,838 B2
(45) Date of Patent: Dec. 11, 2018

(54) SMALL MOLECULE SECURININE AND NORSECURININE ANALOGS AND THEIR USE IN INHIBITING MYELOPEROXIDASE

(71) Applicants: MiRx Pharmaceuticals, LLC, Lexington, KY (US); Mahesh K. Gundluru, Lexington, KY (US); Mukesh Agarwal, Solon, OH (US); Zhiqing Xia, Lexington, KY (US); Goutam Karan, Lexington, KY (US); David Wald, Shaker Heights, OH (US)

(72) Inventors: Mahesh K. Gundluru, Lexington, KY (US); Mukesh Agarwal, Solon, OH (US); Zhiqing Xia, Lexington, KY (US); Goutam Karan, Lexington, KY (US); David Wald, Shaker Heights, OH (US)

(73) Assignee: David Wald, Shaker Heights, OH (US)

( * ) Notice: Subject to any disclaimer, the term of this patent is extended or adjusted under 35 U.S.C. 154(b) by 0 days.

(21) Appl. No.: 15/026,818

(22) PCT Filed: Oct. 3, 2014

(86) PCT No.: PCT/US2014/059104
§ 371 (c)(1),
(2) Date: Apr. 1, 2016

(87) PCT Pub. No.: WO2015/051276
PCT Pub. Date: Apr. 9, 2015

(65) Prior Publication Data
US 2016/0250196 A1    Sep. 1, 2016

Related U.S. Application Data

(60) Provisional application No. 61/886,448, filed on Oct. 3, 2013, provisional application No. 61/942,880, filed on Feb. 21, 2014, provisional application No. 62/051,595, filed on Sep. 17, 2014.

(51) Int. Cl.
| | | |
|---|---|---|
| A61K 31/55 | (2006.01) | |
| A61K 31/437 | (2006.01) | |
| C07F 7/18 | (2006.01) | |
| A61K 31/439 | (2006.01) | |
| C07D 491/18 | (2006.01) | |
| A61K 31/407 | (2006.01) | |
| A61K 31/537 | (2006.01) | |
| A61K 45/06 | (2006.01) | |
| C07D 498/18 | (2006.01) | |
| A61K 31/4439 | (2006.01) | |
| A61K 31/496 | (2006.01) | |
| A61K 31/695 | (2006.01) | |
| C07D 519/00 | (2006.01) | |
| C12N 9/99 | (2006.01) | |
| A61K 31/5365 | (2006.01) | |

(52) U.S. Cl.
CPC .......... *A61K 31/437* (2013.01); *A61K 31/407* (2013.01); *A61K 31/439* (2013.01); *A61K 31/4439* (2013.01); *A61K 31/496* (2013.01); *A61K 31/537* (2013.01); *A61K 31/5365* (2013.01); *A61K 31/55* (2013.01); *A61K 31/695* (2013.01); *A61K 45/06* (2013.01); *C07D 491/18* (2013.01); *C07D 498/18* (2013.01); *C07D 519/00* (2013.01); *C07F 7/1804* (2013.01); *C07F 7/1856* (2013.01); *C12N 9/99* (2013.01)

(58) Field of Classification Search
CPC ....................................................... A61K 31/55
USPC ............................................. 514/217, 217.01
See application file for complete search history.

(56) References Cited

U.S. PATENT DOCUMENTS

2012/0122948 A1    5/2012  Soubhye et al.

OTHER PUBLICATIONS

Written Opinion and International Search Report dated Dec. 19, 2014.
Subramanian et al., Development and Commercialization of Securinine Analogue as a Therapeutic Compound for the Treatment of Acute Myeloid Leukemia, 2011, MS Thesis submitted to Case Western University. [Retrieved from: ohiolink.edu) p. 30, Fig 9; p. 31, para 2, Table 1.
Li et al. "Unexpected ring contraction and oxidation rearrangement reactions of securinine", Tetrahedron, 2012, vol. 68, pp. 3972-3979. p. 3976, Table 2, compound 10; p. 3975, scheme 4;p. 3978, col. 1, para 2-5.

*Primary Examiner* — Kevin E Weddington
(74) *Attorney, Agent, or Firm* — King & Schickli, PLLC

(57) ABSTRACT

The present invention relates to use of novel securinine and norsecurine analogs to bind and/or inhibit myeloperoxidase activity.

9 Claims, 8 Drawing Sheets

Table 1: IC$_{50}$ value on cell culture

| Compound | HEK293 (µM) | BJ1 (µM) | MEF (µM) |
|---|---|---|---|
| MA1 | 10.3 | 15.2 | 13.2 |
| MA20 | 24.5 | 29.1 | 26.6 |

Table 2: *in vitro* metabolic stability

| Compound | T$_{1/2}$ (Min) | % of remaining at 60 Min | Matrix |
|---|---|---|---|
| MA1 | 15.54 | 2.03 | HLM |
| MA20 | 115.13 | 99.45 | HLM |

SMALL MOLECULE SECURININE AND NORSECURININE ANALOGS AND THEIR USE IN INHIBITING MYELOPEROXIDASE

RELATED APPLICATIONS

This application claims priority to U.S. Provisional Application No. 61/886,448, filed Oct. 3, 2013, to U.S. Provisional Patent Application 61/942,880, filed Feb. 21, 2014 and to U.S. Provisional Patent Application 62/051,595, filed Sep. 17, 2014, all of which are hereby incorporated by reference in their entirety.

FIELD OF THE INVENTION

The application relates to the synthesis of small molecule compounds derived from securinine and norsecurinine and demonstrates the effectiveness of the compounds in inhibiting myeloperoxidase activity.

BACKGROUND

Securinine ($C_{13}H_{15}NO_2$; mw 217.2637; also known as CHEMBL303062; Securinin; Securinan-11-one; 5610-40-2; Securinine, (−)-; UNII-G4VS580P5E; NSC107413, as well as stereoisomers virosecurinine and allosecurinine) is a small molecule with the recognized two-dimensional structure:

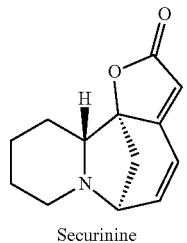 [SMILES: O=C1C=C2C=C[C@@H]3C[C@@]2(O1)[C@H]1CCCCN31]

Securinine

Securinine is a plant-derived alkaloid that has previously demonstrated efficacy for neurological related diseases. An unexpected rearranged derivative, norsecurinine, has recently been reported (Li et al., Tetrahedron 2012, 68, 3972-3979):

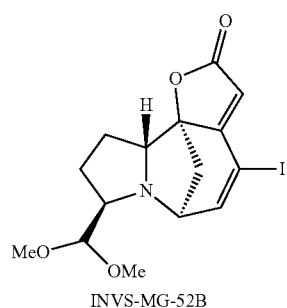 [SMILES: COC(OC)[C@H]1CC[C@H]2N1[C@@H]1C=C(I)C3=CC(=O)O[C@@]32C1]

INVS-MG-52B

As well as a brominated derivative:

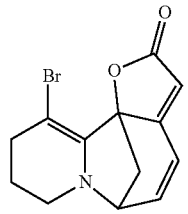 [SMILES: O=C1C=C2C=CC3CC2(O1)C1=C(Br)CCCN13]

Securinine is documented as an effective $GABA_A$ receptor antagonist with otherwise very low cellular toxicity (Beutler et al., Brain Res 330(1); 135-140, 1985; Lubick et al., J Leukoc Biol. 2007 November; 82(5):1062-9). Securinine has further been identified to induce apoptosis of promyelocytic leukemia cells and colon cancer cells at high doses and to induce monocytic differentiation of a wide range of myeloid leukemia cell lines as well as primary leukemic patient samples at low doses (Rana et al., 2010, The FASEB Journal, 24(6) 2126-2134; Dong et al., Zhongguo yao li xue bao=Acta pharmacologica Sinica 20.3 (1999): 267-270; Gupta et al., PLoS ONE 6(6): e21203. doi:10.1371/journal-.pone.0021203, 2011). Securinine has also been found to lead to cell killing of other cancer cell types such as breast cancer. (Li et al., Pharmazie 69: 217-23 (2014). Additional studies have focused on adapted structures derived from synthesizing the securinine molecule and noted its potential for a wide variety of infectious diseases such as parasitic disease. For example, the differences in activity on toxoplasma growth between the various derivatives (Holmes et al. *Experimental parasitology* 127.2 (2011): 370-375) was investigated. It also has activity against fungi (Sahni et al., *Mycobiology* 33.2 (2005): 97-103). Securinine has also been found to have activity in modulating infectious diseases through its ability to enhance the host immune response. For example, it enhances the ability of macrophages to clear a bacterial infection. (Lubick et al., *Journal of leukocyte biology* 82.5 (2007): 1062-1069).

Others have identified a natural reductase that reduces the γ,δ double bond of securinine and presented various derivatives of the reduced securinine (with functional groups affixed at C15) that also alter myeloid cell activity (Guan et al., *Biotechnology letters* 27.16 (2005): 1189-1193; US Published Patent Application 20140018383). Given the apparent diverse cellular activity offered by securinine as a backbone, investigations were aimed at identifying new cellular targets that analogs may interact with.

SUMMARY OF THE INVENTION

The present invention provides for methods of using securinine analogs, comprising administering one or more of the analogs to a myeloperoxidase enzyme, such as an enzyme with or proximal to a cell. As set out herein, the securinine analogs directly bind to and inhibit myeloperoxidase (MPO) activity. Accordingly, contacting or administering the analogs to an MPO enzyme allows for inhibition of MPO activity.

The present invention provides for methods of binding and/or inhibiting myeloperoxidase activity through using securinine analogs comprising the structure of:

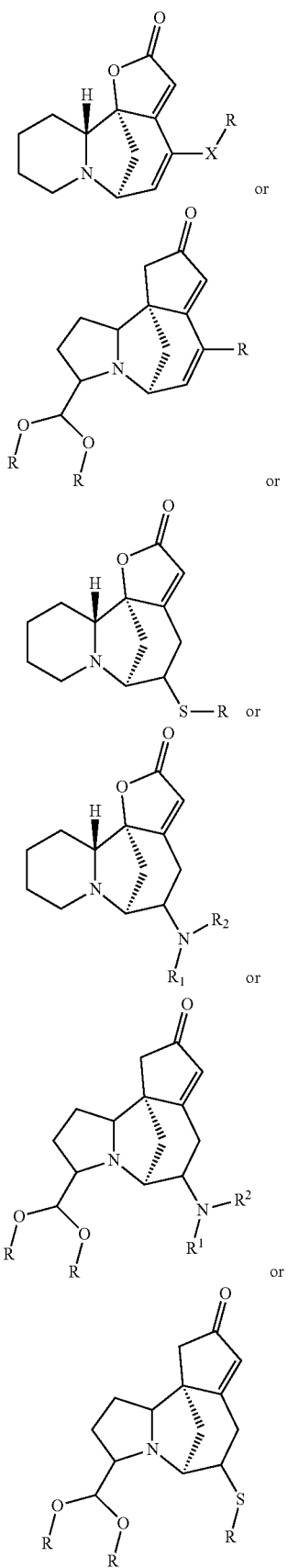

wherein X is a C, C—C, C=C or C≡C and R, $R_1$ or $R_2$ is a substituted or unsubstituted $C_1$-$C_{24}$ alkyl, $C_2$-$C_{24}$ alkenyl, $C_2$-$C_{24}$ alkynyl, hydrogen, halogen, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof.

The present invention provides for treating or ameliorating conditions associated with aberrant or harmful MPO activity, such as chronic obstructive pulmonary disease and atherosclerosis by administering the securinine and/or norsecurinine analogs and thereby reducing overall MPO activity. The analogs may be administered to a cell or in proximity to a cell subject to or potentially subject to damage by MPO activity.

BRIEF DESCRIPTION OF THE DRAWINGS

FIG. 6A shows a 2D structure of INVMG1. FIG. 6B shows a silver staining of a protein gel, with the lanes as follows: untreated, Lane 1; Biotin treated, Lane 2; Biotin-INVMG1, Lane 3 and Marker Lane 4 (red arrow indicates the unique protein band). FIG. 6C shows a western blot of a gel similar to 4B of corresponding pull down elute (lane 1-3); lane 4 direct cell extract. FIG. 6D shows heme absorption spectra MPO+INVMG1, no chloride (Black). Only MPO (red) and $H_2O_2$ promoted a shift in the Soret peak, formation of a new band at 630 nm (blue). FIG. 6E shows the docking of INVMG1 in MPO crystal structure 3ZSO from PDB is used with inhibitor bound removed using Autodock generated using Pymol. FIG. 6F shows MALDI/TOF of Heme (Red), when conjugated with 184B in presence $H_2O_2$(Blue).

DESCRIPTION

Figure 1:
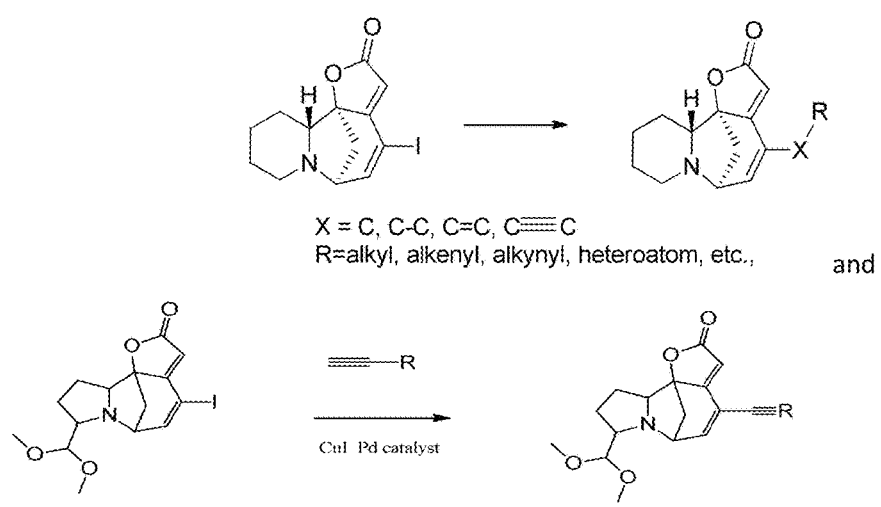
FIG. 1 shows an overview of the synthesis of securinine and norsecurinine analogs.
Figure 2:
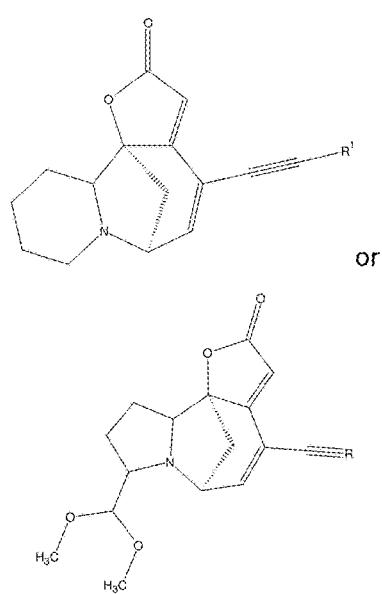
FIG. 2 shows an overview of the basic structure of securinine and norsecurinine analogs.

The present invention provides for using securinine and norsecurinine derived small molecules, namely synthetic analogs of securinine and norsecurinine to bind and/inhibit myeloperoxidase (MPO). The present invention in part provides for a non-reduced γ,δ double bond of securinine with functional groups attached at C14, based on the following numbering:

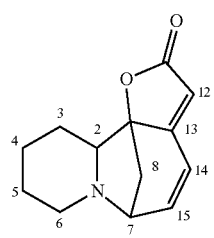

The present invention also provides for further analogs derived from the norsecurinine isomer with a non-reduced γ,δ double bond with functional groups attached at C14. The present invention also provides for compounds with a reduced γ,δ double bond of securinine and norsecurinine and functional groups attached at the C14 and/or C15.

The present invention provides for securinine and norsecurinine derived compounds of the following formula:

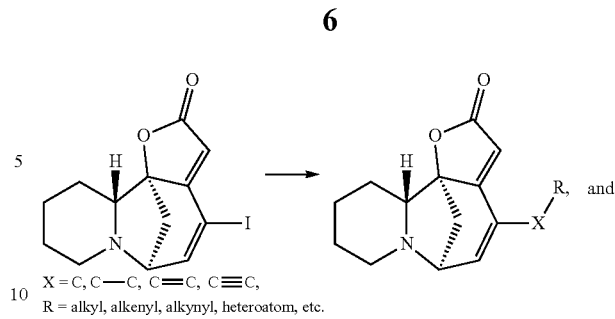

X = C, C—C, C═C, C≡C,
R = alkyl, alkenyl, alkynyl, heteroatom, etc.

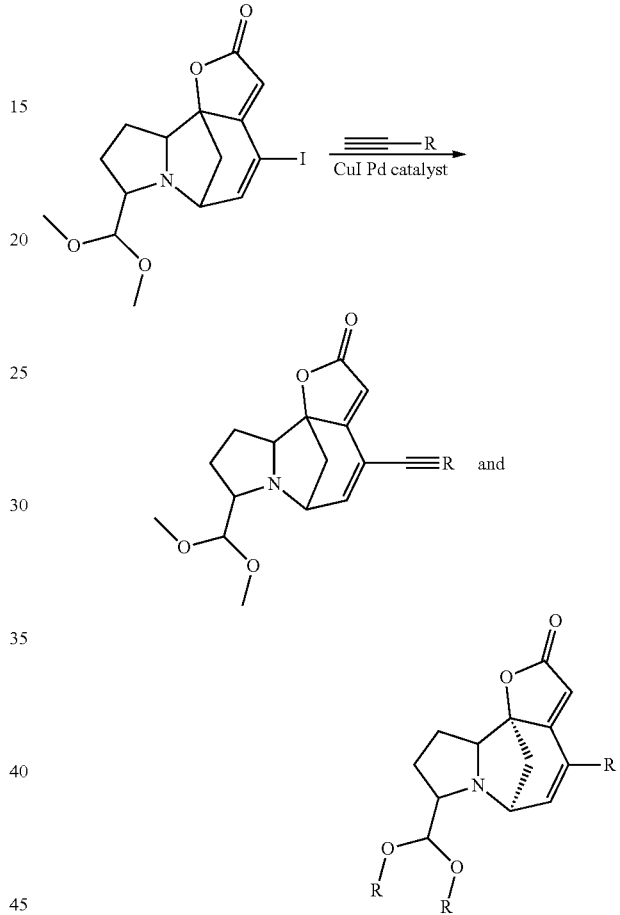

wherein X is a C, C—C, C═C or C≡C and any R is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof and pharmaceutically acceptable salts thereof. By way of example, R may include the following structures:

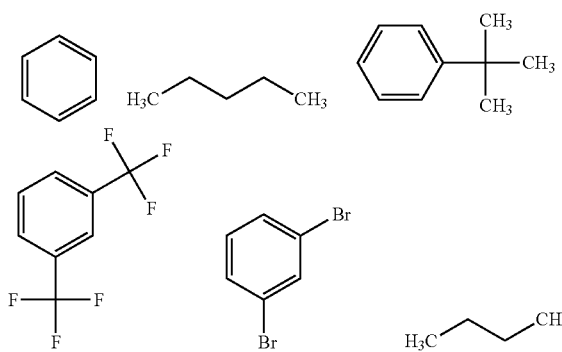

The present invention provides for small molecule alkynyl analogues of securinine and norsecurinine of the following formula:

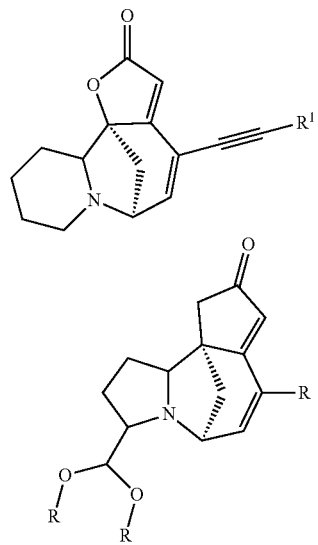

wherein R or R1 is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof and pharmaceutically acceptable salts thereof. By way of example, R and R1 may include the following structures:

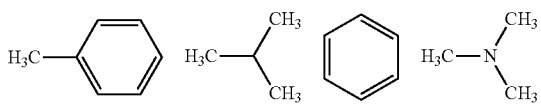

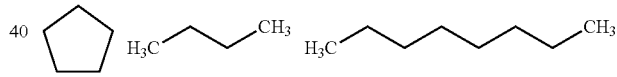

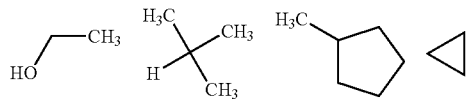

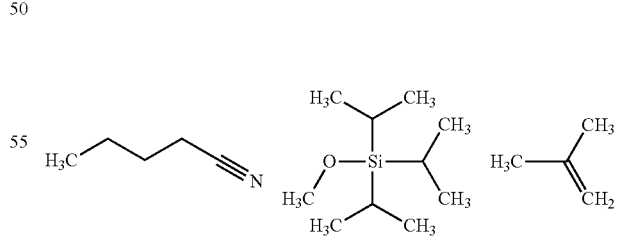

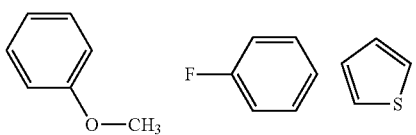

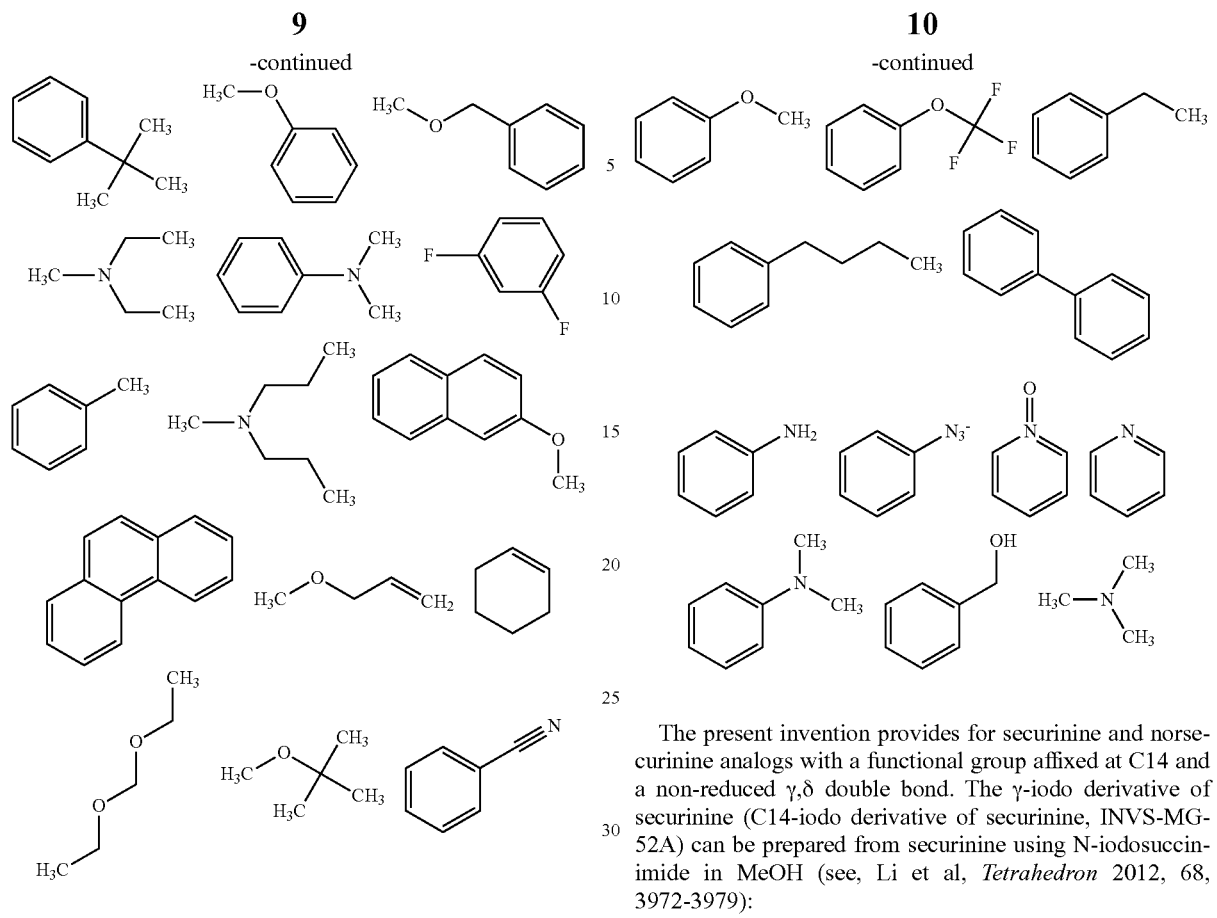

The present invention provides for securinine and norsecurinine analogs with a functional group affixed at C14 and a non-reduced γ,δ double bond. The γ-iodo derivative of securinine (C14-iodo derivative of securinine, INVS-MG-52A) can be prepared from securinine using N-iodosuccinimide in MeOH (see, Li et al, *Tetrahedron* 2012, 68, 3972-3979):

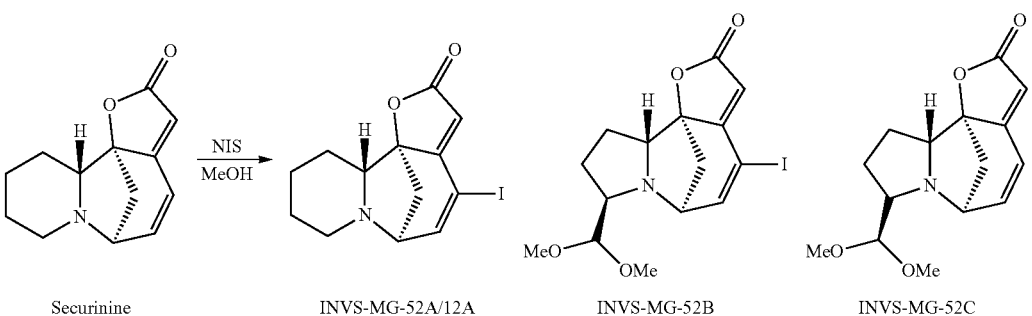

| Securinine | INVS-MG-52A/12A | INVS-MG-52B | INVS-MG-52C |

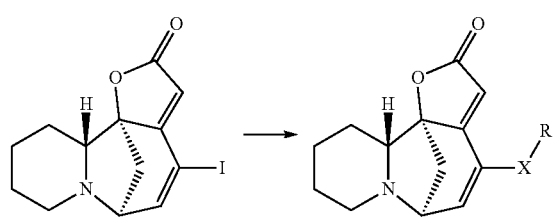

X = C—C, C=C, C≡C
R = alkyl, alkenyl, alkynyl, heteroatom, etc.,

During the product isolation from the reaction mixture, side products INVS-MG-52B and INVS-MG-52D may also be isolated. The intermediates INVS-MG-52A and INVS-MG-52B can then be adapted to prepare further C-14 analogs of securinine. Those skilled in the art will appreciate that the analogs described herein can further be obtained through modifications to the synthetic pathways as those described herein.

An example of the synthesis of C-14 alkyl/aryl analogs of securinine can be prepared using INVS-MG-52A and the corresponding boronic acids/esters as follows:

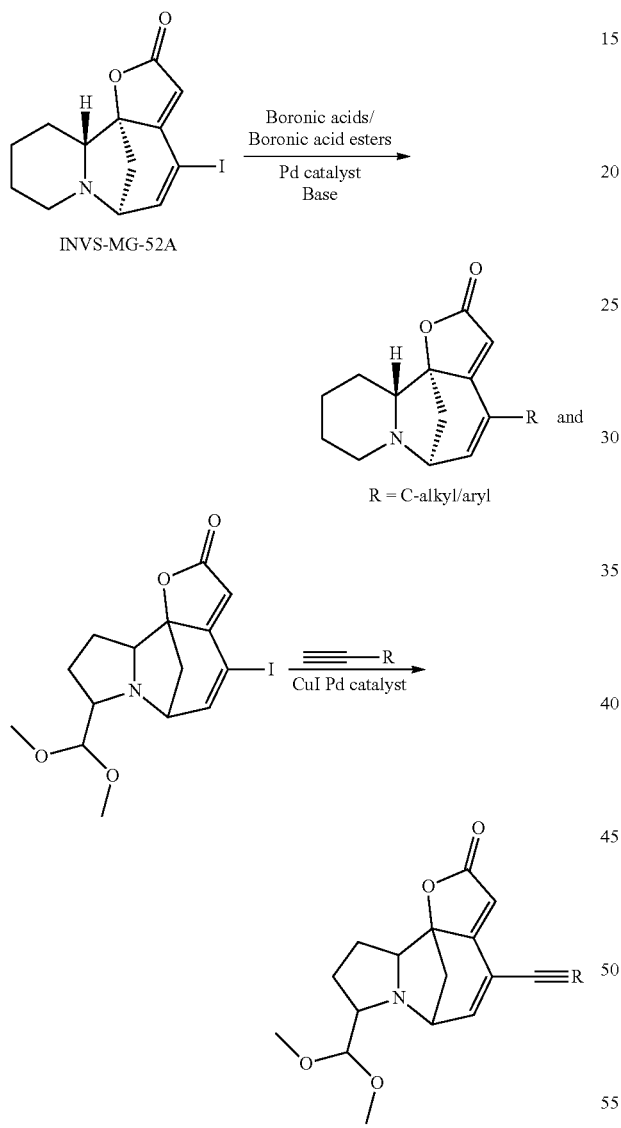

By way of example, and not by way of limitation, bis(triphenylphosphine)palladium(II)dichloride can be added to a solution comprising INVS-MG-52A or INVS-MG-52B in a solvent, such as anhydrous toluene or tetrahydrofuran, followed by adding the corresponding boronic acid and potassium carbonate/water. The reaction mixture can then be degassed under nitrogen atmosphere and then heated to 80° C. to 100° C. The reaction mixture may then be extracted, dried and concentrated. The crude product can be purified by chromatography using an appropriate solvent system to afford the desired C-14 alkyl/aryl analog of securinine in 40-70% yield. The following C-14 alkyl/aryl analogs of securinine have been synthesized employing the above:

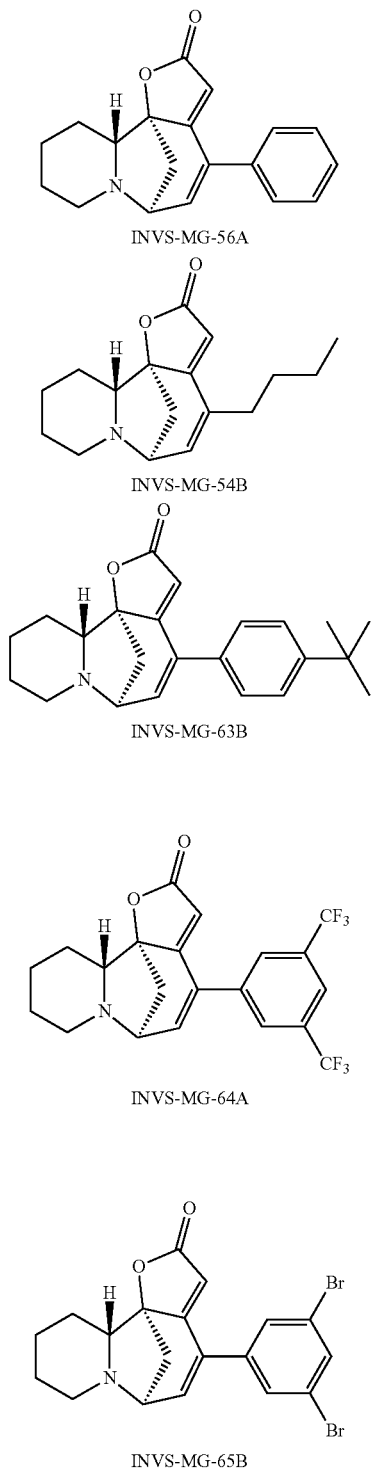

The process comprising the synthesis of C-14 alkynyl analogs of securinine and norsecurinine can be prepared using INVS-MG-52A or INVS-MG-52B and the corresponding terminal alkynes as outlined below.

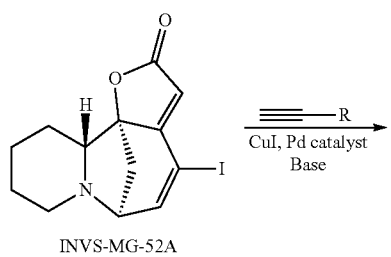

INVS-MG-52A

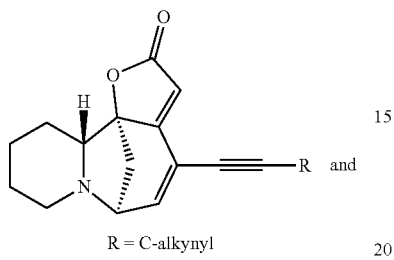

R = C-alkynyl

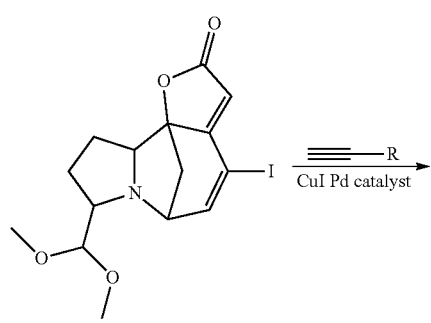

wherein R=alkyl, aryl or vinylic.

By way of further example, to a solution of INVS-MG-52A or INVS-MG-52B in anhydrous 1,4-dioxane/tetrahydrofuran may be added bis(triphenylphosphine)palladium (II)dichloride, copper (I) iodide and tryethylamine. The reaction mixture can be then degassed under nitrogen atmosphere and then gradually heated to 80° C. Heat can then be removed to bring the reaction mixture to room temperature, and the corresponding alkyne added. The reaction mixture can then be poured in water and extracted, such as with ethylacetate, and then dried and concentrated. The following C-14 alkynyl analogs of securinine have been synthesized employing the above procedure:

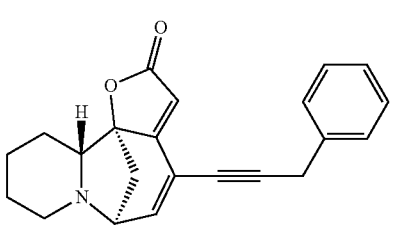

INVS-MG-108B

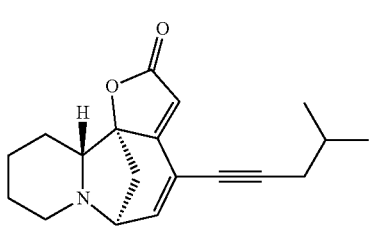

INVS-MG-109-IIA

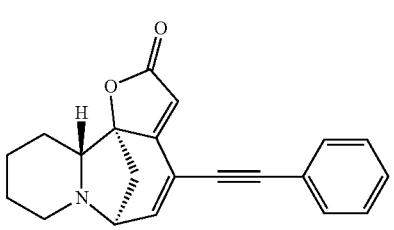

INVS-MG-110B

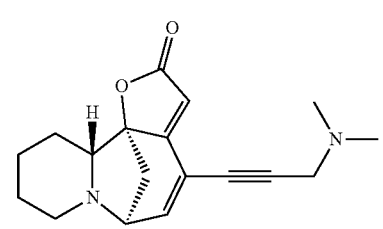

INVS-MG-111B

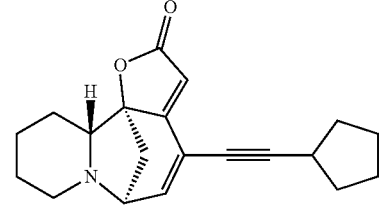

INVS-MG-113A

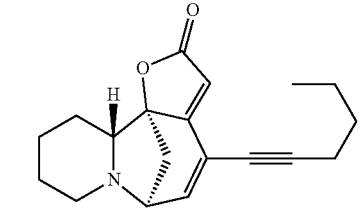

INVS-MG-117B

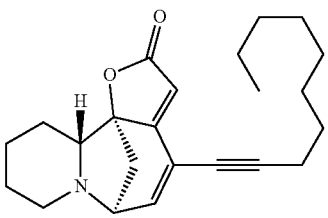

INVS-MG-118B

INVS-MG-120A
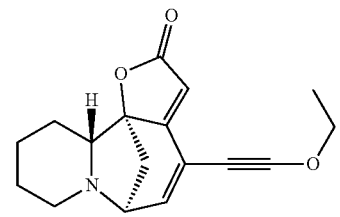
INVS-MG-121A
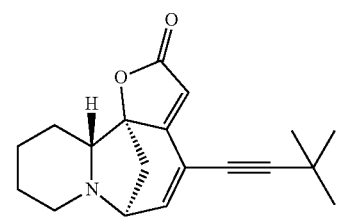
INVS-MG-123B
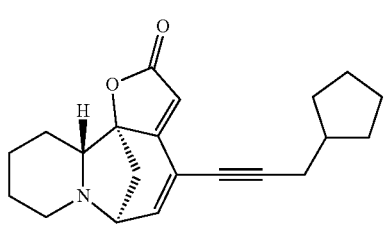
INVS-MG-124A
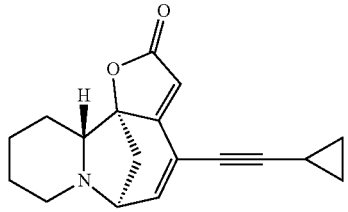
INVS-MG-125A
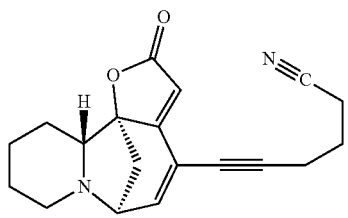
INVS-MG-131A
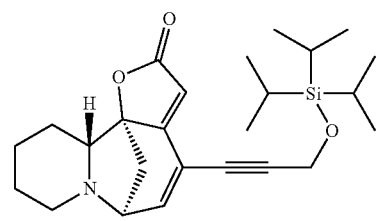
INVS-MG-132A
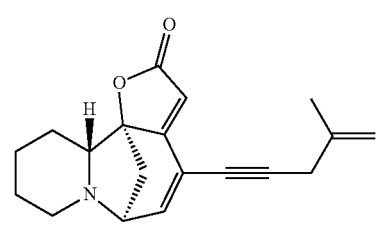
INVS-MG-134C
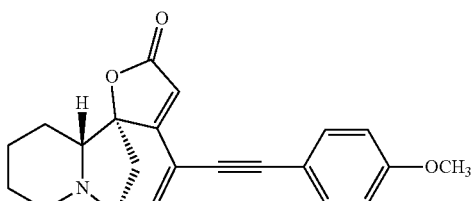
INVS-MG-135B
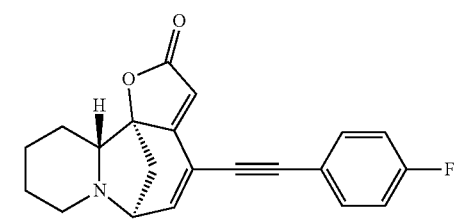
INVS-MG-136B
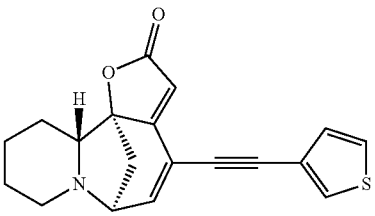
INVS-MG-133B
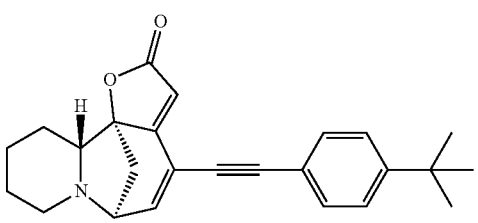
INVS-MG-133B
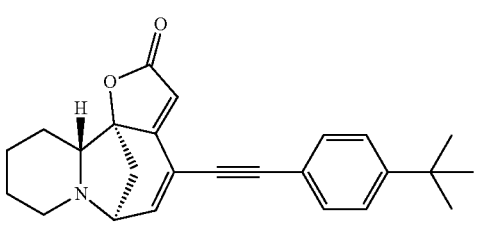
INVS-MG-137B
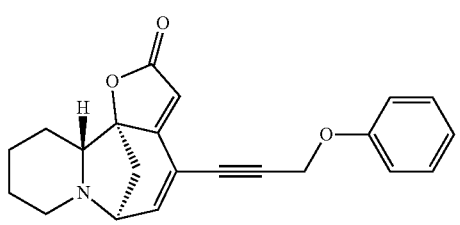

INVS-MG-138B
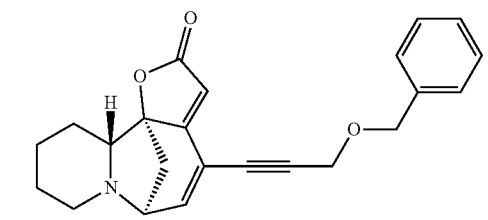
INVS-MG-145A
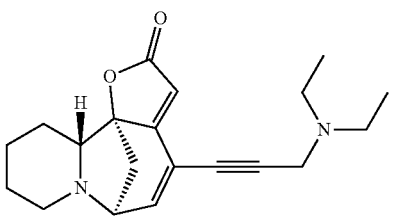
INVS-MG-146B
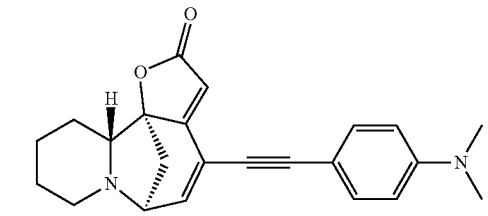
INVS-MG-150B
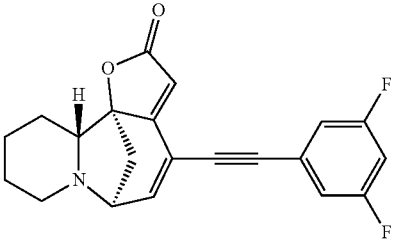
INVS-MG-151B
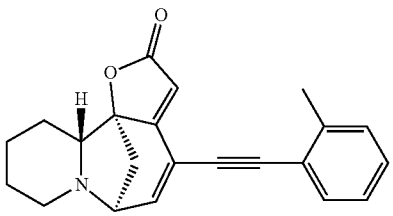
INVS-MG-152A
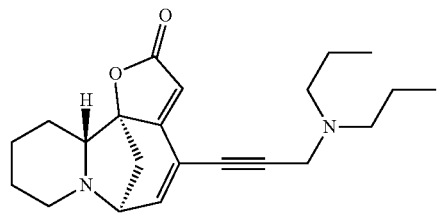
INVS-MG-157B
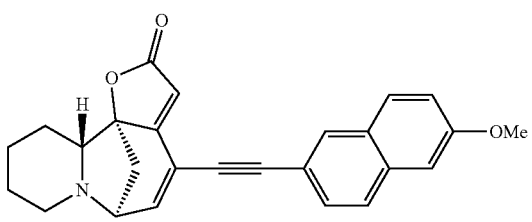
INVS-MG-158B
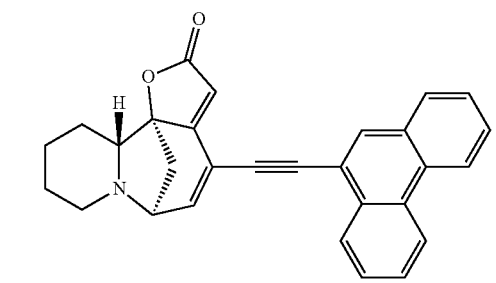
INVS-MG-159A
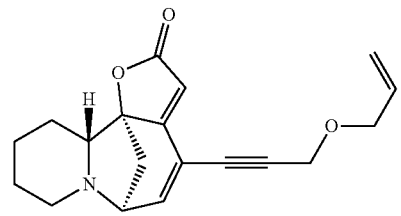
INVS-MG-160B
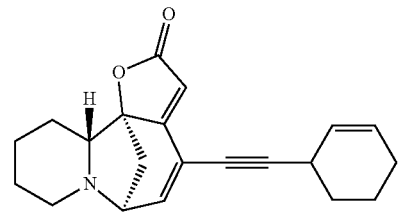
INVS-MG-161B
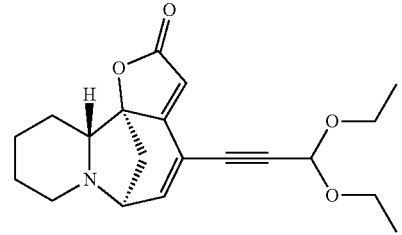
INVS-MG-162B
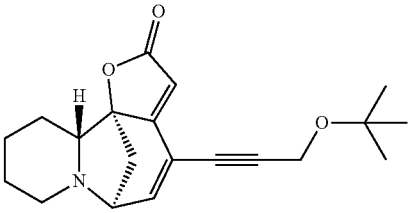

INVS-MG-164B

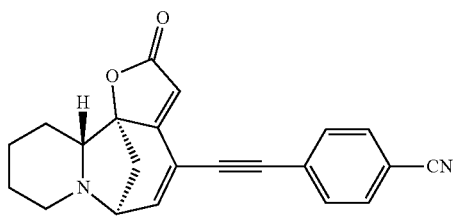

INVS-MG-165B

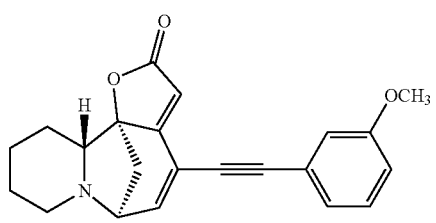

INVS-MG-166B

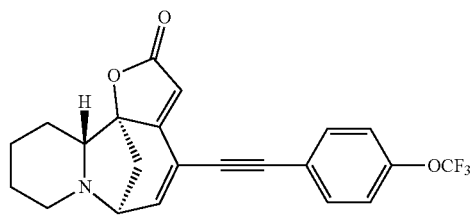

INVS-MG-167B

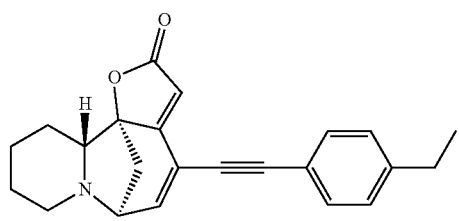

INVS-MG-168B

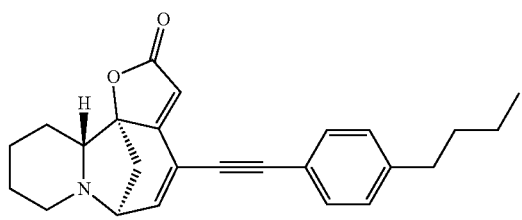

INVS-MG-169B

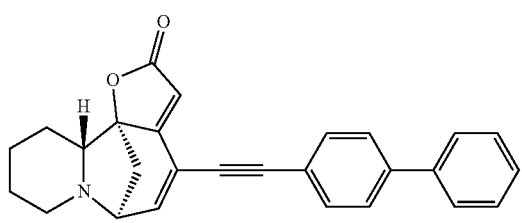

INVS-MG-170B

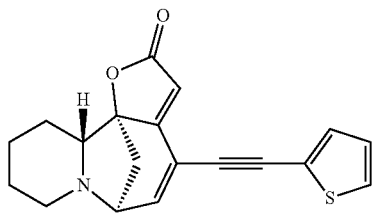

INVS-MG-175A

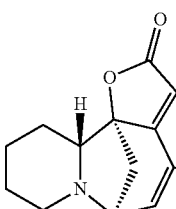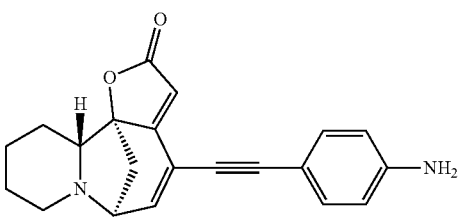

INVS-MG-193B

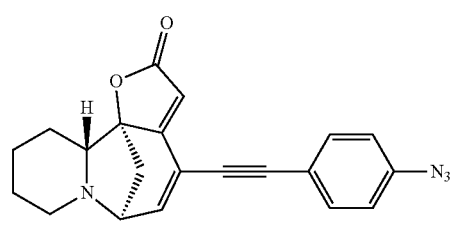

In another variation, the process comprising the synthesis of various pharmaceutically useful salts can be prepared as follows: a securinine or norsecurinine analog may be dissolved in 1,4-dioxane added to a 2N HCl/1,4-dioxane solution mixture at 0° C. The reaction mixture may be stirred as the product slowly precipitates. Hexanes or ether can then be added and the solids then filtered and washed to obtain the corresponding HCl salts. Similarly, a securinine analog can be dissolved in methanol and tartaric acid then added. The reaction mixture can be gradually heated to 80° C. as the product slowly precipitates. Ether can then be added and the solids filtered and washed to obtain the corresponding tartarate salts. Further still, securinine or norsecurinine analogs may be dissolved in methanol with tartaric acid added. The reaction mixture may be heated to 80° C. and product allowed to precipitate. Ether may then be added and the solids filtered and washed to obtain the corresponding tartarate salts. The following various pharmaceutically useful salts of securinine analogs have been thusly prepared, isolated and identified:

INVS-MG-70

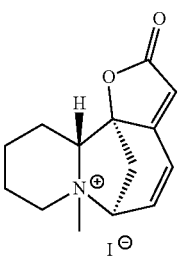

-continued

INVS-MG-72

INVS-MG-83

•[CH(OH)COOH]₂

INVS-MG-71

INVS-MG-73

INVS-MG-84

•[CH(OH)COOH]₂

INVS-MG-111-IV

•HCl

-continued

INVS-MG-125-III

•HCl

INVS-MG-157-III

•HCl

INVS-MG-158-III

•HCl

INVS-MG-169-III

•HCl

INVS-MG-170-III

•HCl

INVS-MG-146-III

•2HCl

INVS-MG-152-III
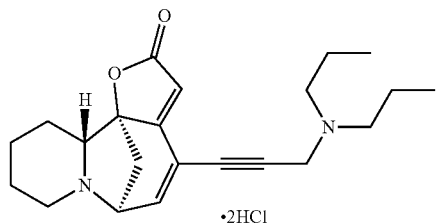
INVS-MG-175-V
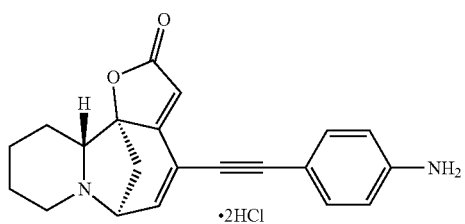
INVS-MG-193-III
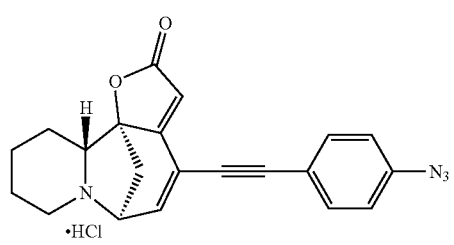
INV-SZ-113-2
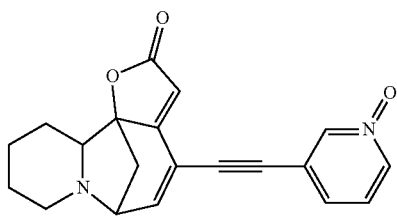
INV-SZ-114-1
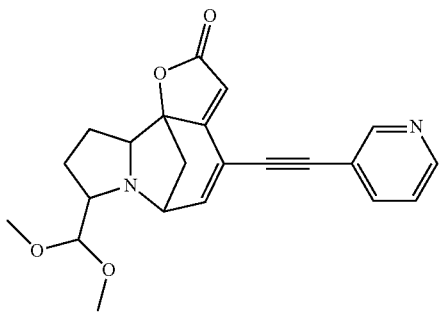
INV-SZ-115-1
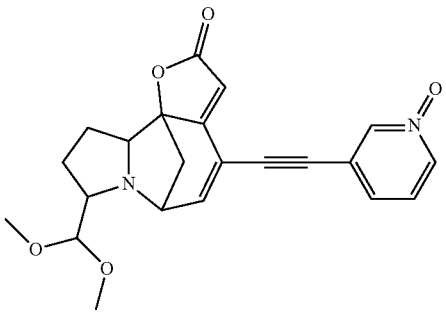
INV-SZ-116-1
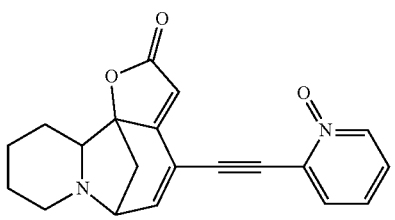
INV-SZ-117-3
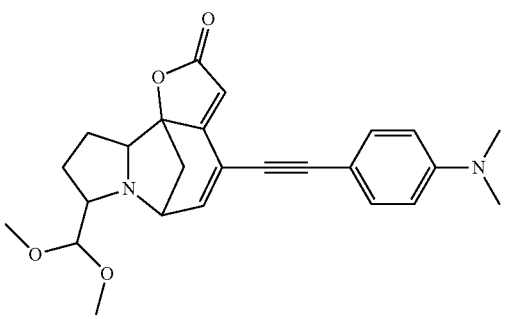
INV-SZ-118-2
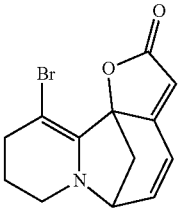
INV-SZ-120-1
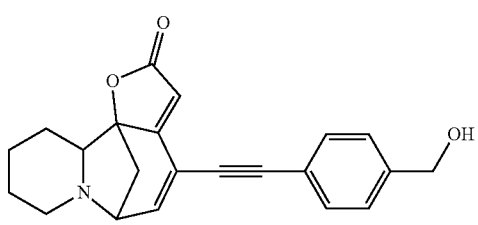
INV-SZ-121-1
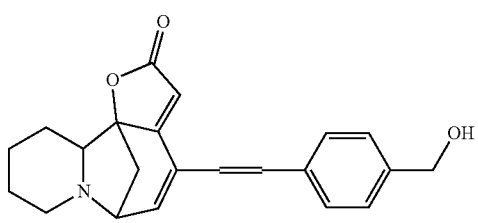

INV-SZ-122-1
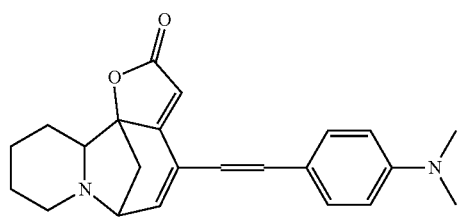
INV-SZ-123-2
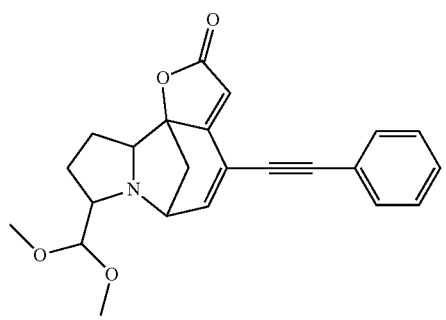
INV-SZ-123-3
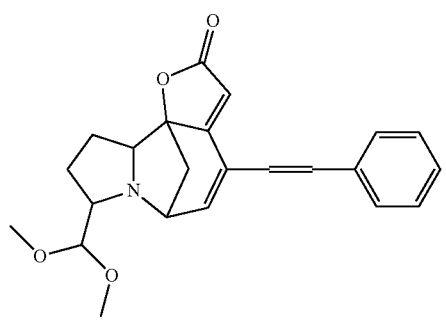
INV-SZ-125-1
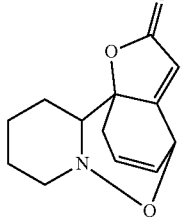
INV-SZ-125-2
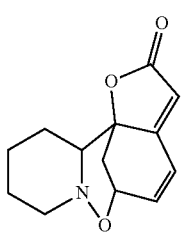
INV-SZ-125-3
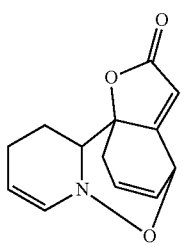
INV-SZ-127-1
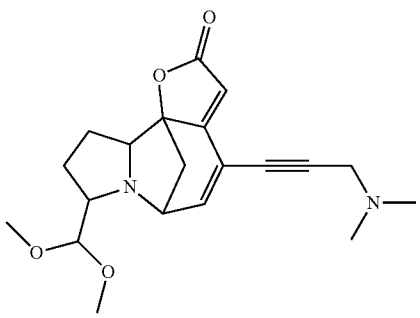
INV-SZ-129-1
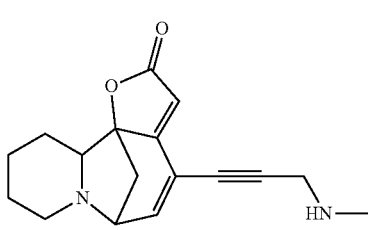
C-15 reduced analogs of securinine can be prepared by 1,6-conjugate addition of thials/amines following the general procedure:
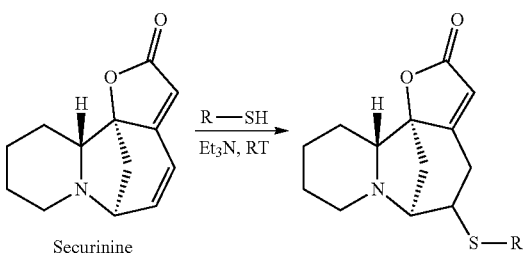
or with norsecurinine as the starting material to obtain:
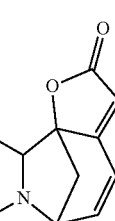
and

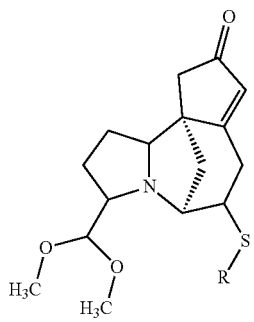

wherein R, $R_1$ and $R_2$ is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl) silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof and pharmaceutically acceptable salts thereof.

The following C-15 analogs of securinine have been synthesized employing the above process:

INVS-MG-3B

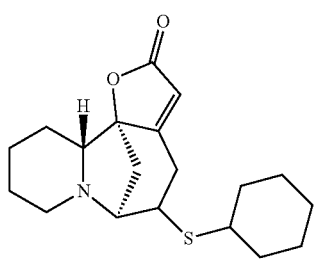

INVS-MG-4B

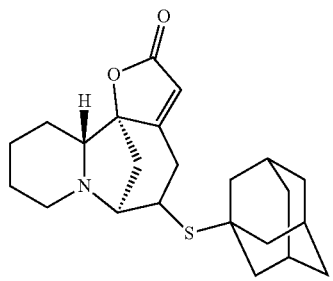

INVS-MG-5C

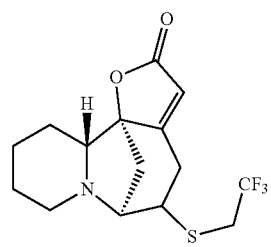

INVS-MG-9A

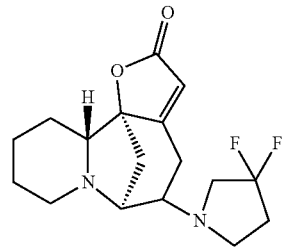

INVS-MG-14B

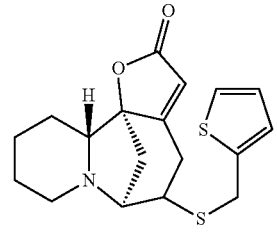

INVS-MG-16A

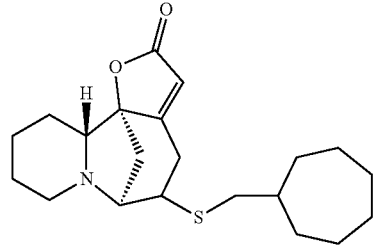

INVS-MG-19A

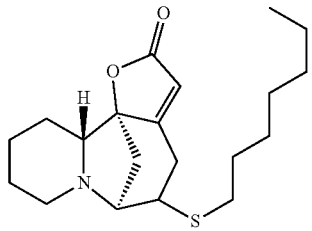

INVS-MG-20B
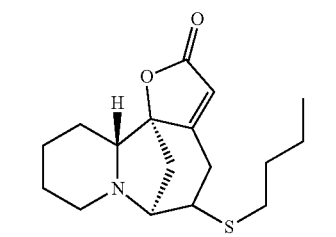
INVS-MG-106B
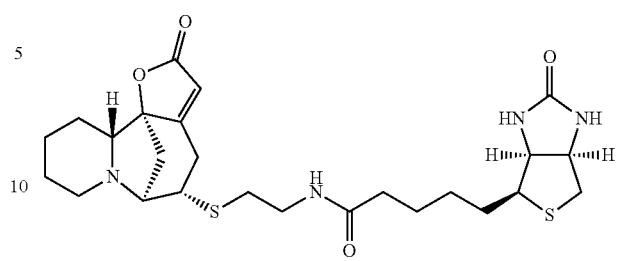
INVS-MG-21B
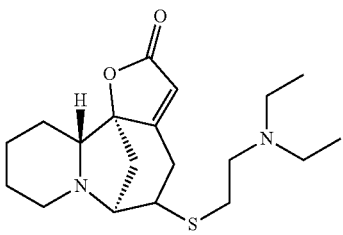
INVS-MG-25B
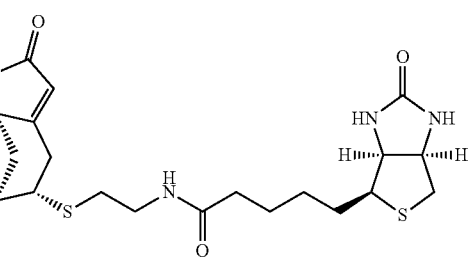
INVS-MG-34B/INV-2B
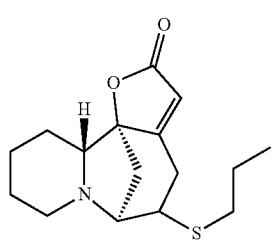
INVS-MG-26A
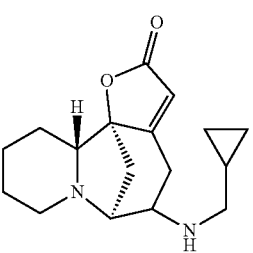
INVS-MG-37B/INV-26C
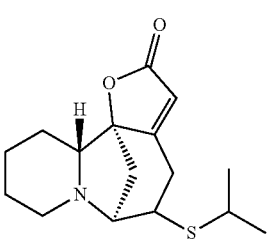
INVS-MG-27B
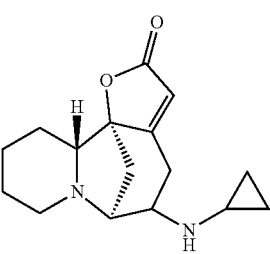
INVS-MG-57B
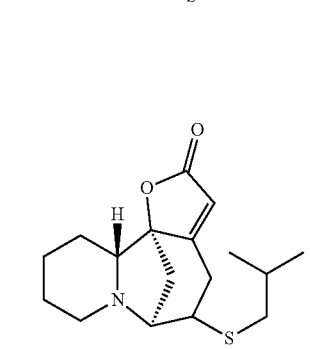
INVS-MG-28B
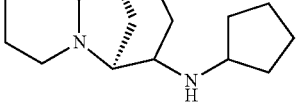
INVS-MG-105C
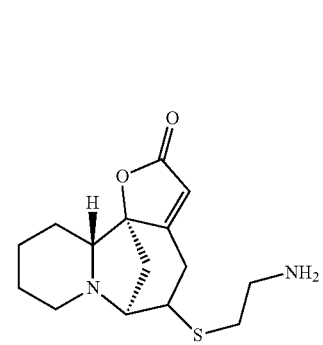
INVS-MG-29A
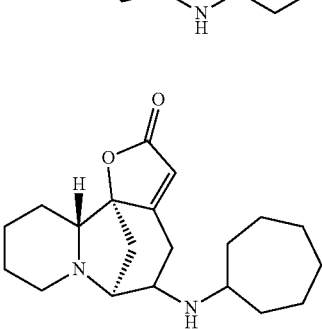

INVS-MG-30A
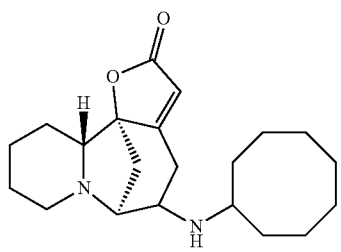
INVS-MG-46B
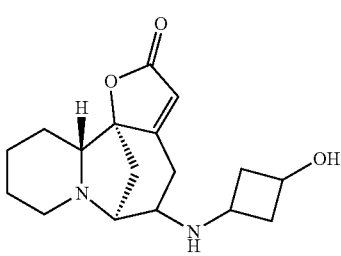
INVS-MG-86B
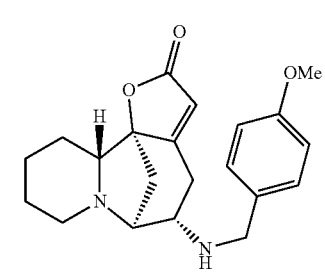
INVS-MG-172C
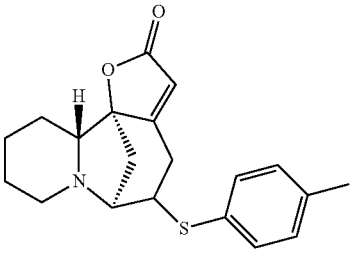
INVS-MG-184B
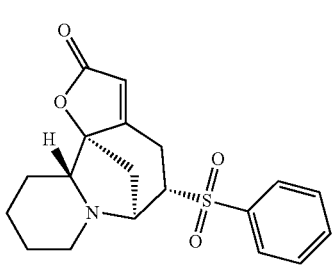
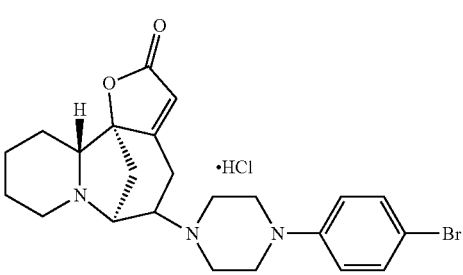
Sec-12
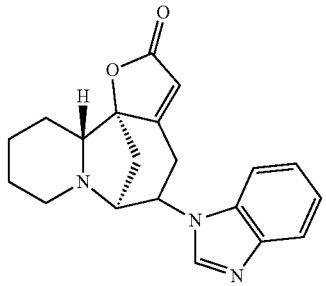
Sec-13
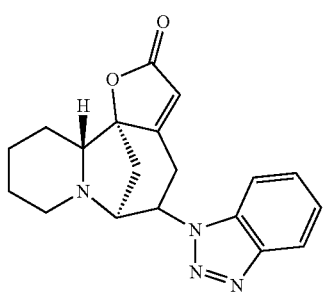
INV₂A
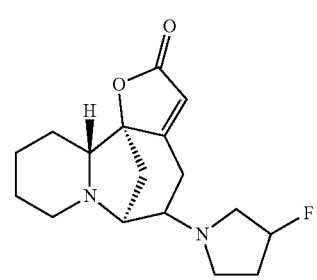
Sec 2
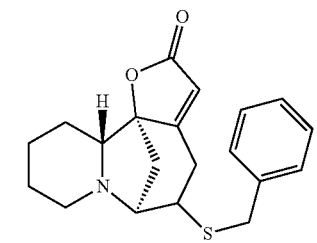
Sec 4
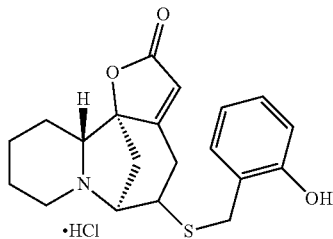
Sec 5
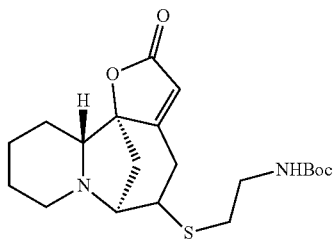

-continued
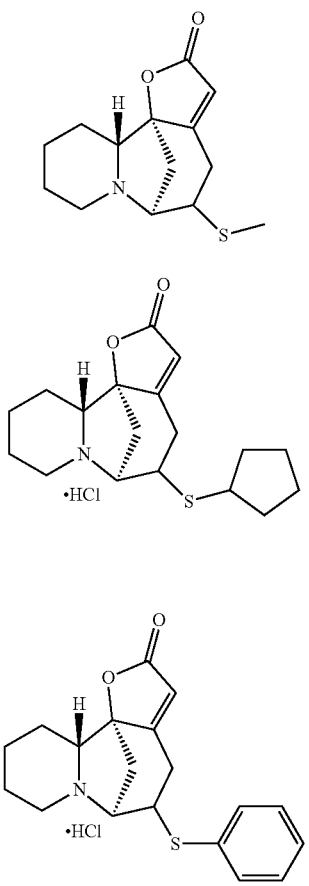
Sec 8
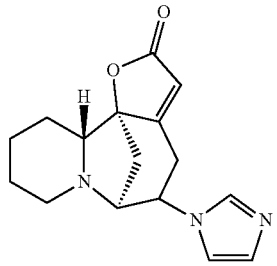
Sec 6
Sec 9
-continued
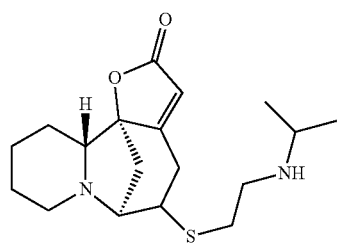
Sec 15
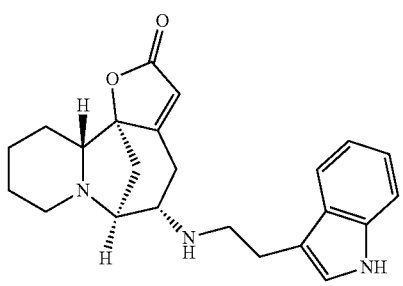
Sec 17
INVS-MG-98B
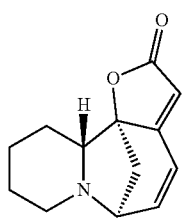 [SMILES: O=C1C=C2C=C[C@@H]3C[C@@]2(O1)[C@H]1CCCCN31]
The following list provides an example of securinine and/or norsecurinine analogs produced by the methods described herein:
| Sample Code | Chemical Structure |
|---|---|
| Securinine | 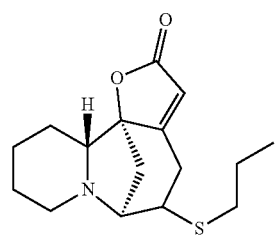 |
| INV-2B (INVS-MG-34B) | 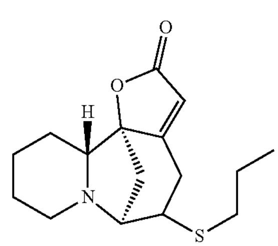 [SMILES: CCCSC1CC2=CC(=O)O[C@@]23C[C@@H]1N1CCCC[C@@H]13] |

-continued
| Sample Code | Chemical Structure |
|---|---|
| -26C/INVS-MG-37B/Sec-7/Sec-22 | 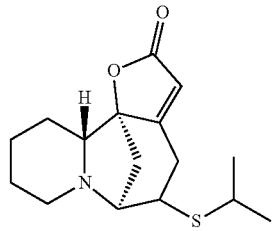 [SMILES: CC(C)SC1CC2=CC(=O)O[C@@]23C[C@@H]1N1CCCC[C@@H]13] |
| INVS-MG-3B | 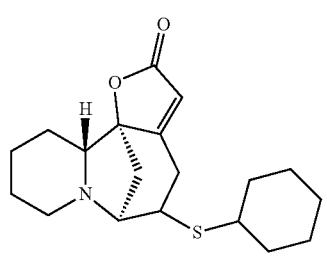 [SMILES: O=C1C=C2CC(SC3CCCCC3)[C@@H]3C[C@@]2(O1)[C@H]1CCCCN31] |
| INVS-MG-4B | 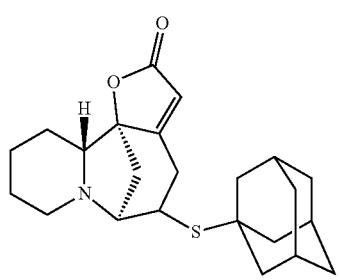 [SMILES: O=C1C=C2CC(SC34CC5CC(CC(C5)C3)C4)[C@@H]3C[C@@]2(O1)[C@H]1CCCCN31] |
| INVS-MG-5A | 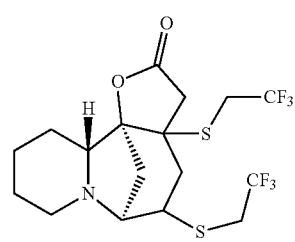 [SMILES: O=C1CC2(SCC(F)(F)F)CC(SCC(F)(F)F)[C@@H]3C[C@@]2(O1)[C@H]1CCCCN31] |
| INVS-MG-5B | 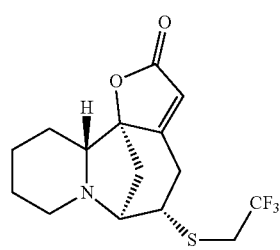 [SMILES: O=C1C=C2C[C@H](SCC(F)(F)F)[C@@H]3C[C@@]2(O1)[C@H]1CCCCN31] |
| INVS-MG-5C | 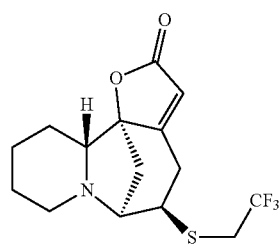 [SMILES: O=C1C=C2C[C@@H](SCC(F)(F)F)[C@@H]3C[C@@]2(O1)[C@H]1CCCCN31] |

-continued
| Sample Code | Chemical Structure |
|---|---|
| INVS-MG-7C | 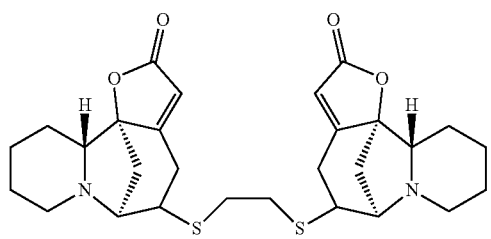 [SMILES: O=C1C=C2CC(SCCSC3CC4=CC(=O)O[C@]45C[C@H]3N3CCCC[C@H]35)[C@@H]3C[C@@]2(O1)[C@H]1CCCCN31] |
| INVS-MG-9A | 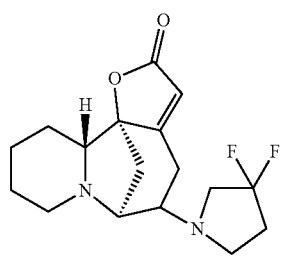 [SMILES: O=C1C=C2CC(N3CCC(F)(F)C3)[C@@H]3C[C@@]2(O1)[C@H]1CCCCN31] |
| INVS-MG-12A | 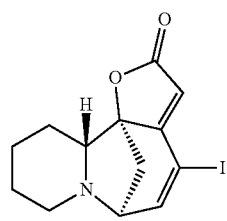 [SMILES: O=C1C=C2C(I)=C[C@@H]3C[C@@]2(O1)[C@H]1CCCCN31] |
| INVS-MG-14B | 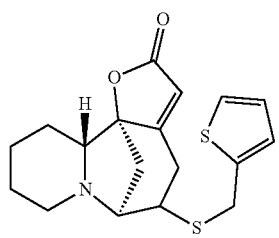 [SMILES: O=C1C=C2CC(SCc3cccs3)[C@@H]3C[C@@]2(O1)[C@H]1CCCCN31] |
| INVS-MG-16A | 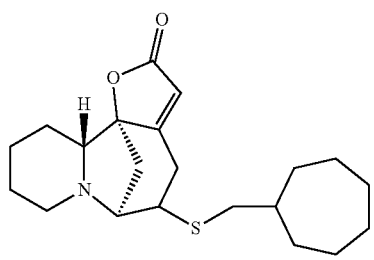 [SMILES: O=C1C=C2CC(SCC3CCCCCC3)[C@@H]3C[C@@]2(O1)[C@H]1CCCCN31] |
| INVS-MG-19A | 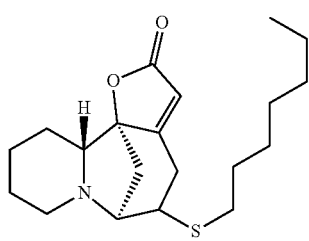 [SMILES: CCCCCCCSC1CC2=CC(=O)O[C@@]23C[C@@H]1N1CCCC[C@@H]13] |

-continued

| Sample Code | Chemical Structure |
|---|---|
| INVS-MG-20B | *(structure)* |
| INVS-MG-21B | *(structure)* |
| INVS-MG-26A | *(structure)* |
| INVS-MG-27B | *(structure)* |
| INVS-MG-28B | *(structure)* |
| INVS-MG-29A | *(structure)* |

-continued
| Sample Code | Chemical Structure |
|---|---|
| INVS-MG-30A | 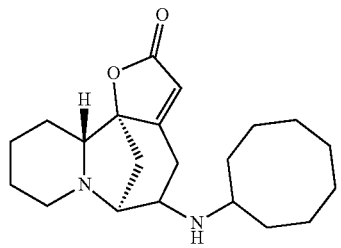 [SMILES: O=C1C=C2CC(NC3CCCCCCC3)[C@@H]3C[C@@]2(O1)[C@H]1CCCCN31] |
| Sec-1 | 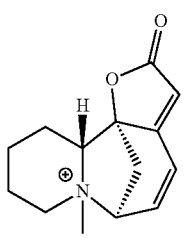 [SMILES: C[N+]12CCCC[C@@H]1[C@]13C[C@H]2C=CC1=CC(=O)O3] |
| Sec-2 | 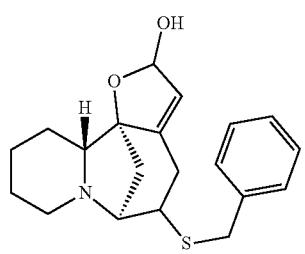 [SMILES: OC1C=C2CC(SCc3ccccc3)[C@@H]3C[C@@]2(O1)[C@H]1CCCCN31] |
| Sec-3 | 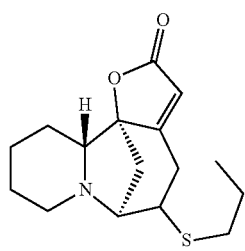 [SMILES: CCCSC1CC2=CC(=O)O[C@@]23C[C@@H]1N1CCCC[C@@H]13] |
| Sec-4 | 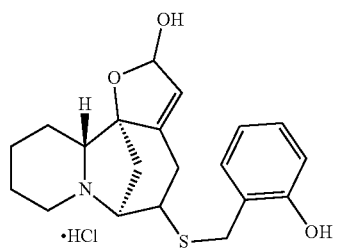 [SMILES: Oc1ccccc1CSC1CC2=CC(O)O[C@@]23C[C@@H]1N1CCCC[C@@H]13 ; Cl] |
| Sec-5 | 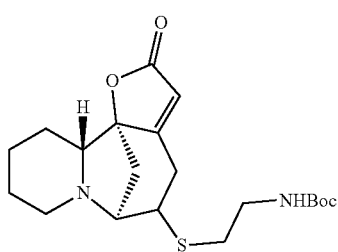 [SMILES: CC(C)(C)OC(=O)NCCSC1CC2=CC(=O)O[C@@]23C[C@@H]1N1CCCC[C@@H]13] |

-continued
| Sample Code | Chemical Structure |
|---|---|
| Sec-6 | 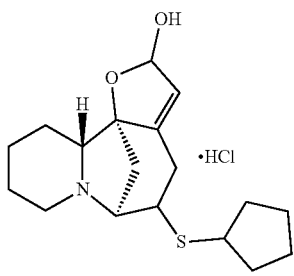 [SMILES: OC1C=C2CC(SC3CCCC3)[C@@H]3C[C@@]2(O1)[C@H]1CCCCN31 ; Cl] |
| Sec-8 | 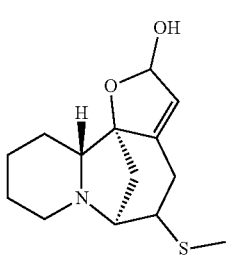 [SMILES: CSC1CC2=CC(O)O[C@@]23C[C@@H]1N1CCCC[C@@H]13] |
| Sec-9 | 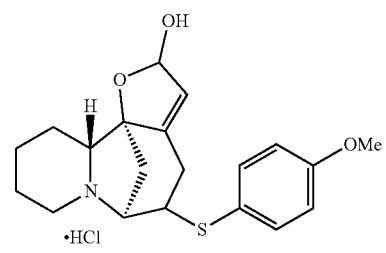 [SMILES: COc1ccc(SC2CC3=CC(O)O[C@@]34C[C@@H]2N2CCCC[C@@H]24)cc1 ; Cl] |
| Sec-11 | 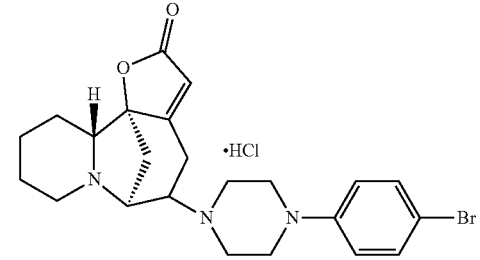 [SMILES: O=C1C=C2CC(N3CCN(c4ccc(Br)cc4)CC3)[C@@H]3C[C@@]2(O1)[C@H]1CCCCN31 ; Cl] |
| INVS-MG-25-B | 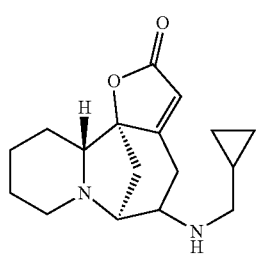 [SMILES: O=C1C=C2CC(NCC3CC3)[C@@H]3C[C@@]2(O1)[C@H]1CCCCN31] |
| INVS-MG-57A | 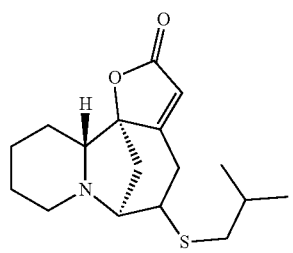 [SMILES: CC(C)CSC1CC2=CC(=O)O[C@@]23C[C@@H]1N1CCCC[C@@H]13] |

-continued

| Sample Code | Chemical Structure |
|---|---|
| Sec-12 | (structure: securinine-type scaffold with benzimidazol-1-yl substituent) |
| Sec-13 | (structure: securinine-type scaffold with benzotriazol-1-yl substituent) |
| Sec-15 | (structure: securinine-type scaffold with imidazol-1-yl substituent) |
| Sec-16 | (structure: reduced scaffold with tetrahydrofuran-2-ol) |
| Sec-17 | (structure: securinine-type scaffold with –S–CH$_2$CH$_2$–NH–iPr substituent) |
| Sec-18/20 | (structure: securinine-type scaffold with methyl substituent) |

-continued
| Sample Code | Chemical Structure |
|---|---|
| Sec-19 | 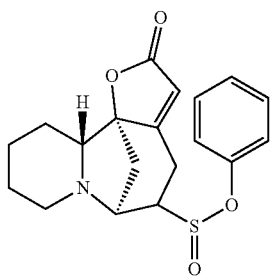 [SMILES: O=C1C=C2CC(S(=O)Oc3ccccc3)[C@@H]3C[C@@]2(O1)[C@H]1CCCCN31] |
| Sec-21 | 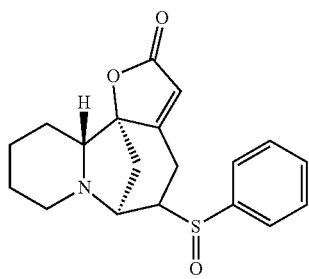 [SMILES: O=C1C=C2CC(S(=O)c3ccccc3)[C@@H]3C[C@@]2(O1)[C@H]1CCCCN31] |
| INVS-MG-55B & 57B/37B | 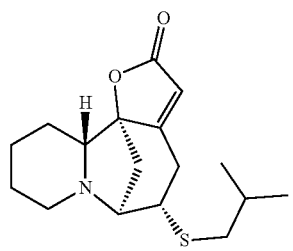 [SMILES: CC(C)CS[C@H]1CC2=CC(=O)O[C@@]23C[C@@H]1N1CCCC[C@@H]13] |
| INVS-MG-58C/34B | 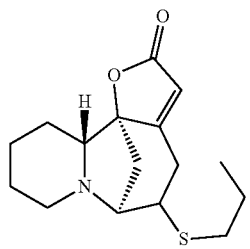 [SMILES: CCCSC1CC2=CC(=O)O[C@@]23C[C@@H]1N1CCCC[C@@H]13] |
| INVS-MG-63B | 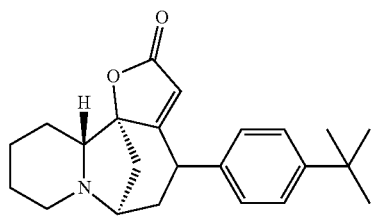 [SMILES: CC(C)(C)c1ccc(C2C[C@@H]3C[C@@]4(OC(=O)C=C24)[C@H]2CCCCN32)cc1] |
| INVS-MG-64A | 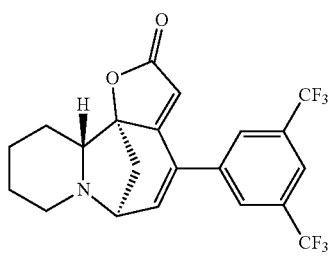 [SMILES: O=C1C=C2C(c3cc(C(F)(F)F)cc(C(F)(F)F)c3)=C[C@@H]3C[C@@]2(O1)[C@H]1CCCCN31] |

-continued
| Sample Code | Chemical Structure |
|---|---|
| INVS-MG-44 | 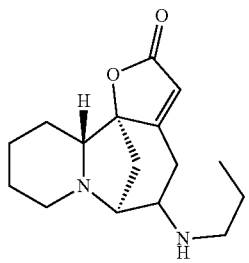 [SMILES: CCCNC1CC2=CC(=O)O[C@@]23C[C@@H]1N1CCCC[C@@H]13] |
| INVS-MG-65B | 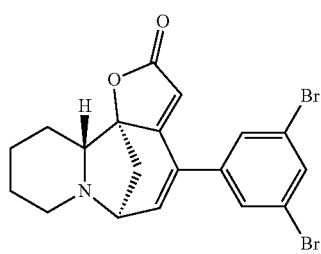 [SMILES: O=C1C=C2C(c3cc(Br)cc(Br)c3)=C[C@@H]3C[C@@]2(O1)[C@H]1CCCCN31] |
| INVS-MG-70 | 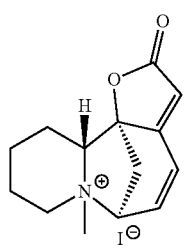 [SMILES: C[N+]12CCCC[C@@H]1[C@]13C[C@H]2C=CC1=CC(=O)O3 ; [I-]] |
| INVS-MG-71 | 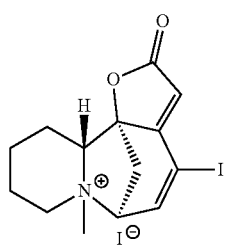 [SMILES: C[N+]12CCCC[C@@H]1[C@]13C[C@H]2C=C(I)C1=CC(=O)O3 ; [I-]] |
| INVS-MG-72/12A | 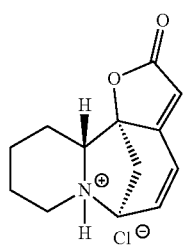 [SMILES: O=C1C=C2C=C[C@@H]3C[C@@]2(O1)[C@H]1CCCC[NH+]31 ; [Cl-]] |
| INVS-MG-74A | 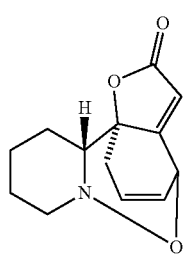 |

-continued
| Sample Code | Chemical Structure |
|---|---|
| Sec-23 | 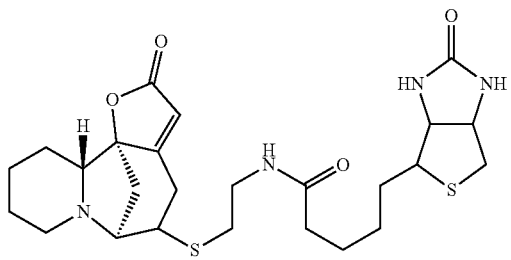 [SMILES: O=C(CCCCC1SCC2NC(=O)NC21)NCCSC1CC2=CC(=O)O[C@@]23C[C@@H]1N1CCCC[C@@H]13] |
| INVS-MG-46B | 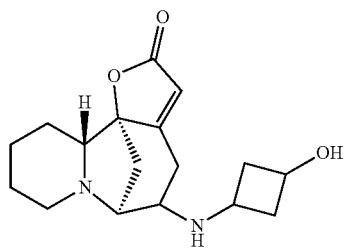 [SMILES: O=C1C=C2CC(NC3CC(O)C3)[C@@H]3C[C@@]2(O1)[C@H]1CCCCN31] |
| INVG-27-2/INVS-MG-52B | 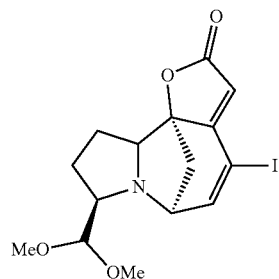 [SMILES: COC(OC)[C@H]1CCC2N1[C@@H]1C=C(I)C3=CC(=O)O[C@@]32C1] |
| INVG-Z-27-4/INVS-MG-52D | 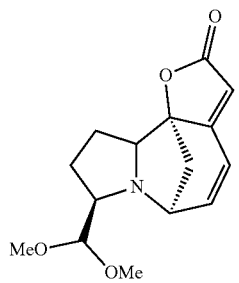 [SMILES: COC(OC)[C@H]1CCC2N1[C@@H]1C=CC3=CC(=O)O[C@@]32C1] |
| INVG-28-1/INVS-MG-56B | 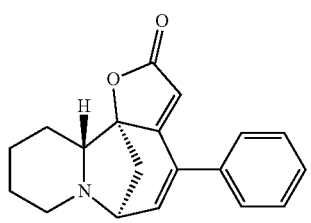 [SMILES: O=C1C=C2C(c3ccccc3)=C[C@@H]3C[C@@]2(O1)[C@H]1CCCCN31] |
| INVS-MG-54B | 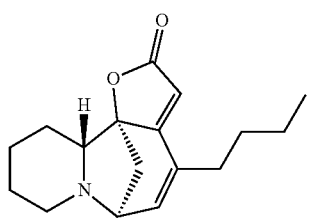 [SMILES: CCCCC1=C[C@@H]2C[C@@]3(OC(=O)C=C13)[C@H]1CCCCN21] |

-continued

| Sample Code | Chemical Structure |
|---|---|
| INVS-MG-59/Sec-22/INV-26C | *(structure with isopropylthio substituent)* |
| INVS-MG-60 | *(structure with -S-CH₂CH₂-N(Et)₂ substituent)* |
| INVS-MG-66B | *(structure with 2,3-dichlorophenyl substituent)* |
| INVS-MG-82/12A HCl salt | *(structure with iodo substituent, N⁺H Cl⁻)* |
| INVS-MG-83 | *(structure) ·[CH(OH)COOH]₂* |
| INVS-MG-84 | *(structure with iodo substituent) ·[CH(OH)COOH]₂* |

| Sample Code | Chemical Structure |
|---|---|
| INVS-MG-105C | 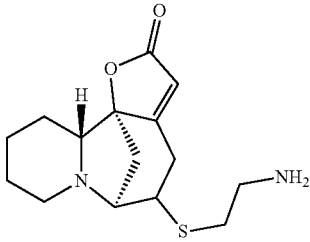 [SMILES: NCCSC1CC2=CC(=O)O[C@@]23C[C@@H]1N1CCCC[C@@H]13] |
| INVS-MG-86B | 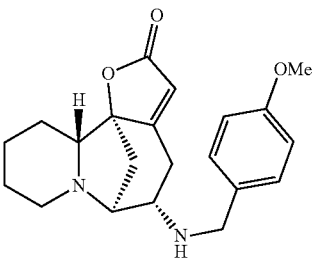 [SMILES: COc1ccc(CN[C@H]2CC3=CC(=O)O[C@@]34C[C@@H]2N2CCCC[C@@H]24)cc1] |
| INVS-MG-94 | 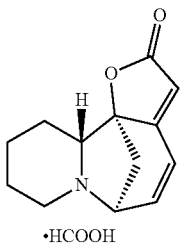 [SMILES: O=C1C=C2C=C[C@@H]3C[C@@]2(O1)[C@H]1CCCCN31 ; "·HCOOH"]<br>•HCOOH |
| INVS-MG-97-IIB | 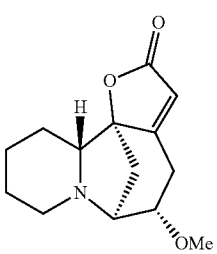 [SMILES: CO[C@H]1CC2=CC(=O)O[C@@]23C[C@@H]1N1CCCC[C@@H]13] |
| INVS-MG-97-IIE | 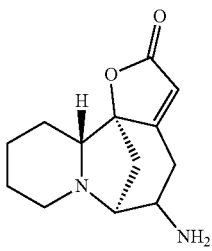 [SMILES: NC1CC2=CC(=O)O[C@@]23C[C@@H]1N1CCCC[C@@H]13] |
| INVS-MG-98B | 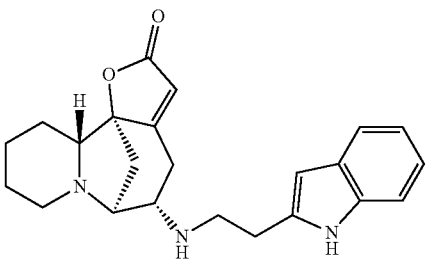 [SMILES: O=C1C=C2C[C@H](NCCc3cc4ccccc4[nH]3)[C@@H]3C[C@@]2(O1)[C@H]1CCCCN31] |

-continued
| Sample Code | Chemical Structure |
|---|---|
| INVS-MG-106B | 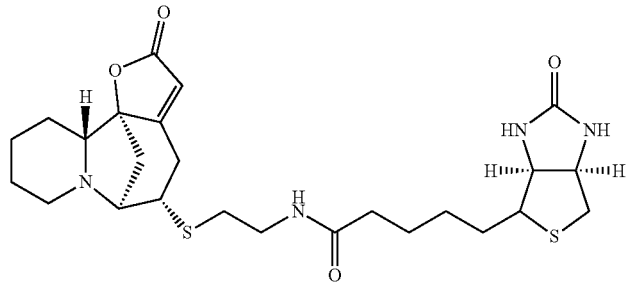 [SMILES: O=C(CCCCC1SC[C@@H]2NC(=O)N[C@H]12)NCCS[C@H]1CC2=CC(=O)O[C@@]23C[C@@H]1N1CCCC[C@@H]13] |
| INVS-MG-111B | 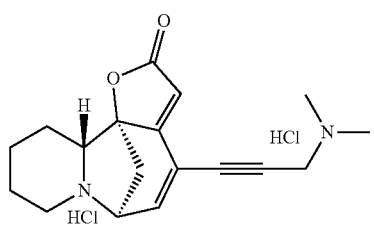 [SMILES: CN(C)CC#CC1=C[C@@H]2C[C@@]3(OC(=O)C=C13)[C@H]1CCCCN21 ; Cl ; Cl] |
| INVS-MG-52D | 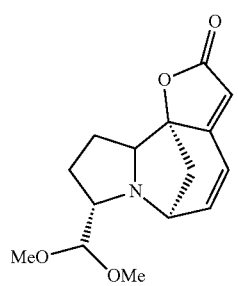 [SMILES: COC(OC)[C@@H]1CCC2N1[C@@H]1C=CC3=CC(=O)O[C@@]32C1] |
| INVS-MG-108-IIB | 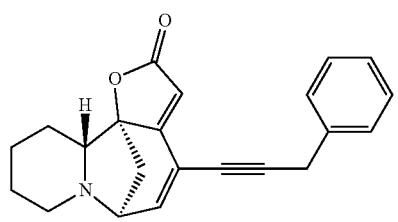 [SMILES: O=C1C=C2C(C#CCc3ccccc3)=C[C@@H]3C[C@@]2(O1)[C@H]1CCCCN31] |
| INVS-MG-109-IIA | 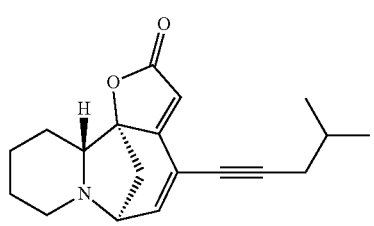 [SMILES: CC(C)CC#CC1=C[C@@H]2C[C@@]3(OC(=O)C=C13)[C@H]1CCCCN21] |
| INVS-MG-110B | 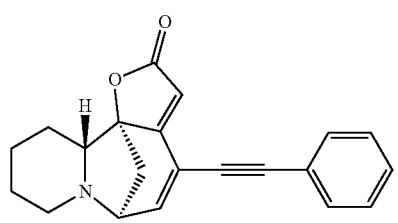 [SMILES: O=C1C=C2C(C#Cc3ccccc3)=C[C@@H]3C[C@@]2(O1)[C@H]1CCCCN31] |

-continued
| Sample Code | Chemical Structure |
|---|---|
| INVS-MG-111B | 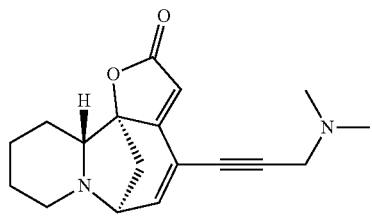 |
| INVS-MG-113A | 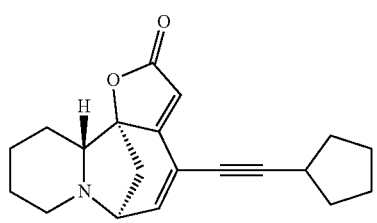 [SMILES: O=C1C=C2C(C#CC3CCCC3)=C[C@@H]3C[C@@]2(O1)[C@H]1CCCCN31] |
| INVS-MG-110B | 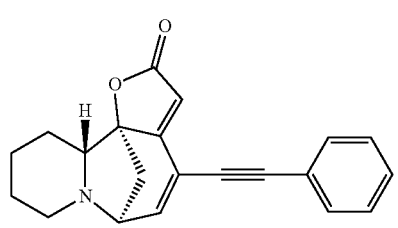 [SMILES: O=C1C=C2C(C#Cc3ccccc3)=C[C@@H]3C[C@@]2(O1)[C@H]1CCCCN31] |
| INVS-MG-86B | 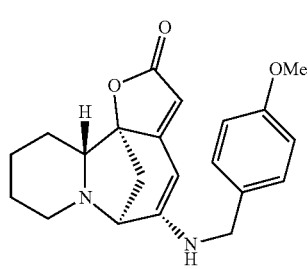 |
| INVS-MG-94 | 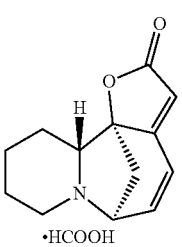 [SMILES: O=C1C=C2C=C[C@@H]3C[C@@]2(O1)[C@H]1CCCCN31 ; "·HCOOH"] |
| INVS-MG-97-IIB | 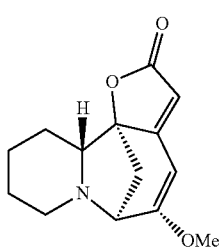 |

-continued

| Sample Code | Chemical Structure |
|---|---|
| INVS-MG-97-IIE | 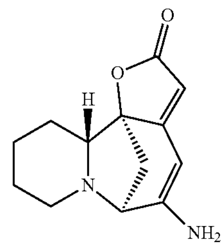 [SMILES: NC1=CC2=CC(=O)O[C@@]23C[C@@H]1N1CCCC[C@@H]13] |
| INVS-MG-98B | 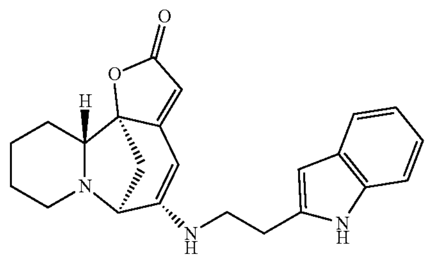 |
| 1NVS-MG-106B | 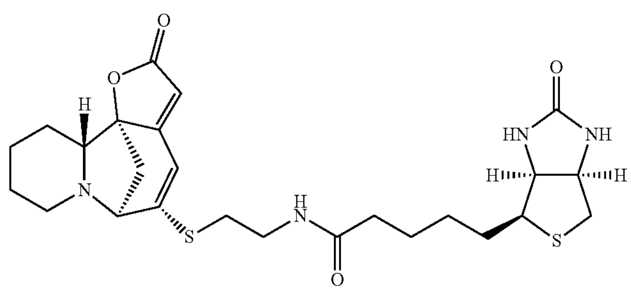 |
| INVS-MG-111B | 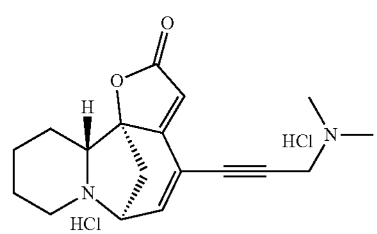 [SMILES: CN(C)CC#CC1=C[C@@H]2C[C@@]3(OC(=O)C=C13)[C@H]1CCCCN21 ; Cl ; Cl] |
| INVS-MG-52D | 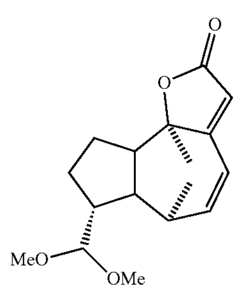 |
| INVS-MG-108-IIB | 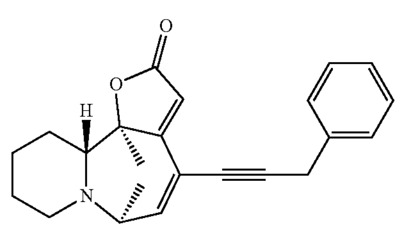 |

-continued

| Sample Code | Chemical Structure |
|---|---|
| INVS-MG-109-IIA | 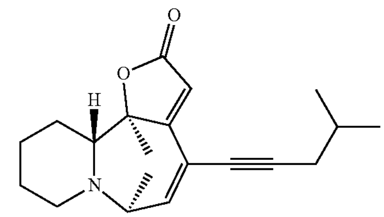 |
| INVS-MG-110B | |
| INVS-MG-111B | 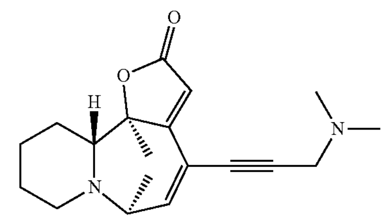 |
| INVS-MG-113A | 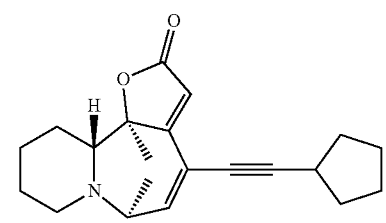 |
| INVS-MG-110B | |
| INVS-MG-117B | 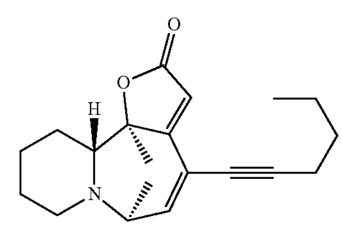 |
| INVS-MG-120A | 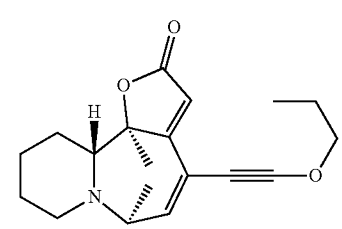 |

-continued

| Sample Code | Chemical Structure |
|---|---|
| INVS-MG-121A | 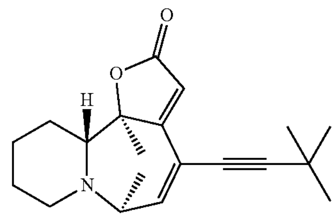 |
| INVS-MG-123B | 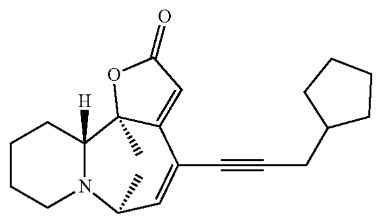 |
| INVS-MG-124A | 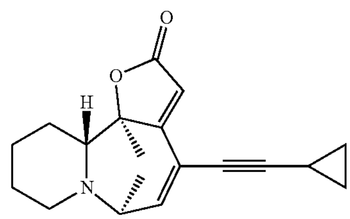 |
| INVS-MG-125A | 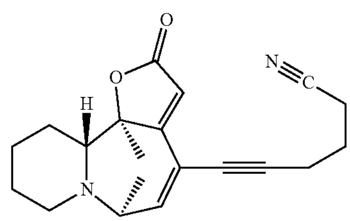 |
| INVS-MG-152A | 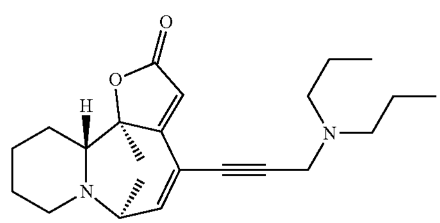 |
| INVS-MG-119A | 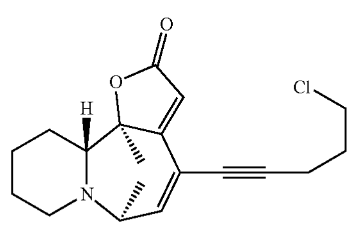 |
| INVS-MG-119B | 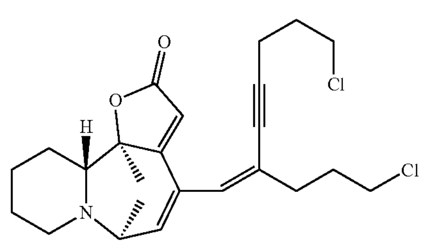 |

-continued
| Sample Code | Chemical Structure |
|---|---|
| INVS-MG-125-IIB | 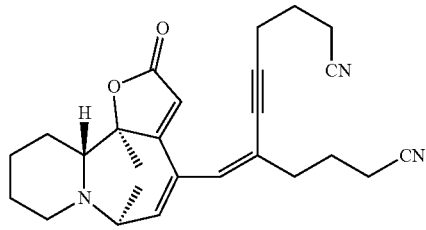 |
| INVS-MG-147B | 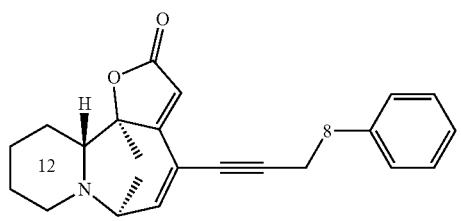 |
| INVS-MG-132A | 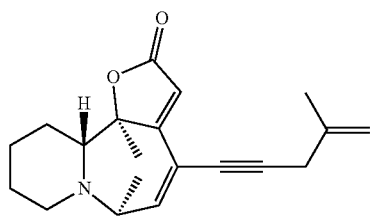 |
| INVS-MG-134C | 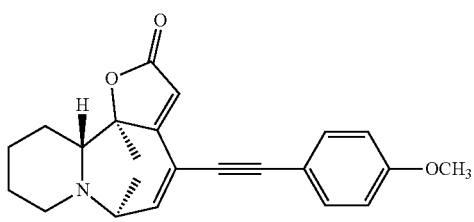 |
| INVS-MG-135B | 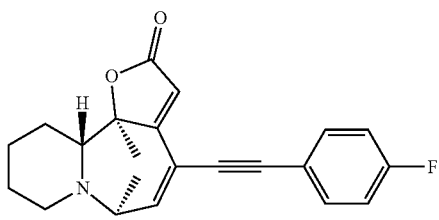 |
| INVS-MG-136B | 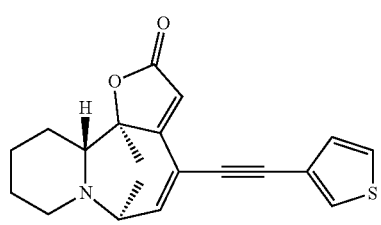 |

| Sample Code | Chemical Structure |
|---|---|
| INVS-MG-158B | 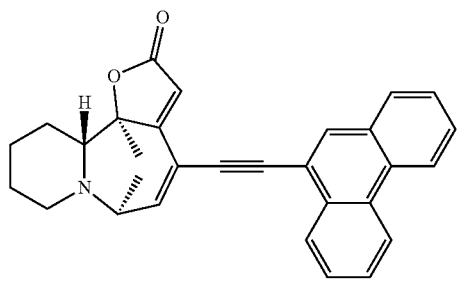 |
| INVS-MG-159A | 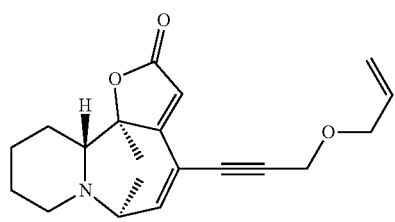 |
| INVS-MG-160B | 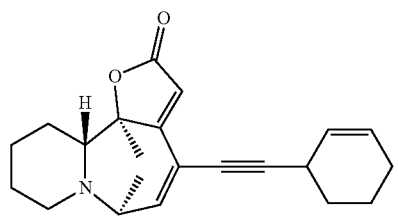 |
| INVS-MG-146-II | 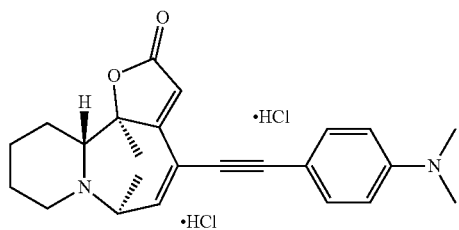 |
| INVS-MG-146B | 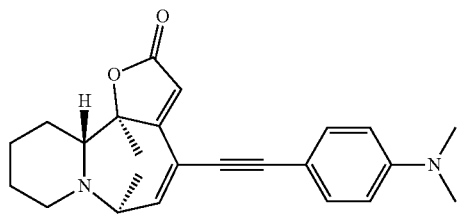 |
| INVS-MG-150B | 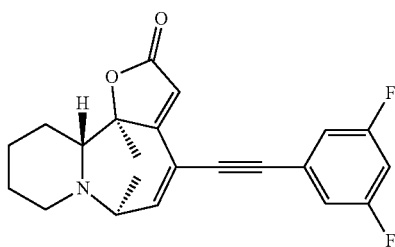 |

| Sample Code | Chemical Structure |
|---|---|
| INVS-MG-151B | 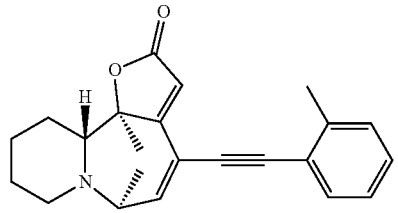 |
| INVS-MG-136B | 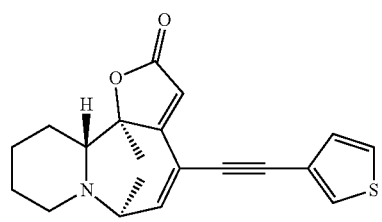 |
| INVS-MG-167B | 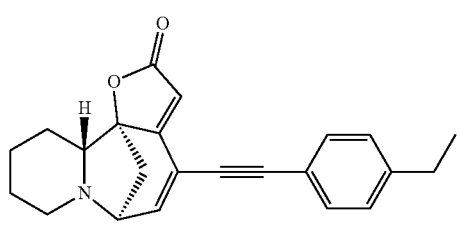 [SMILES: CCc1ccc(C#CC2=C[C@@H]3C[C@@]4(OC(=O)C=C24)[C@H]2CCCCN32)cc1] |
| INVS-MG-168B | 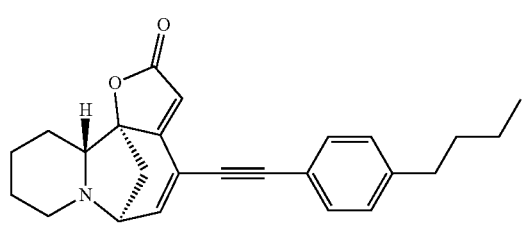 [SMILES: CCCCc1ccc(C#CC2=C[C@@H]3C[C@@]4(OC(=O)C=C24)[C@H]2CCCCN32)cc1] |
| INVS-MG-161B | 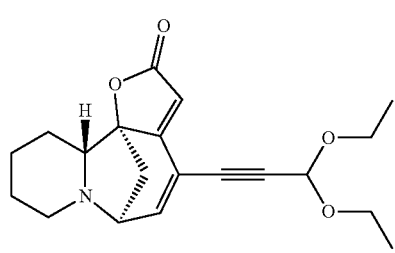 [SMILES: CCOC(C#CC1=C[C@@H]2C[C@@]3(OC(=O)C=C13)[C@H]1CCCCN21)OCC] |
| INVS-MG-162B | 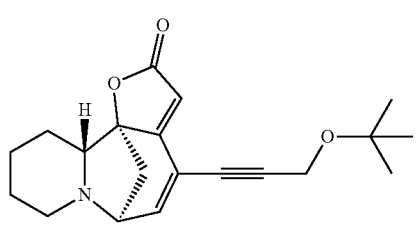 [SMILES: CC(C)(C)OCC#CC1=C[C@@H]2C[C@@]3(OC(=O)C=C13)[C@H]1CCCCN21] |

-continued

| Sample Code | Chemical Structure |
|---|---|
| INVS-MG-163-IIB | 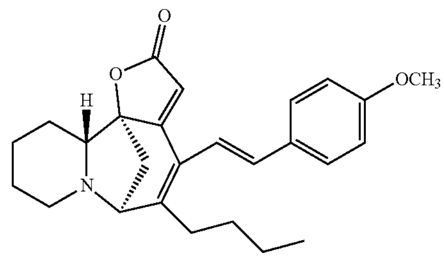 [SMILES: CCCCC1=C(/C=C/c2ccc(OC)cc2)C2=CC(=O)O[C@@]23C[C@@H]1N1CCCC[C@@H]13] |
| INVS-MG-164B | 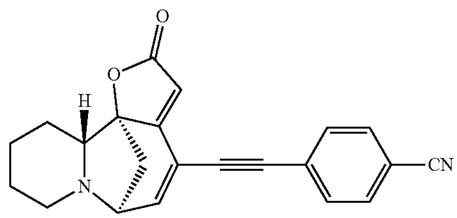 [SMILES: N#Cc1ccc(C#CC2=C[C@@H]3C[C@@]4(OC(=O)C=C24)[C@H]2CCCCN32)cc1] |
| INVS-MG-165B | 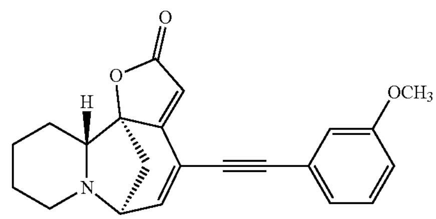 [SMILES: COc1cccc(C#CC2=C[C@@H]3C[C@@]4(OC(=O)C=C24)[C@H]2CCCCN32)c1] |
| INVS-MG-166B | 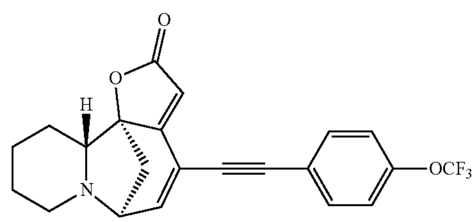 [SMILES: O=C1C=C2C(C#Cc3ccc(OC(F)(F)F)cc3)=C[C@@H]3C[C@@]2(O1)[C@H]1CCCCN31] |
| INVS-MG-169B | 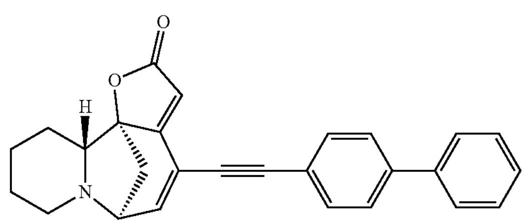 [SMILES: O=C1C=C2C(C#Cc3ccc(-c4ccccc4)cc3)=C[C@@H]3C[C@@]2(O1)[C@H]1CCCCN31] |
| INVS-MG-170B | 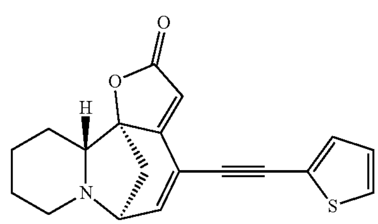 [SMILES: O=C1C=C2C(C#Cc3cccs3)=C[C@@H]3C[C@@]2(O1)[C@H]1CCCCN31] |
| INVS-MG-175A | 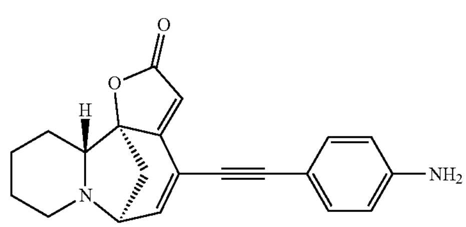 [SMILES: Nc1ccc(C#CC2=C[C@@H]3C[C@@]4(OC(=O)C=C24)[C@H]2CCCCN32)cc1] |

-continued
| Sample Code | Chemical Structure |
|---|---|
| INVS-MG-172C | 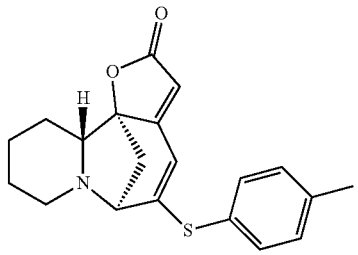 [SMILES: Cc1ccc(SC2=CC3=CC(=O)O[C@@]34C[C@@H]2N2CCCC[C@@H]24)cc1] |
| INVS-MG-184B | 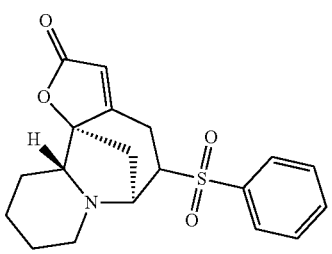 [SMILES: O=C1C=C2CC(S(=O)(=O)c3ccccc3)[C@@H]3C[C@@]2(O1)[C@H]1CCCCN31] |
| INVS-MG-146-IIIB | 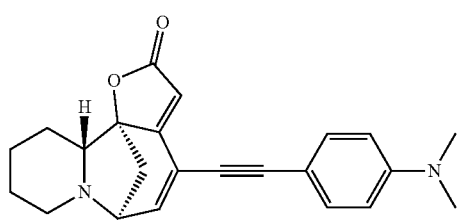 [SMILES: CN(C)c1ccc(C#CC2=C[C@@H]3C[C@@]4(OC(=O)C=C24)[C@H]2CCCCN32)cc1] |
| INVS-MG-149B | 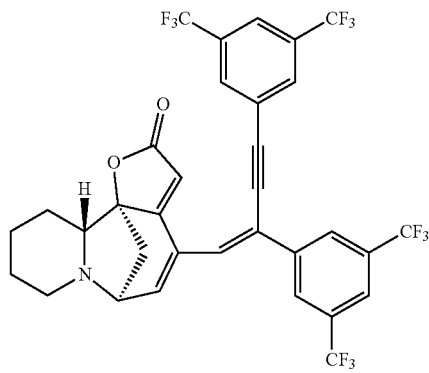 [SMILES: O=C1C=C2C(/C=C(\C#Cc3cc(C(F)(F)F)cc(C(F)(F)F)c3)c3cc(C(F)(F)F)cc(C(F)(F)F)c3)=C[C@@H]3C[C@@]2(O1)[C@H]1CCCCN31] |
| INVS-MG-149B' | 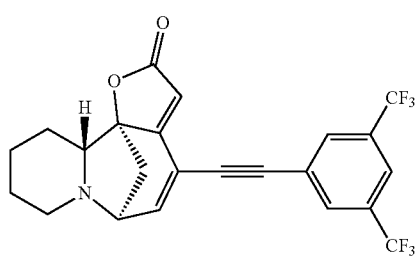 [SMILES: O=C1C=C2C(C#Cc3cc(C(F)(F)F)cc(C(F)(F)F)c3)=C[C@@H]3C[C@@]2(O1)[C@H]1CCCCN31] |
| INVS-MG-157-B | 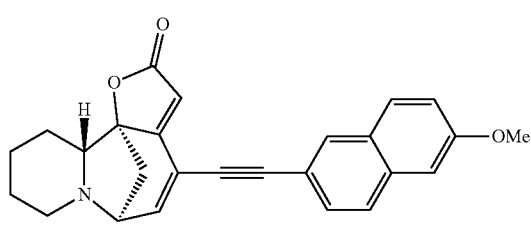 [SMILES: COc1ccc2cc(C#CC3=C[C@@H]4C[C@@]5(OC(=O)C=C35)[C@H]3CCCCN43)ccc2c1] |

-continued
| Sample Code | Chemical Structure |
|---|---|
| INVS-MG-152-IIB | 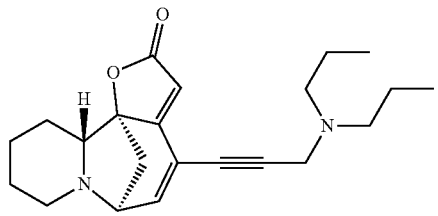 [SMILES: CCCN(CC#CC1=C[C@@H]2C[C@@]3(OC(=O)C=C13)[C@H]1CCCCN21)CCC] |
| INVS-MG-152-III | 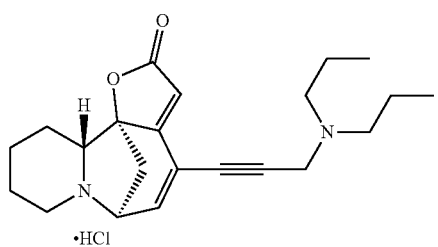 [SMILES: CCCN(CC#CC1=C[C@@H]2C[C@@]3(OC(=O)C=C13)[C@H]1CCCCN21)CCC ; Cl] |
| INVS-MG-157-IIB | 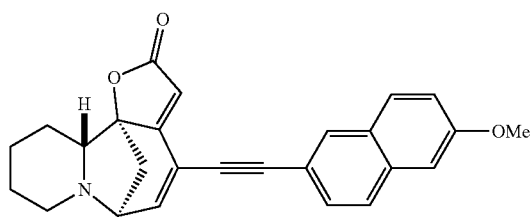 [SMILES: COc1ccc2cc(C#CC3=C[C@@H]4C[C@@]5(OC(=O)C=C35)[C@H]3CCCCN43)ccc2c1] |
| INVS-MG-157-III | 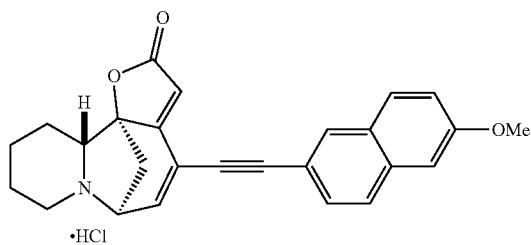 [SMILES: COc1ccc2cc(C#CC3=C[C@@H]4C[C@@]5(OC(=O)C=C35)[C@H]3CCCCN43)ccc2c1 ; Cl] |
| INVS-MG-158-IIB | 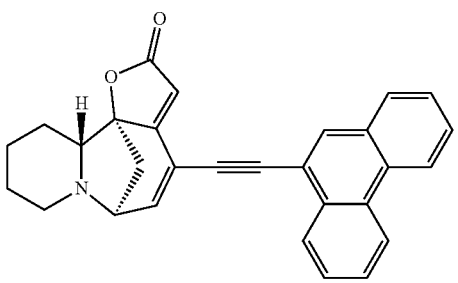 [SMILES: O=C1C=C2C(C#Cc3cc4ccccc4c4ccccc34)=C[C@@H]3C[C@@]2(O1)[C@H]1CCCCN31] |
| INVS-MG-158-III | 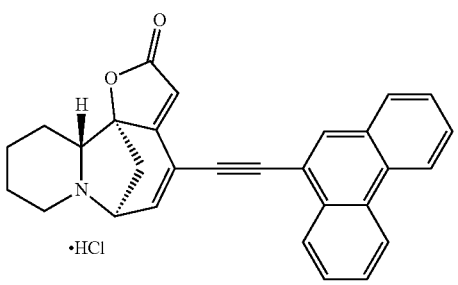 [SMILES: O=C1C=C2C(C#Cc3cc4ccccc4c4ccccc34)=C[C@@H]3C[C@@]2(O1)[C@H]1CCCCN31 ; Cl] |

-continued
| Sample Code | Chemical Structure |
|---|---|
| INVS-MG-169-IIB | 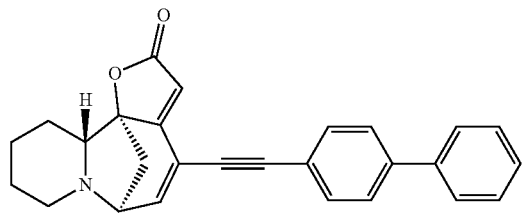 [SMILES: O=C1C=C2C(C#Cc3ccc(-c4ccccc4)cc3)=C[C@@H]3C[C@@]2(O1)[C@H]1CCCCN31] |
| INVS-MG-169-III | 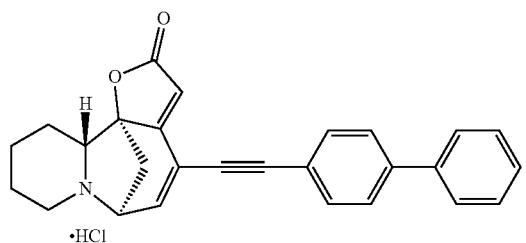 [SMILES: O=C1C=C2C(C#Cc3ccc(-c4ccccc4)cc3)=C[C@@H]3C[C@@]2(O1)[C@H]1CCCCN31 ; Cl] |
| INVS-MG-170-IIB | 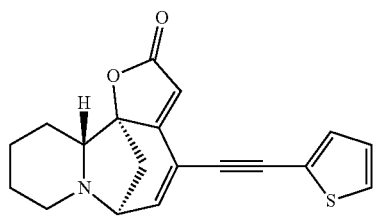 [SMILES: O=C1C=C2C(C#Cc3cccs3)=C[C@@H]3C[C@@]2(O1)[C@H]1CCCCN31] |
| INVS-MG-170-III | 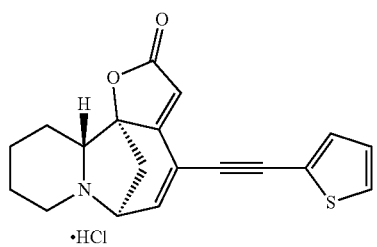 [SMILES: O=C1C=C2C(C#Cc3cccs3)=C[C@@H]3C[C@@]2(O1)[C@H]1CCCCN31 ; Cl] |
| INVS-MG-175-V | 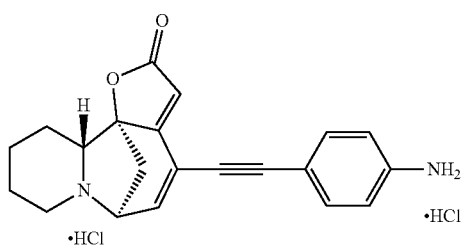 [SMILES: Nc1ccc(C#CC2=C[C@@H]3C[C@@]4(OC(=O)C=C24)[C@H]2CCCCN32)cc1 ; Cl ; Cl] |
| INVS-MG-193B | 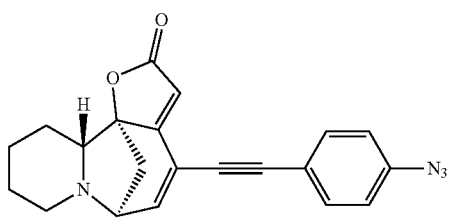 [SMILES: [N-]=[N+]=Nc1ccc(C#CC2=C[C@@H]3C[C@@]4(OC(=O)C=C24)[C@H]2CCCCN32)cc1] |

-continued
| Sample Code | Chemical Structure |
|---|---|
| INVS-MG-193-III | 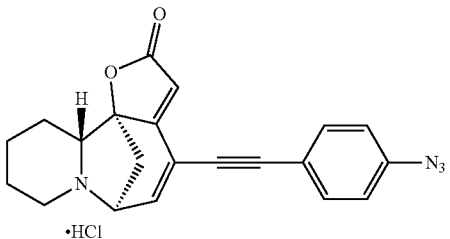 [SMILES: [N-]=[N+]=Nc1ccc(C#CC2=C[C@@H]3C[C@@]4(OC(=O)C=C24)[C@H]2CCCCN32)cc1 ; Cl] |
| INVS-MG-176B | 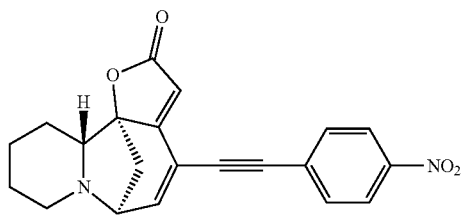 [SMILES: O=C1C=C2C(C#Cc3ccc([N+](=O)[O-])cc3)=C[C@@H]3C[C@@]2(O1)[C@H]1CCCCN31] |
| INVS-MG-176-II | 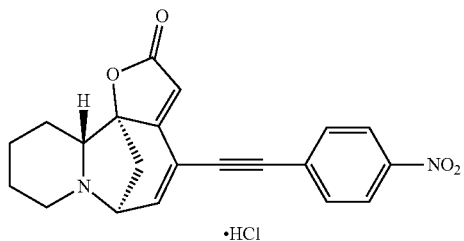 [SMILES: O=C1C=C2C(C#Cc3ccc([N+](=O)[O-])cc3)=C[C@@H]3C[C@@]2(O1)[C@H]1CCCCN31 ; Cl] |
| INVS-MG-179B | 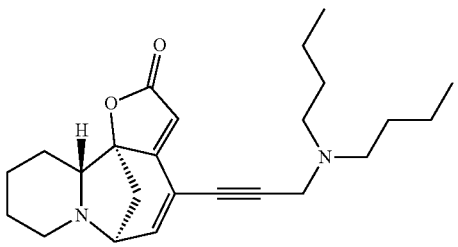 [SMILES: CCCCN(CC#CC1=C[C@@H]2C[C@@]3(OC(=O)C=C13)[C@H]1CCCCN21)CCCC] |
| INVS-MG-179-II | 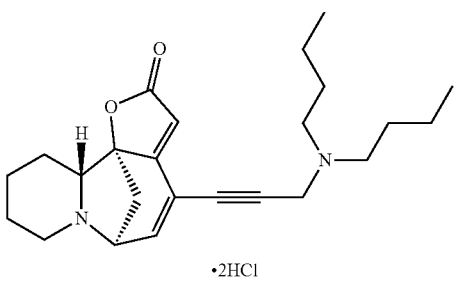 [SMILES: CCCCN(CC#CC1=C[C@@H]2C[C@@]3(OC(=O)C=C13)[C@H]1CCCCN21)CCCC] |
| INVS-MG-145-IIIA | 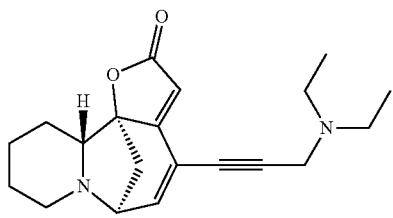 [SMILES: CCN(CC)CC#CC1=C[C@@H]2C[C@@]3(OC(=O)C=C13)[C@H]1CCCCN21] |

-continued
| Sample Code | Chemical Structure |
|---|---|
| INVS-MG-145-V | 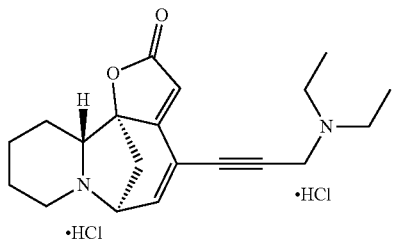 [SMILES: CCN(CC)CC#CC1=C[C@@H]2C[C@@]3(OC(=O)C=C13)[C@H]1CCCCN21 ; Cl ; Cl] |
| INVS-MG-158-IVC | 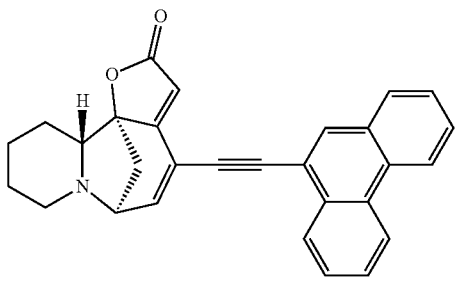 [SMILES: O=C1C=C2C(C#Cc3cc4ccccc4c4ccccc34)=C[C@@H]3C[C@@]2(O1)[C@H]1CCCCN31] |
| INVS-MG-158-V | 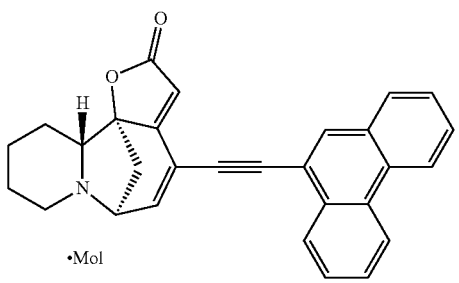 [SMILES: O=C1C=C2C(C#Cc3cc4ccccc4c4ccccc34)=C[C@@H]3C[C@@]2(O1)[C@H]1CCCCN31] |
| INVS-MG-158-VI | 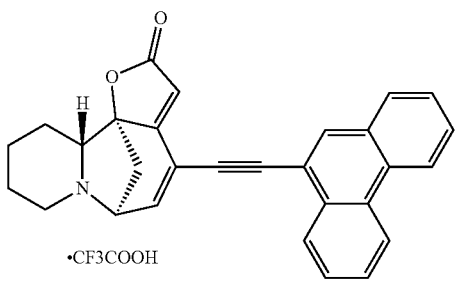 [SMILES: O=C1C=C2C(C#Cc3cc4ccccc4c4ccccc34)=C[C@@H]3C[C@@]2(O1)[C@H]1CCCCN31] |
| INVS-MG-165-IIB | 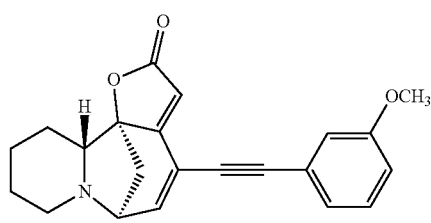 [SMILES: COc1cccc(C#CC2=C[C@@H]3C[C@@]4(OC(=O)C=C24)[C@H]2CCCCN32)c1] |
| INVS-MG-165-III | 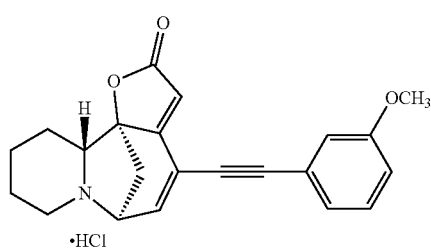 [SMILES: COc1cccc(C#CC2=C[C@@H]3C[C@@]4(OC(=O)C=C24)[C@H]2CCCCN32)c1 ; Cl] |

-continued
| Sample Code | Chemical Structure |
|---|---|
| INVS-MG-207A | 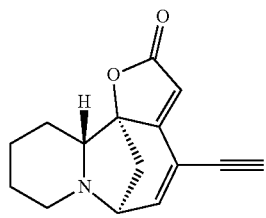 [SMILES: C#CC1=C[C@@H]2C[C@@]3(OC(=O)C=C13)[C@H]1CCCCN21] |
| INVS-MG-207-II | 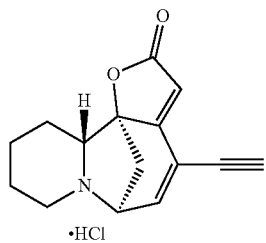 [SMILES: C#CC1=C[C@@H]2C[C@@]3(OC(=O)C=C13)[C@H]1CCCCN21 ; Cl] |
| INVS-MG-207-IIIA | 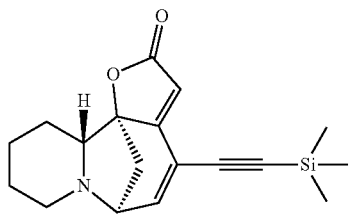 [SMILES: C[Si](C)(C)C#CC1=C[C@@H]2C[C@@]3(OC(=O)C=C13)[C@H]1CCCCN21] |
| INVS-MG-224A | 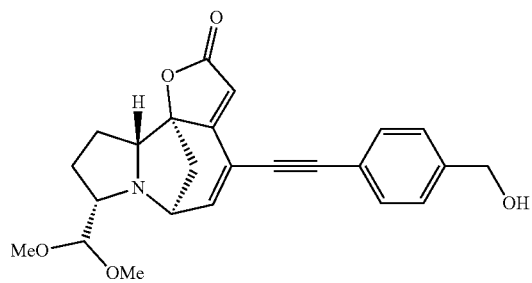 [SMILES: COC(OC)[C@@H]1CC[C@H]2N1[C@@H]1C=C(C#Cc3ccc(CO)cc3)C3=CC(=O)O[C@@]32C1] |
| INVS-MG-222-III | 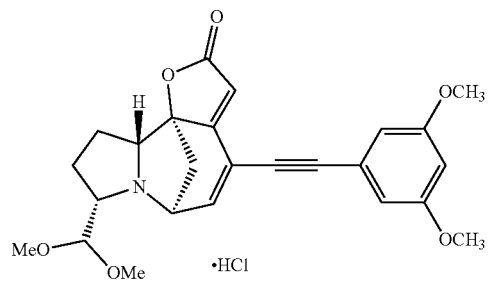 [SMILES: COc1cc(C#CC2=C[C@@H]3C[C@@]4(OC(=O)C=C24)[C@H]2CC[C@@H](C(OC)OC)N32)cc(OC)c1 ; Cl] |
| INVS-MG-184-IIB | 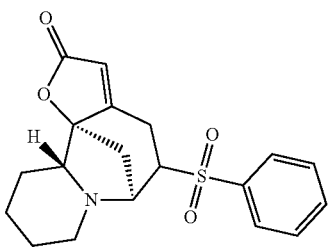 [SMILES: O=C1C=C2CC(S(=O)(=O)c3ccccc3)[C@@H]3C[C@@]2(O1)[C@H]1CCCCN31] |

-continued

| Sample Code | Chemical Structure |
|---|---|
| INVS-MG-209A | 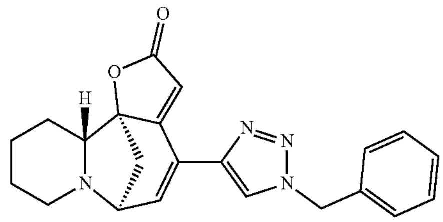 [SMILES: O=C1C=C2C(c3cn(Cc4ccccc4)nn3)=C[C@@H]3C[C@@]2(O1)[C@H]1CCCCN31] |
| INVS-MG-99-IVB | 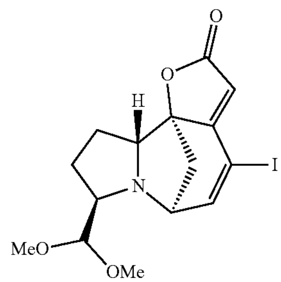 [SMILES: COC(OC)[C@H]1CC[C@H]2N1[C@@H]1C=C(I)C3=CC(=O)O[C@@]32C1] |
| INV-SZ-117-3 | 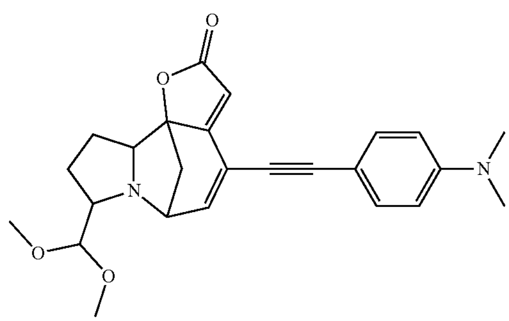 |
| INV-117-4 | 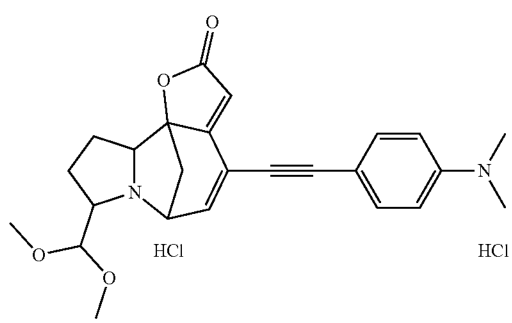 |
| INV-SZ-118-2 | 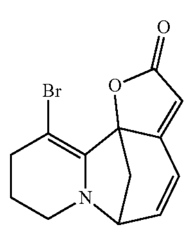 [SMILES: O=C1C=C2C=CC3CC2(O1)C1=C(Br)CCCN13] |
| INV-SZ-120-1 | 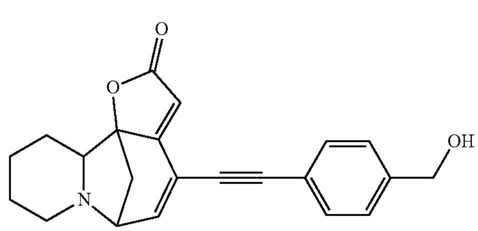 [SMILES: O=C1C=C2C(C#Cc3ccc(CO)cc3)=CC3CC2(O1)C1CCCCN31] |

-continued
| Sample Code | Chemical Structure |
|---|---|
| INV-SZ-121-1 | 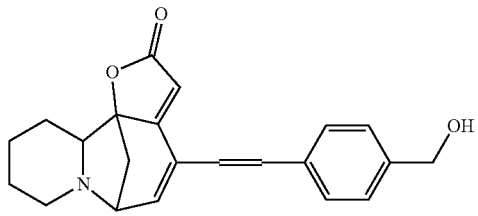 [SMILES: O=C1C=C2C(C=Cc3ccc(CO)cc3)=CC3CC2(O1)C1CCCCN31] |
| INV-SZ-122-1 | 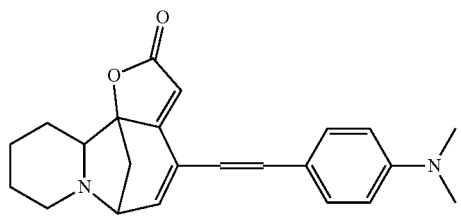 [SMILES: CN(C)c1ccc(C=CC2=CC3CC4(OC(=O)C=C24)C2CCCCN32)cc1] |
| INVS-MG-99-IVD | 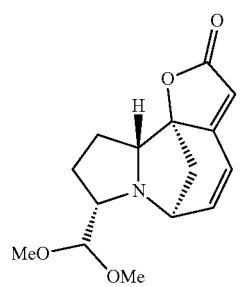 [SMILES: COC(OC)[C@@H]1CC[C@H]2N1[C@@H]1C=CC3=CC(=O)O[C@@]32C1] |
| INVS-MG-99-IVD-I | 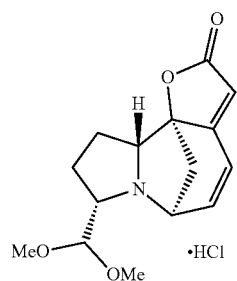 [SMILES: COC(OC)[C@@H]1CC[C@H]2N1[C@@H]1C=CC3=CC(=O)O[C@@]32C1 ; Cl] |
| INVS-MG-219A | 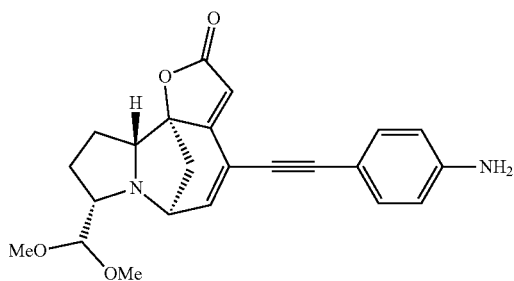 [SMILES: COC(OC)[C@@H]1CC[C@H]2N1[C@@H]1C=C(C#Cc3ccc(N)cc3)C3=CC(=O)O[C@@]32C1] |

| Sample Code | Chemical Structure |
|---|---|
| INVS-MG-220B | 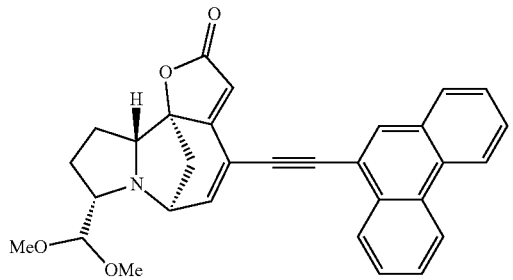 [SMILES: COC(OC)[C@@H]1CC[C@H]2N1[C@@H]1C=C(C#Cc3cc4ccccc4c4ccccc34)C3=CC(=O)O[C@@]32C1] |
| INVS-MG-220C | 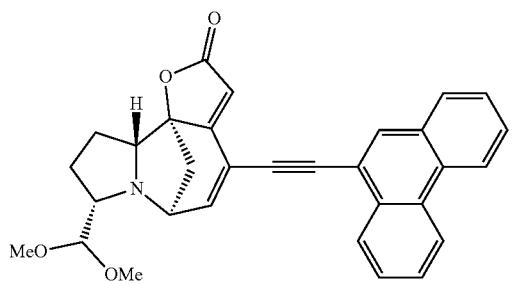<br>str?? aromatic disturbed |
| INVS-MG-221B | 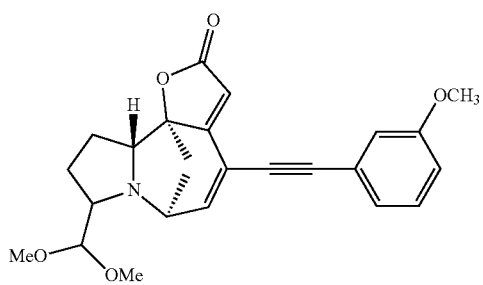 |
| INVS-MG-222B | 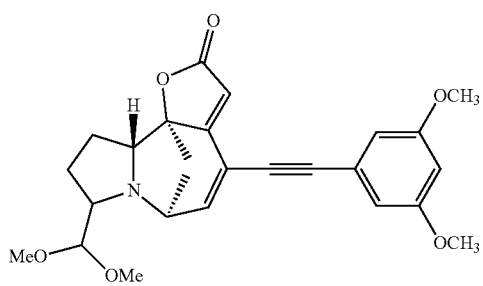 |
| INVS-MG-223B | 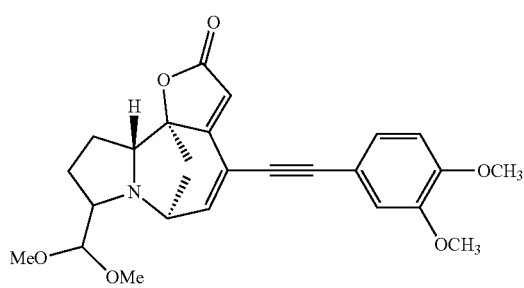 |

-continued
| Sample Code | Chemical Structure |
|---|---|
| INV-SZ-125-3 | 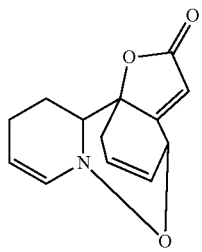 [SMILES: O=C1C=C2C3C=CCC2(O1)C1CCC=CN1O3] |
| INV-SZ-125-2 | 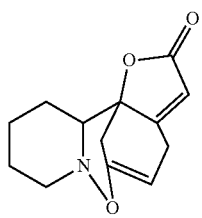 [SMILES: O=C1C=C2CC=C3CC2(O1)C1CCCCN1O3] |
| INV-SZ-125-1 | 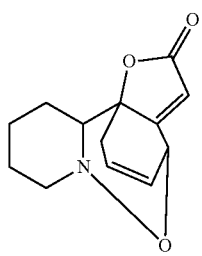 [SMILES: O=C1C=C2C3C=CCC2(O1)C1CCCCN1O3] |
| INV-SZ-127-1 | 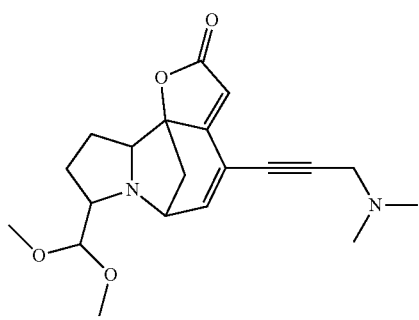 |
| INV-SZ-129-1 | 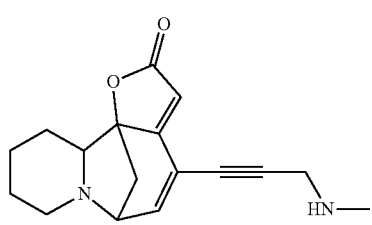 [SMILES: CNCC#CC1=CC2CC3(OC(=O)C=C13)C1CCCCN21] |

-continued
| Sample Code | Chemical Structure |
|---|---|
| INV-SZ-134-1 | 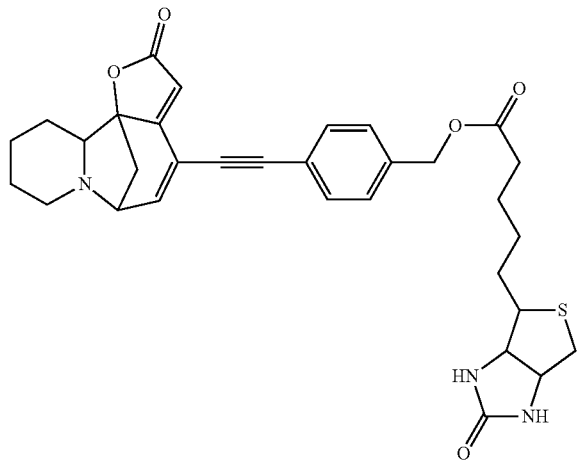 [SMILES: O=C1NC2CSC(CCCCC(=O)OCc3ccc(C#CC4=CC5CC6(OC(=O)C=C46)C4CCCCN54)cc3)C2N1] |
| INV-SZ-113-2 | 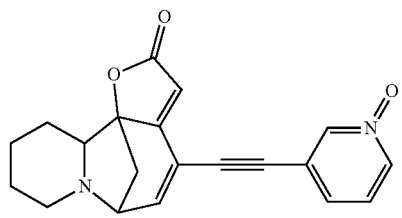 [SMILES: O=C1C=C2C(C#Cc3ccc[n+]([O-])c3)=CC3CC2(O1)C1CCCCN31] |
| INV-SZ-114-1 | 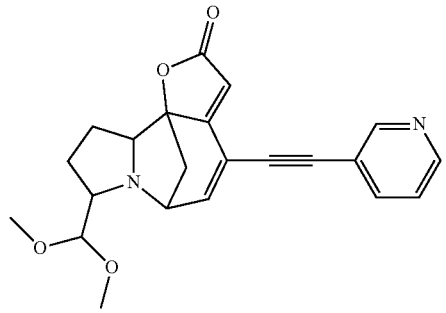 [SMILES: COC(OC)C1CCC2N1C1C=C(C#Cc3cccnc3)C3=CC(=O)OC32C1] |
| INV-SZ-115-1 | 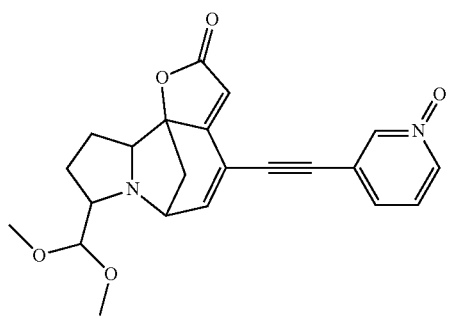 [SMILES: COC(OC)C1CCC2N1C1C=C(C#Cc3ccc[n+]([O-])c3)C3=CC(=O)OC32C1] |
| INV-SZ-116-1 | 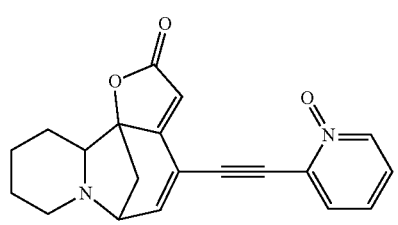 [SMILES: O=C1C=C2C(C#Cc3cccc[n+]3[O-])=CC3CC2(O1)C1CCCCN31] |

-continued
| Sample Code | Chemical Structure |
|---|---|
| INV-SZ-133-1 | 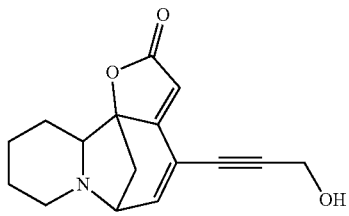 [SMILES: O=C1C=C2C(C#CCO)=CC3CC2(O1)C1CCCCN31] |
| INVS-MG-111B | 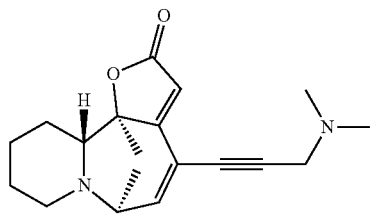 |
| INVS-MG-136-III | 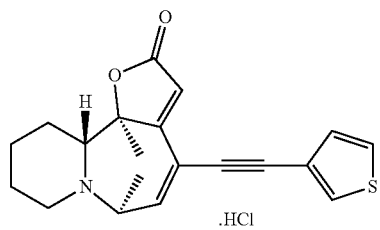 |
| INV-SZ-123-2 | 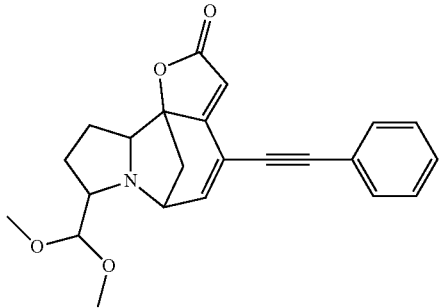 [SMILES: COC(OC)C1CCC2N1C1C=C(C#Cc3ccccc3)C3=CC(=O)OC32C1] |
| INV-SZ-123-3 | 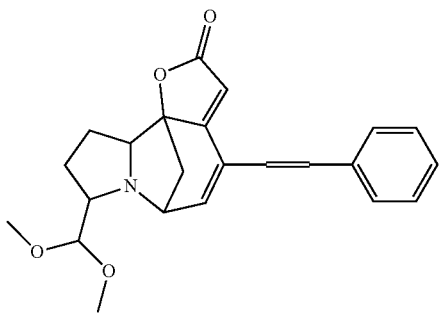 [SMILES: COC(OC)C1CCC2N1C1C=C(C=Cc3ccccc3)C3=CC(=O)OC32C1] |

-continued
| Sample Code | Chemical Structure |
|---|---|
| INV-SZ-136-1 | 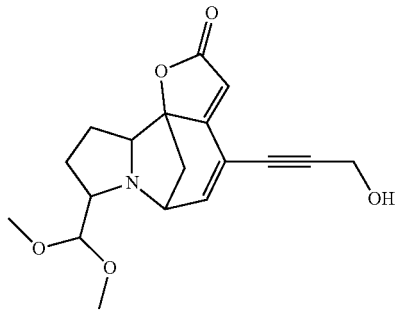 [SMILES: COC(OC)C1CCC2N1C1C=C(C#CCO)C3=CC(=O)OC32C1] |
| INV-SZ-137-1 | 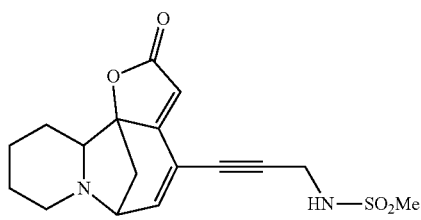 [SMILES: CS(=O)(=O)NCC#CC1=CC2CC3(OC(=O)C=C13)C1CCCCN21] |
| INV-SZ-138-2 | 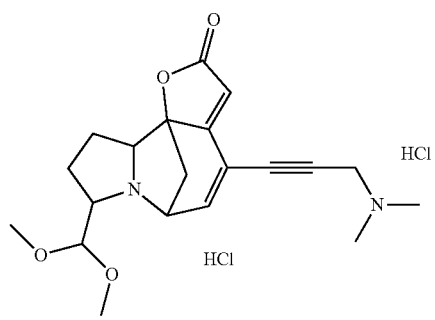 |
| INVS-MG-145A | 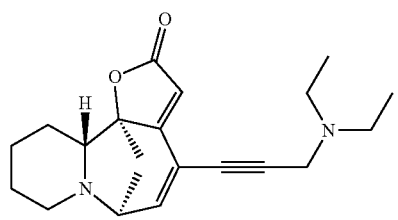 |
| INVS-MG-146-II | 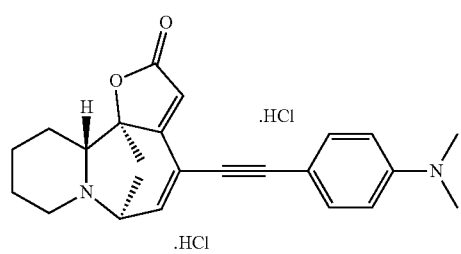 |

-continued
| Sample Code | Chemical Structure |
|---|---|
| INV-SZ-140-1 | 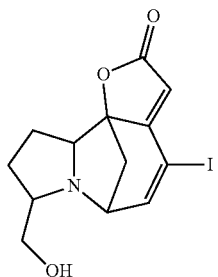 [SMILES: O=C1C=C2C(I)=CC3CC2(O1)C1CCC(CO)N31] |
| INV-SZ-132-1 | 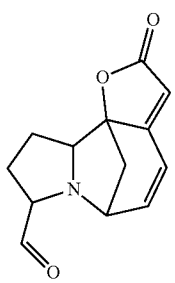 [SMILES: O=CC1CCC2N1C1C=CC3=CC(=O)OC32C1] |
| INV-SZ-141-1 | 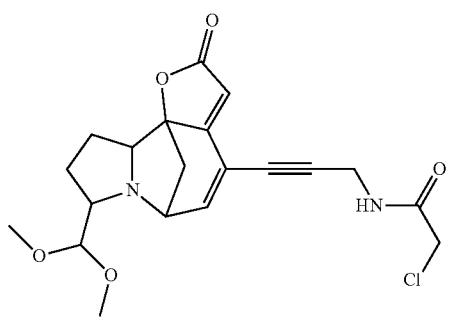 [SMILES: COC(OC)C1CCC2N1C1C=C(C#CCNC(=O)CCl)C3=CC(=O)OC32C1] |
| INVS-MG-184-III | 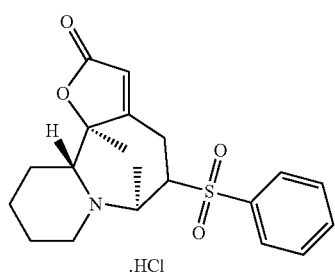<br>.HCl |
| INV-SZ-122-1 | 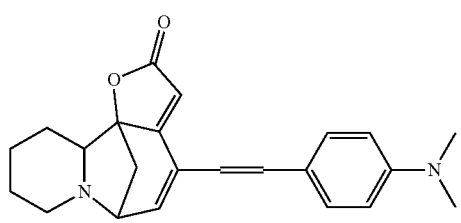 [SMILES: CN(C)c1ccc(C=CC2=CC3CC4(OC(=O)C=C24)C2CCCCN32)cc1] |
| INVS-MG-144B | 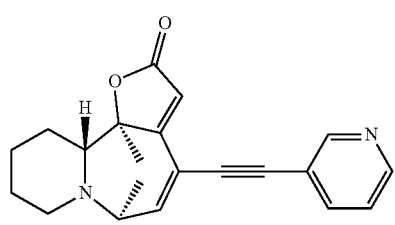 |

| Sample Code | Chemical Structure |
|---|---|
| INVS-MG-99-IVB-I | 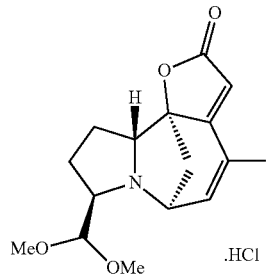 |

The present invention provides for methods of treating inflammatory or immune disorders in a subject comprising contacting a subject with the securinine and/or nor securinine analogs described herein. The analogs of the present invention have demonstrated themselves to be efficacious in treating generated oxidative molecules. The enzyme myeloperoxidase (MPO) is a lysosomal enzyme neutrophils use to kill microbes by generating the potent oxidant, hypochlorous acid, which is heavily expressed in primary (azurophilic) granules of neutrophils. Myeloperoxidase is important in bacterial killing, but also drives inflammatory reactions and tissue oxidation. MPO, a member of the haem peroxidase-cyclooxygenase superfamily, is abundantly expressed in neutrophils and to a lesser extent in monocytes and certain type of macrophages. Numerous lines of evidence implicate a role for MPO in the pathogenesis of various diseases (see, e.g., Lin et al. *Leukemia* (2002) 16:1143-1153). MPO is present in wide varieties of tissue, such as connective, muscle, epithelial and nervous, however their pathogenic roles may differ depending on the types and stages of diseases. A unique activity of MPO is its ability to use chloride as a co-substrate with hydrogen peroxide to generate chlorinating oxidants such as hypochlorous acid, a potent antimicrobial agent. MPO-derived oxidants contribute to tissue damage and the initiation and propagation of acute and chronic vascular inflammatory disease. Circulating levels of MPO have been shown to predict risks for major adverse cardiac events and levels of MPO-derived chlorinated compounds are specific biomarkers for disease progression.

The present invention provides for securinine and norsecurinine analogs that inhibit persistent MPO activation by binding MPO directly and inhibiting the enzymatic activity. Increased systemic levels of MPO and its oxidation products predict increased risk factors for disease like COPD, cardiovascular disease, lung cancer, etc. As set forth in the examples herein, administering or contacting MPO with the securinine and norsecurinine analogs described herein provide efficacious enzymatic inhibitors as demonstrated in the results presented in Table 1.

The present invention provides methods for altering myeloperoxidase activity by administering one or more of the securinine and/or norsecurinine analogs described herein to a myeloperoxidase enzyme, either in vitro or in vivo or ex vivo. As demonstrated herein, administration and/or contacting myeloperoxidase enzymes with securinine and/or norsecurinine analogs described herein produced inhibited activity. Those skilled in the art will appreciate that combining the securinine and/or norsecurinine analogs with other immuno-effective agents, such as non-steroidal anti-inflammatory agents (NSAIDs), cyclooxygenase I and II inhibitors, steroids, corticosteroids, glucocorticosteroids, interferon inhibitors, gold, salicylic acid, naproxen, ibuprofen, acetaminophen, immune selective anti-inflammatories (ImSAIDs), disease modifying anti-rheumatic agents (DMARDs), methotrexate, salsalate, celecoxib, diclofenac, etodac, indomethacin, ketoprofen, nabumetone, oxaprozin, piroxicam, sulindac, tolmetin, prostaglandin modulators, as well as antibody derived agents.

The present invention provides for methods of inhibiting enzymatic activity of MPO. As described herein, the securinine and/or norsecurinine analogs directly bind to a myeloperoxidase enzyme. The binding site of the analogs allows for the analogs to further affect enzymatic activity. The bound analogs may inhibit the enzymatic activity of MPO by 5, 10, 15, 20, 25, 30, 35, 40, 45, 50, 55, 60, 65, 70, 75, 80, 85, 90, 95, 96, 97, 98, 99 or 100%, or values therewithin. The bound analog may inhibit the chlorination activity. The bound analog may not affect the peroxidation activity or may inhibit peroxidation activity to lesser extent than inhibiting chlorination activity.

The present invention also provides methods for inhibiting a myeloperoxidase enzyme either within a cell or exterior thereto, such as within a cell of an immune system or released by the cell, by administering to the cell or surrounding environment thereof the securinine and/or norsecurinine analogs of the present invention. As described in the examples, the securinine and/or norsecurinine analogs are potent inhibitors of the MPO enzyme, particularly with respect to chlorination activity. The examples presented here demonstrate direct binding by the securinine and/or norsecurinine analogs with MPO. The heme 'm' in myeloperoxidase contains two ester bonds at the heme 1 and 5-methyls and a sulfonium ion linkage is also observed. Securinine and/or norsecurinine analogs, such as securinine and 184B, dock closer to the porphyrin on the left to this sulfonium-forming a porphyrin group. Inhibition of the myeloperoxidase occurs when such covalent links are formed. Those skilled in the art will appreciate that administering securinine and/or norsecurinine analogs of the present invention is beneficial to conditions adversely associated with MPO activity, such as COPD, atherosclerosis, myocardial infarction, cardiovascular disease, and hypertension. MPO is also associated underlying conditions, such as organ failure, viral/bacterial/fungal/pathogen/parasite infection, cancer and heart disease. Those skilled in the art will appreciate that the securinine and/or norsecurinine analogs can be added to any existing therapeutic regimen in order to introduce the added benefit of reducing damage inflicted by MPO within the subject.

The present invention also provides for treating active MPO and prophylactic treatment to MPO activity. Those skilled in the art will appreciate that administration of the analogs to a subject provides for both inhibiting active MPO, as well as inactive MPO, such as that is yet to be released by a neutrophil. Administering the analogs of the present invention to a subject in need thereof, or in suspected need thereof, provides for inhibiting MPO prior to the molecule's release and activity. Those skilled in the art will appreciate that administering the analogs to a subject in advance or subsequent to an inflammatory stimulating event provides for reduced and/inhibited MPO activity with the subject.

The present invention provides methods for preventing, treating or reducing enzymatic damage to a cell by administering the securinine and/or norsecurinine analogs of the present invention to a cell attacked by free radicals. As described herein, the analogs of the present invention inhibit the enzymatic activity of MPO. By contacting a MPO molecule with the analogs of the present invention, the MPO's ability to produce detrimental radicals is reduced, and as such, damage to the cell is stopped or reduced. The cell may be in vitro or in vivo, such as within the body of a subject. The cell may be part of a tissue. The cell may be part of an organ, such as the lungs, kidney, liver, intestine, brain, skin, gall bladder, circulatory system, heart, eye, testes, ovaries, bladder, prostate, colon or lymph. The cell may be within an organ system, such as the circulatory system, digestive system, cardiovascular system, immune system, lymphatic system, skeletal system, reproductive system, urinary system, endocrine system, respiratory system, muscular system or nervous system.

The present invention provides for methods of ameliorating inflammation and free radical damage from MPO activity by contacting an MPO enzyme with a securinine and/or norsecurinine analog as described herein. MPO activity may be associated with an underlying condition, such as an infection or an immune response or a disease. Increased MPO activity may be a side effect or a secondary effect from an underlying trigger, such as a disease or other administered agent. Those skilled in the art will appreciate that the direct binding and subsequent inhibition of MPO activity can be within a cell or with released MPO enzymes and that the analogs can function as scavengers for MPO throughout a subject. The securinine and/or norsecurinine analogs may be combined with other therapeutic agents to improve overall efficacy or to nullify secondary effects caused from other administered agents (see, e.g., Physicians' desk reference. (68th ed.). (2014). Montvale, N.J.: PDR Network). For example, cardiovascular diseases are associated with myeloperoxidase activity and adding a securinine and/or norsecurinine analog to a therapeutic regimen can provide the desired reduction in MPO activity. The present invention also provides for methods of combination therapy for the treatment by combining the securinine or norsecurinine analogs describes herein with a known anti-inflammatory or known immunomodulating agent. Those skilled in the art will appreciate that the securinine and/or norsecurinine analogs described herein can be used in combination with each other.

The present invention also provides for using pharmaceutical compositions comprising the securinine and/or norsecurinine compounds described herein. The pharmaceutical compositions comprise at least one securinine or norsecurinine derivative as described herein or a salt thereof and a pharmaceutically acceptable carrier, which are known in the art. Pharmaceutically acceptable carriers include diluents, fillers, salts, buffers, stabilizers, solubilizers and other materials that are well-known in the art and may routinely comprise salt, buffering agents, preservatives, compatible carriers, and optionally other therapeutic agents. Those skilled in the art will understand that intermediate non-pharmaceutically acceptable salts may be used to prepare pharmaceutically-acceptable salts thereof and are not to be considered excluded from the scope of the invention. Pharmaceutically acceptable salts may include, but are not limited to, those prepared from the following acids: hydrochloric, hydrobromic, sulfuric, nitric, phosphoric, maleic, acetic, salicylic, citric, formic, malonic, succinic, and the like. Similarly, pharmaceutically-acceptable salts can be prepared as alkaline metal or alkaline earth salts, such as sodium, potassium or calcium salts.

The methods of the present invention provide for use of the securinine and/or norsecurinine analogs described herein which may be formulated into preparations in solid, semi-solid, liquid or gaseous forms such as tablets, capsules, powders, granules, ointments, solutions, depositories, inhalants and injections, and usual ways for oral, parenteral, intravenal, intragastric, rectal, Intraperitoneal, intraarterial, subcutaneous, intravascular, topical, ocular, intranasal, intratracheal, intracranial, intramuscular, intracardiac, intrathoracic, intracranial, or surgical administration. As may be evident, the securinine and norsecurinine compounds described herein may further be derived into a prodrug which, as is known in the art, involves covalently attaching a further group, such as a protecting group, to the compound that will be removed by the subject's own biology, such as through metabolizing the compound (e.g. by cytochrome p450 or other enzymatic reactions), enzymatic degradation, or through changes in surrounding pH or ionic environment or temperature (see, e.g. epharmacology.hubpages.com/hub/Pharmacological-Effects-Prodrugs-Definition-Examples-and-Sources-of-Drug-Information). Prodrugs may improve the administration, distribution, metabolism and/or excretion of the compound. Prodrugs may improve the half life of administered analogs, increase the therapeutic index or alter the effective dose (e.g., ED50).

The securinine and/or norsecurinine analogs may contact MPO after being administered to a cell or in proximity to a cell, such as a cell of an organism in vivo or isolated from an organism in vitro or ex vivo. The cell may be part of an organ, such as the lungs, kidney, liver, intestine, brain, skin, gall bladder, circulatory system, heart, eye, testes, ovaries, bladder, prostate, colon or lymph. The cell may be within an organ system, such as the circulatory system, digestive system, cardiovascular system, immune system, lymphatic system, skeletal system, reproductive system, urinary system, endocrine system, respiratory system, muscular system or nervous system.

The securinine analogs may be administered or be caused to come into contact with a MPO molecule and alter the resulting function within the cell or proximal to a cell, such as by altering catalytic activity (e.g. blocking activating molecule access or blocking access/activity of a catalytic domain) or inhibiting an active site on the small molecule, such as a catalytic domain or a binding site for another interacting molecule. The cell may be isolated or be part of an organism, such as a eukaryote. The cell may be subject to damage by free radicals or reactive oxygen species (ROS). The cell may be a diseased or malfunctioning cell, e.g. cells wherein undesired genes and proteins are being expressed. The cell may be an abnormally arrested cell, such that it is unable to properly mature. The analogs may bind to the MPO molecule reversibly or irreversibly and those skilled in the art will appreciate that different analogs will have easily identifiable and quantifiable binding affinities.

The methods of the present invention comprise selecting a cell or a subject in known or suspected need of treatment with the securinine and norsecurinine analogs described herein. For example, as set forth in the Examples below, securinine and norsecurinine analogs have demonstrated efficacy in treating or ameliorating various conditions, such as oxidation, chlorination, inflammation, immune system modulation, myeloid disorders or enzyme catalytic action. The cell or subject may be selected by assaying for a suspected complication. A subject may be selected following a diagnosis of a physician upon analysis of the subject's symptoms and overall physiology. A cell may be selected based upon phenotype or known/identified classification. The subject may be an animal, such as a mammal, reptile, amphibian, bird or fish, or a plant. The subject may be a mammal, such as human, bovine, canine, feline, porcine, equine, murine, marsupial, ovine or related mammal. Cells or subjects appropriate for treatment can be determined with assays known in the art. For example, biomarkers, such as overexpressed or underexpressed proteins, deformed genes, or mutant post-translationally modified proteins can be detected by various mechanisms known in the art, such as chromatography, blotting, NMR, HPLC, ELISA, LC-MS/MS, and so forth. Following detection, further analysis may be performed as needed to confirm or refute the underlying condition.

The present invention further provides for methods of determining the activity and/or abundance of MPO. As is known in the art, increased levels of MPO are associated with many diseases and can also aggravate acute and/or chronic conditions. The securinine and/or norsecurinine analogs of the present invention bind to and inhibit MPO. Contacting the analogs of the present invention with a sample taken from a subject, or administering the analogs to the subject provide for a method to determine the amount of MPO. Those skilled in the art will appreciate that a labeling or a secondary labeling of the analogs, such as with a fluorophore, radioisotope, or other recognized label, allows for quantification of the amount of MPO with a sample or subject.

EXAMPLES

Synthesis of Non-Reduced Analogs

In another variation, γ-iodo derivative of securinine (C14-iodo derivative of securinine, INVS-MG-52A) can be prepared from securinine using N-iodosuccinimide in MeOH (Reported, *Tetrahedron* 2012, 68, 3972-3979). During the product isolation from the reaction mixture, side products INVS-MG-52B and INVS-MG-52D also isolated. Using the intermediates INVS-MG-52A and -52B, further C-14 analogs of securinine can be prepared as outlined below.

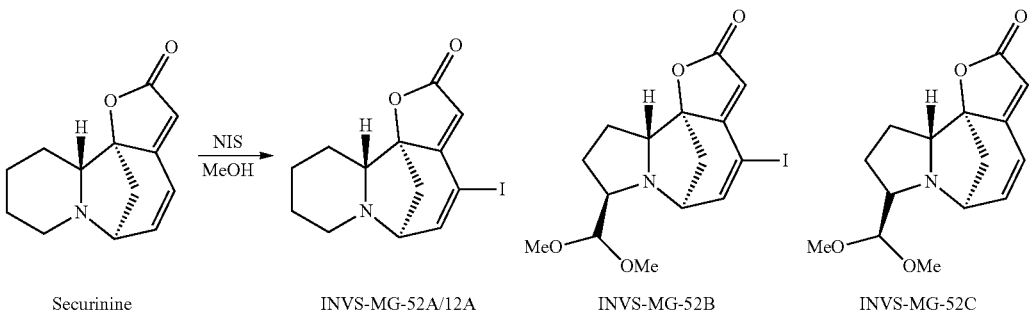

Securinine     INVS-MG-52A/12A     INVS-MG-52B     INVS-MG-52C

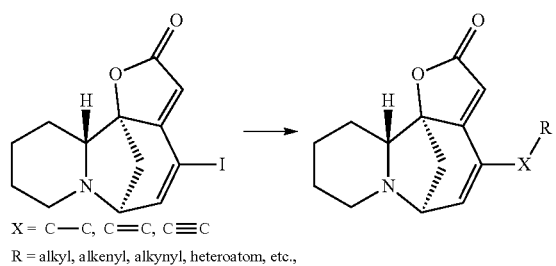

X = C—C, C=C, C≡C
R = alkyl, alkenyl, alkynyl, heteroatom, etc.,

In one variation, the process comprising the synthesis of C-14 alkyl/aryl analogs of securinine can be prepared using INVS-MG-52A and the corresponding boronic acids/esters as outlined below.

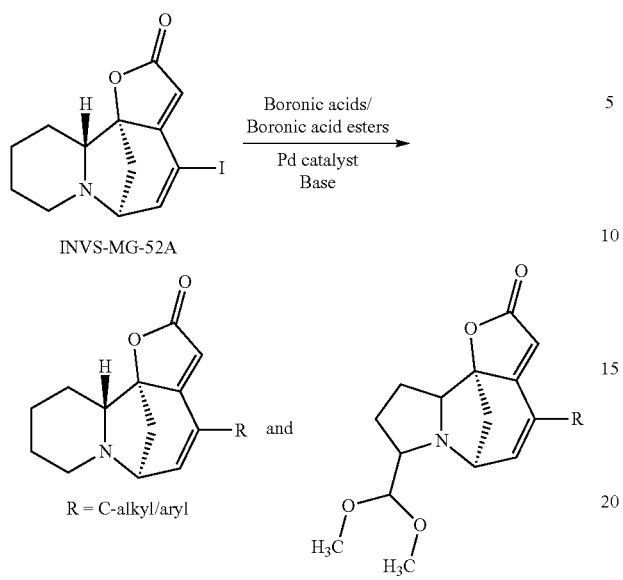

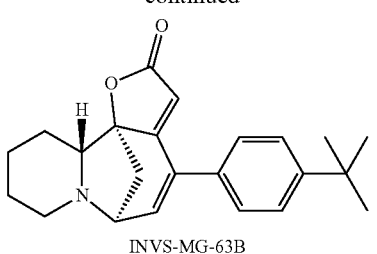

INVS-MG-63B

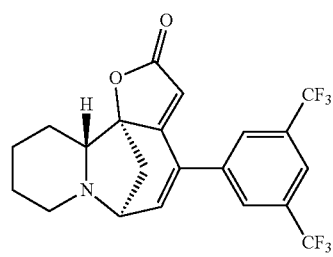

INVS-MG-64A

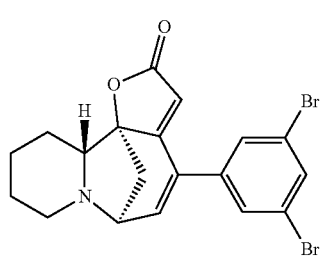

INVS-MG-65B

C-14 Alkyl/Aryl Analogs of Securinine:

Bis(triphenylphosphine)palladium(II)dichloride (7 mg, 0.01 mmol) was added to a stirred solution of INVS-MG-52A (34.3 mg, 0.1 mmol) in anhydrous toluene or tetrahydrofuran (0.75 ml) followed by the corresponding boronic acid (0.2 mmol) and then potassium carbonate/water (20 mg, 0.15 mmol/75 uL). The reaction mixture was degassed under nitrogen atmosphere for 15 minutes and then gradually heated to 80° C. to 100° C. The reaction progress was monitored by TLC and the reaction mixture was stirred at that temperature for 1 to 2 h until the starting material was completely consumed. The reaction mixture was poured in water (2 ml) and extracted with ethylacetate (2×3 ml) and the combined organic layers were washed with brine (5 ml), dried over sodium sulfate and concentrated on the rotary evaporator. The crude product was dried under high vacuum and purified by silica gel chromatography using appropriate solvent system to afford the desired C-14 alkyl/aryl analog of securinine in 40-70% yield. The following C-14 alkyl/aryl analogs of securinine have been synthesized employing the above. All the compounds were characterized by 1H NMR.

In another variation, the process comprising the synthesis of C-14 alkynyl analogs of securinine can be prepared using INVS-MG-52A and the corresponding terminal alkynes as outlined below.

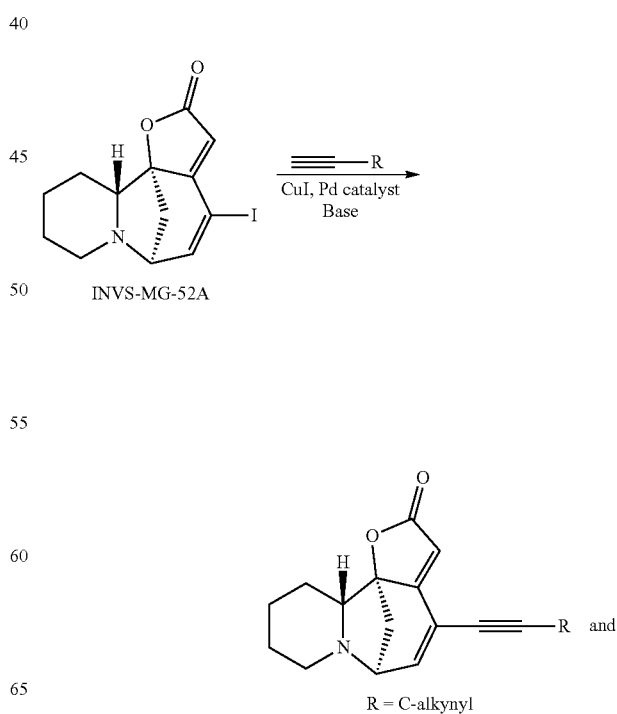

-continued

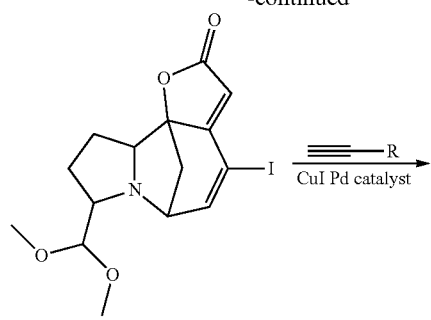

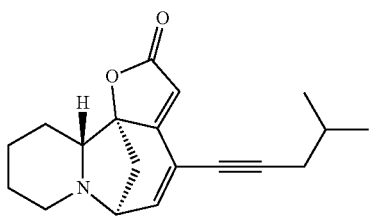
INVS-MG-109-IIA

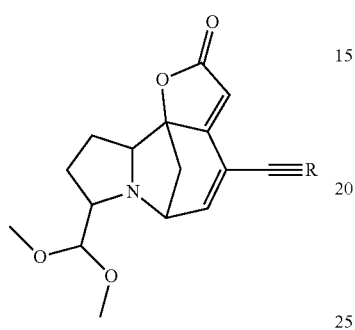

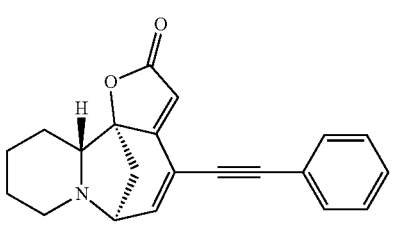
INVS-MG-110B

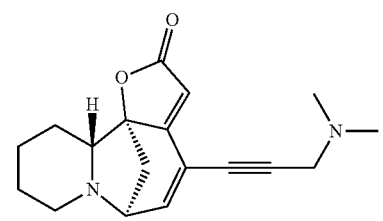
INVS-MG-111B

C-14 Alkynyl Analogs of Securinine:

To a solution of INVS-MG-52A (26 mg, 0.075 mmol) in anhydrous 1,4-dioxane/tetrahydrofuran (0.75 ml) was added bis(triphenylphosphine)palladium(II)dichloride (2.6 mg, 0.00375 mmol), CuI (1.5 mg, 0.0075 mmol) and tryethylamine (52 uL, 0.375 mmol). The reaction mixture was degassed under nitrogen atmosphere for 10 minutes and then gradually heated to 80° C. At this point, the reaction mixture turned into homogeneous, clear, dark brown solution. Heating removed to bring the reaction mixture to room temperature, and the corresponding alkyne (0.1125 mmol) was added. The reaction progress was monitored by TLC and the reaction mixture was stirred at that temperature for 1 to 2 h until the starting material was completely consumed. The reaction mixture was poured in water (2 ml) and extracted with ethylacetate (2×3 ml) and the combined organic layers were washed with brine (5 ml), dried over sodium sulfate and concentrated on the rotary evaporator. The crude product was dried under high vacuum and purified by silica gel chromatography using appropriate solvent system to afford the corresponding C-14 alkynyl analog of securinine. The following C-14 alkynyl analogs of securinine have been synthesized employing the above procedure in good yields (50-90%). All the compounds were characterized by 1H NMR.

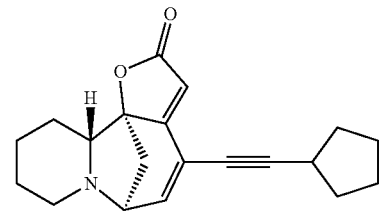
INVS-MG-113A

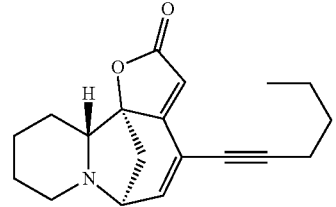
INVS-MG-117B

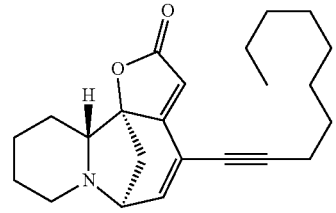
INVS-MG-118B

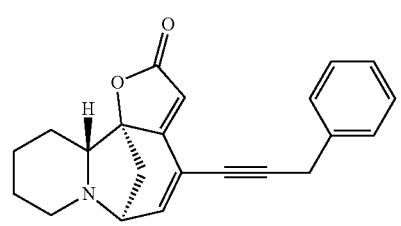
INVS-MG-108B

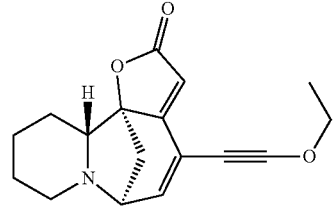
INVS-MG-120A

113
-continued
INVS-MG-121A
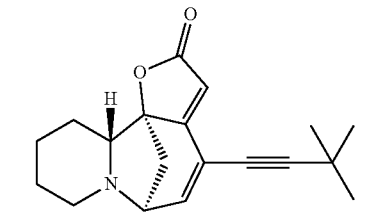
INVS-MG-123B
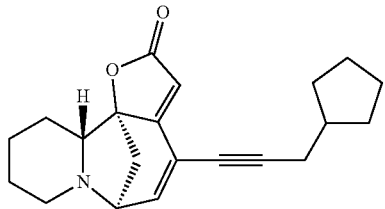
INVS-MG-124A
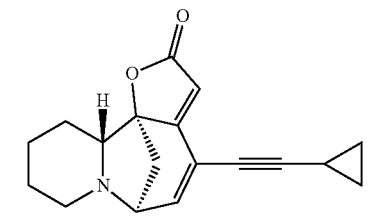
INVS-MG-125A
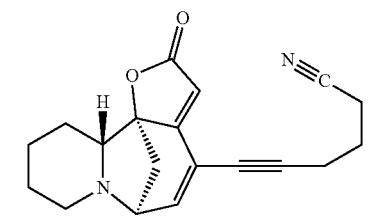
INVS-MG-131A
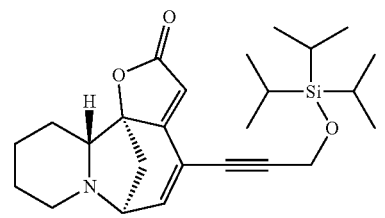
INVS-MG-132A
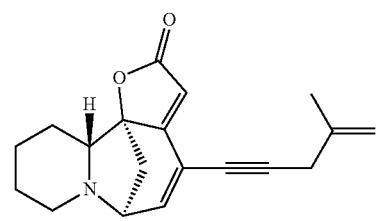
INVS-MG-134C
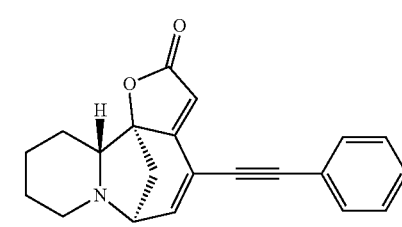
114
-continued
INVS-MG-135B
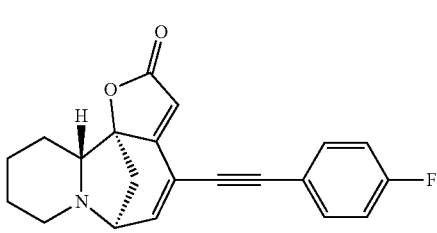
INVS-MG-136B
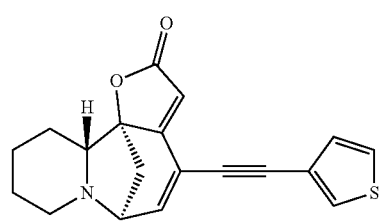
INVS-MG-133B
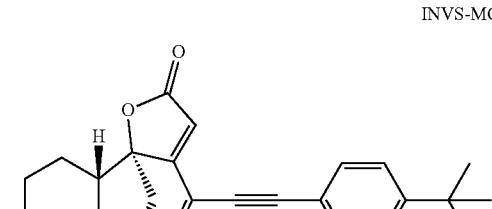
INVS-MG-133B
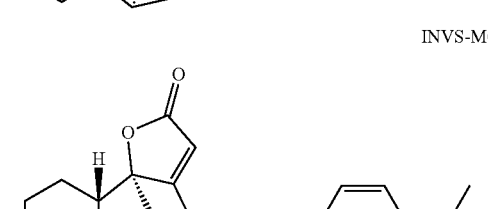
INVS-MG-137B
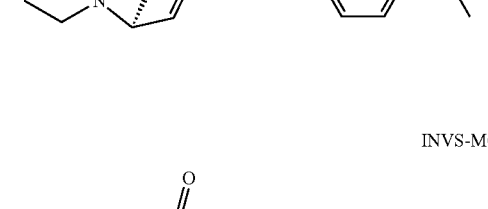
INVS-MG-138B
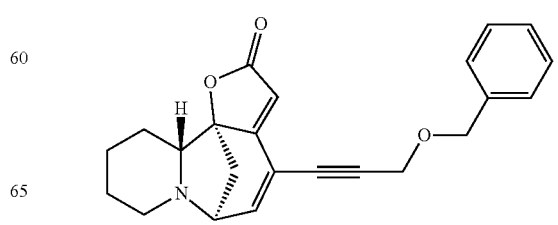

INVS-MG-145A
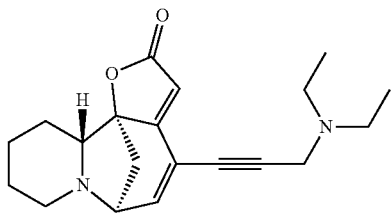
INVS-MG-146B
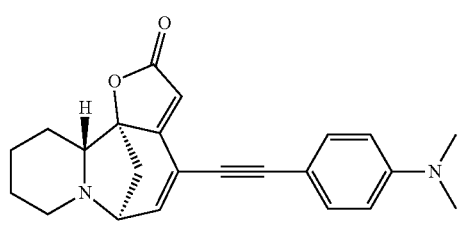
INVS-MG-150B
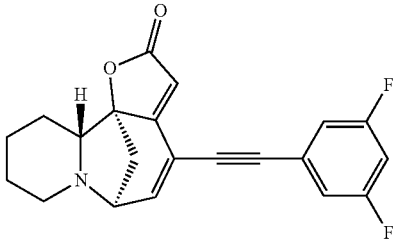
INVS-MG-151B
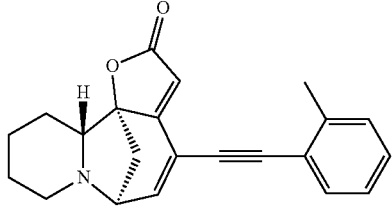
INVS-MG-152A
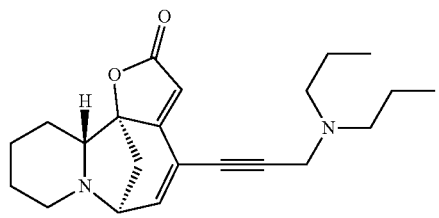
INVS-MG-157B
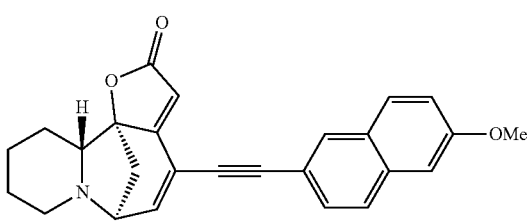
INVS-MG-158B
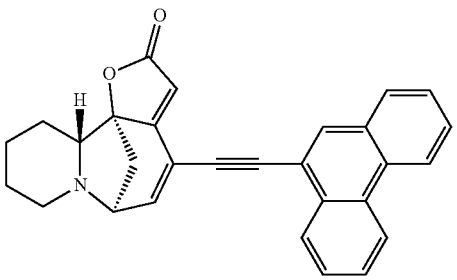
INVS-MG-159A
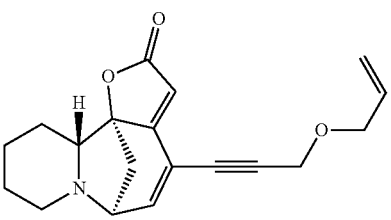
INVS-MG-160B
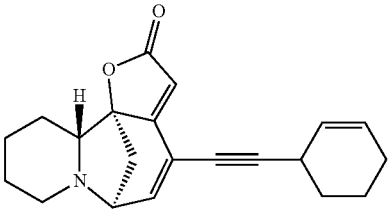
INVS-MG-161B
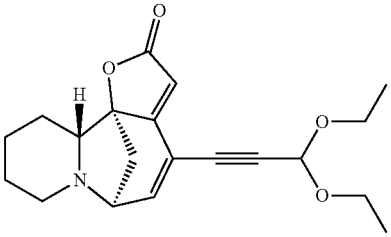
INVS-MG-162B
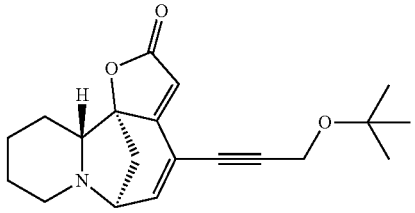
INVS-MG-164B
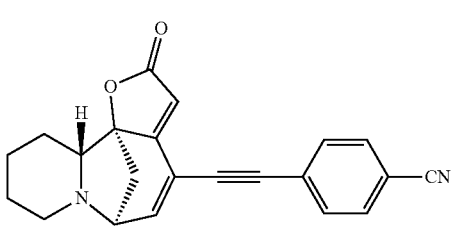

INVS-MG-165B

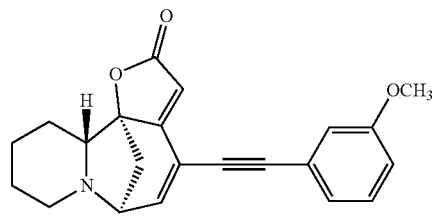

INVS-MG-166B

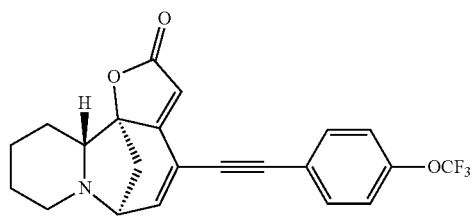

INVS-MG-167B

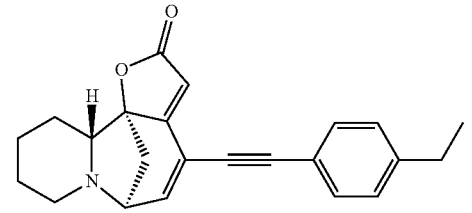

INVS-MG-168B

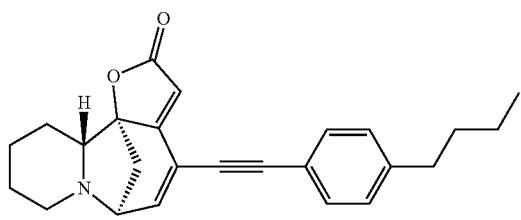

INVS-MG-169B

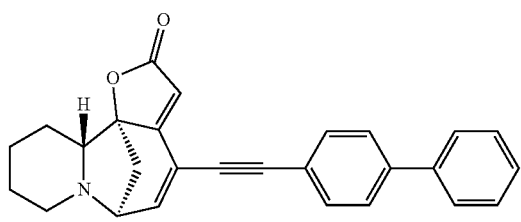

INVS-MG-170B

INVS-MG-175A

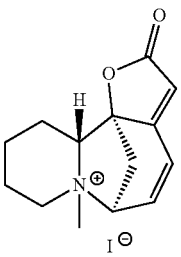

INVS-MG-193B

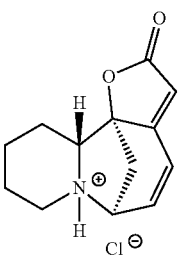

Preparation of Pharmaceutically Useful Salts:

In another variation, the process comprising the synthesis of various pharmaceutically useful salts can be prepared from the corresponding securinine analogs as outlined below.

Securinine analog (0.1 mmol) was dissolved in 1,4-dioxane (0.5 ml) and 2N HCl/1,4-dioxane solution was added to the reaction mixture at 0° C. The reaction mixture was stirred for 30 minutes to 2 hours at 0° C. as the product slowly precipitated. 1 ml of hexanes or ether was added and the solids were filtered, washed with 1 ml of hexanes/ether to obtain the corresponding HCl salt.

Securinine analog (0.1 mmol) was dissolved in methanol and tartaric acid (0.1 mmol) was added. The reaction mixture was gradually heated to 80° C. for several hours as the product slowly precipitated. 1 ml of ether was added and the solids were filtered, washed with 1 ml of ether to obtain the corresponding tartarate salt.

The following various pharmaceutically useful salts of securinine analogs have been prepared and characterized by 1H NMR

INVS-MG-70

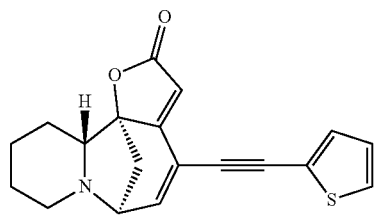

INVS-MG-72

INVS-MG-83
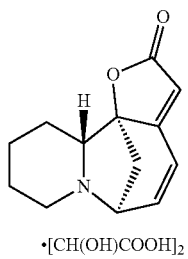
•[CH(OH)COOH]$_2$
INVS-MG-71
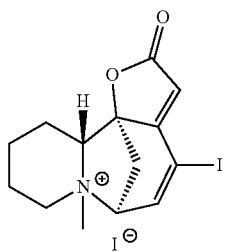
INVS-MG-73
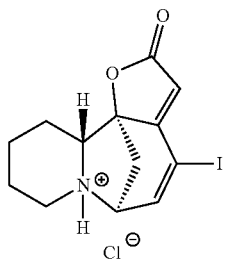
INVS-MG-84
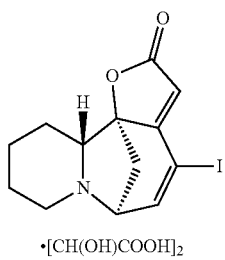
•[CH(OH)COOH]$_2$
INVS-MG-111-IV
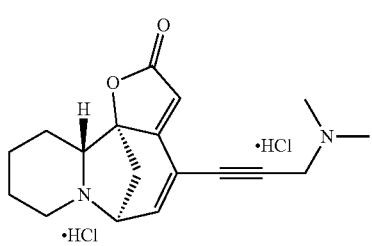
•HCl
INVS-MG-125-III
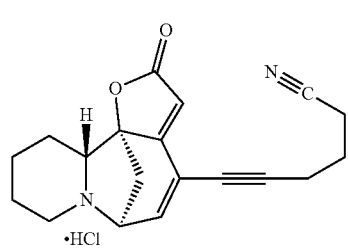
•HCl
INVS-MG-157-III
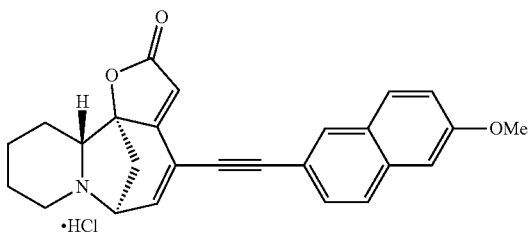
•HCl
INVS-MG-158-III
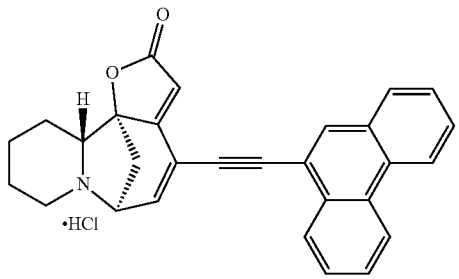
•HCl
INVS-MG-169-III
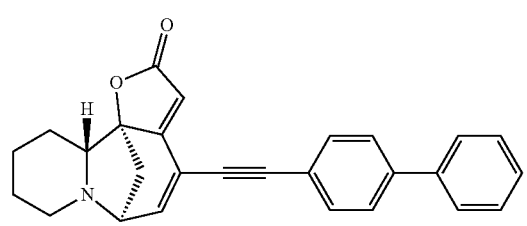
•HCl
INVS-MG-170-III
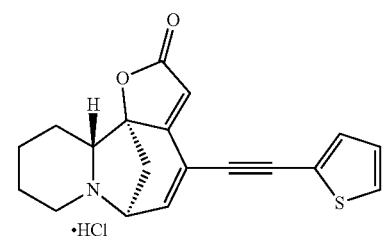
•HCl
INVS-MG-146-III
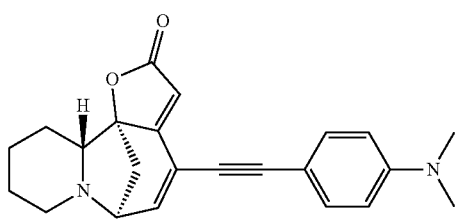
•2HCl
INVS-MG-152-III
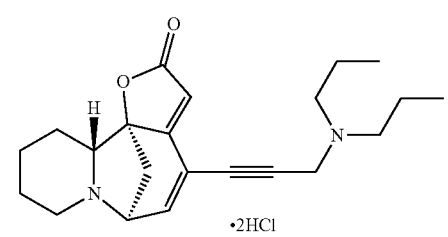
•2HCl INVS-MG-175-V
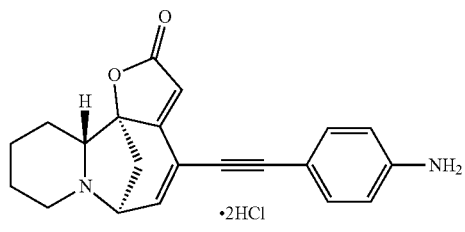
INVS-MG-193-III
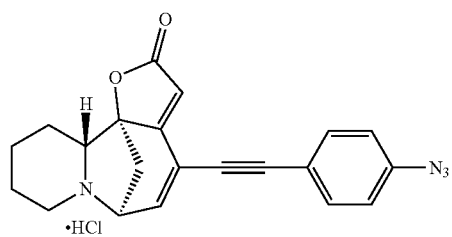
INV-SZ-113-2
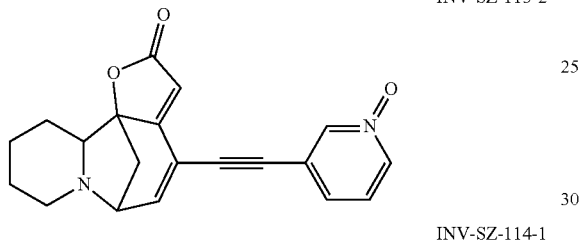
INV-SZ-114-1
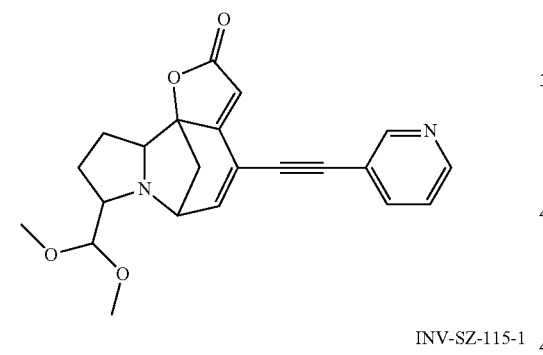
INV-SZ-115-1
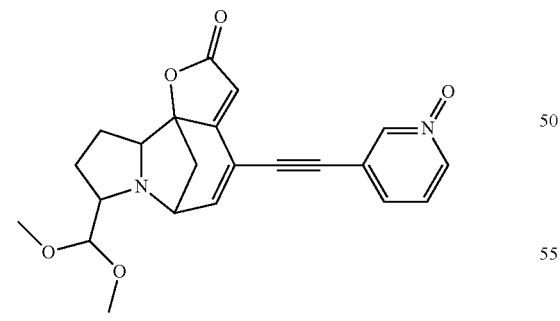
INV-SZ-116-1
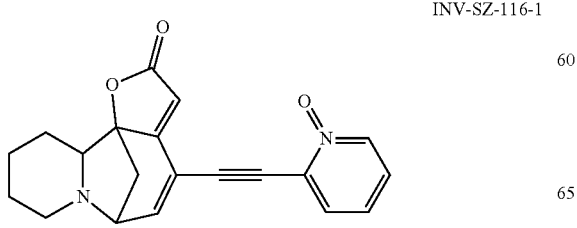
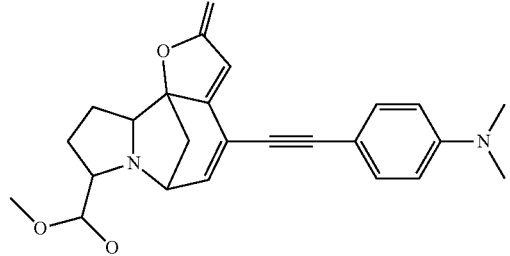
INV-SZ-118-2
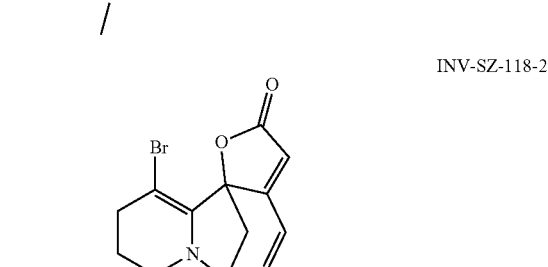
INV-SZ-120-1
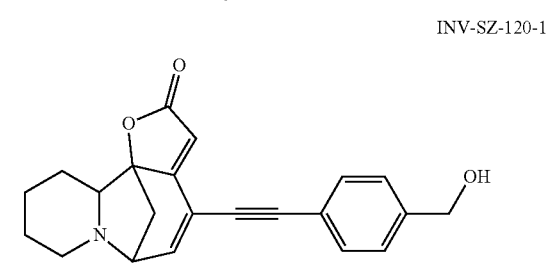
INV-SZ-121-1
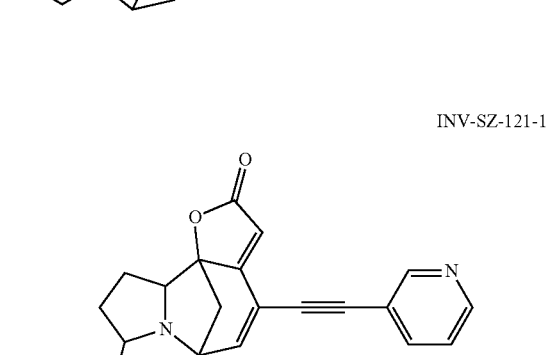
INV-SZ-122-1
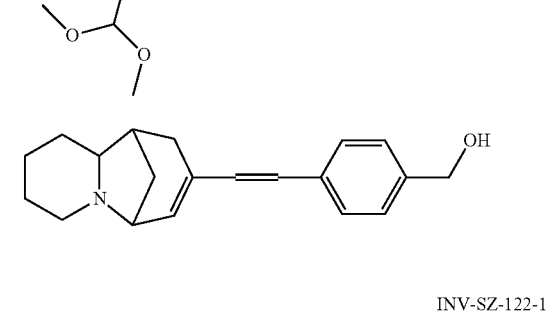

INV-SZ-123-2

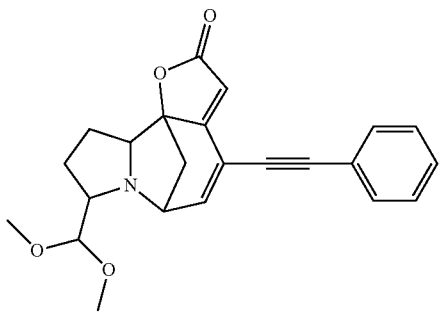

INV-SZ-123-3

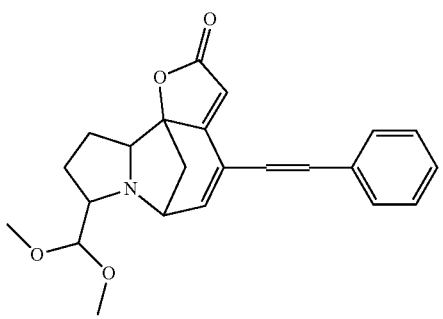

INV-SZ-125-1

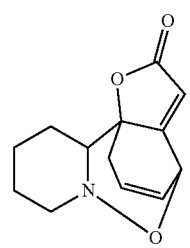

INV-SZ-125-2

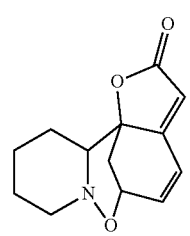

INV-SZ-125-3

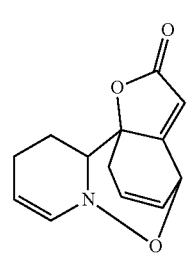

INV-SZ-127-1

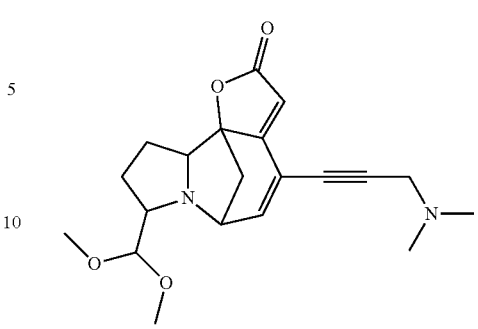

INV-SZ-129-1

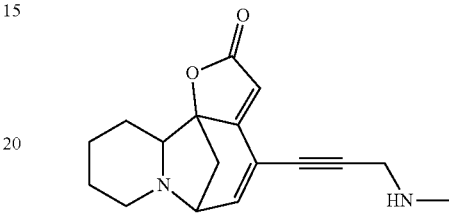

C-15 Reduced Analogs

C-15 reduced analogs of securinine were prepared. C-15 analogs of securinine can be prepared by 1,6-conjugate addition of thials/amines following the general procedure outlined below.

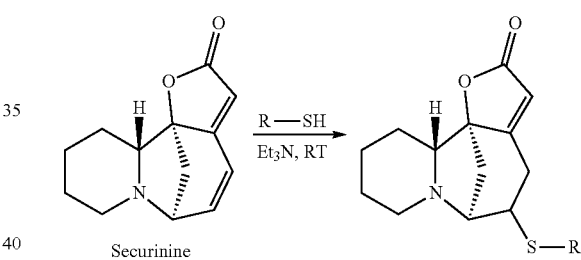

Securinine

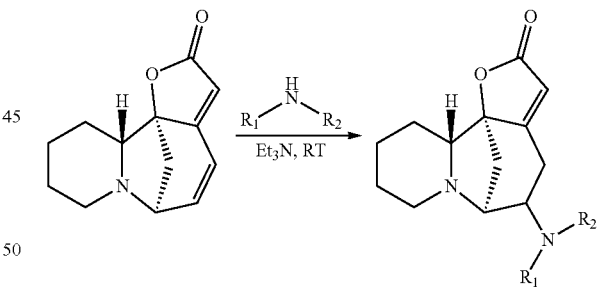

54.3 mg of securinine (0.25 mmol) and 0.3-0.4 mmol of the corresponding amine/thial were weighed in an oven dried reaction flask equipped with a septa or a 4 ml vial with a Teflon cap. 1 ml of acetonitrile followed by tryethylamine (139 uL, 1 mmol) was added and the reaction mixture was stirred under nitrogen atmosphere at room temperature. The reaction mixture was monitored by TLC. The reaction mixture was allowed to stir about 8 h to 2 days at room temperature until the starting material was completely consumed or maximum product formation was observed. All the volatiles in the reaction mixture were evaporated under reduced pressure and the crude product was purified by flash column chromatography on silica gel, using appropriate hexanes/acetone solvent system. The following C-15 analogs of securinine have been synthesized employing the above procedure in good yields (55-95%). All the compounds were characterized by 1H NMR.
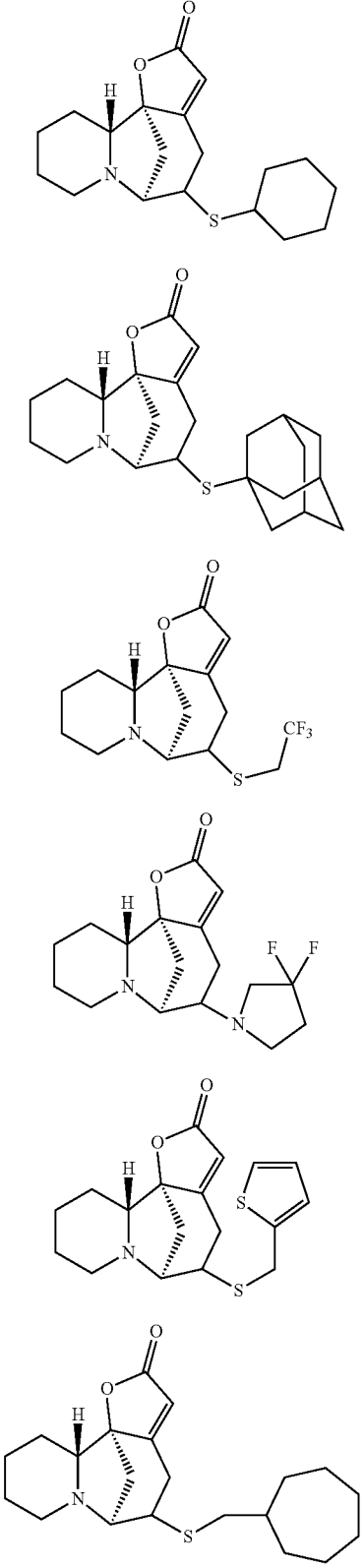
INVS-MG-3B
INVS-MG-4B
INVS-MG-5C
INVS-MG-9A
INVS-MG-14B
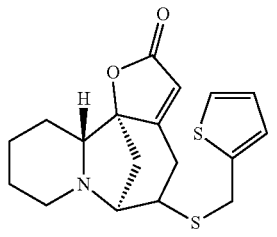
INVS-MG-16A
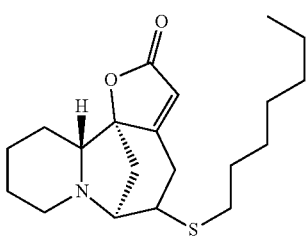
INVS-MG-19A
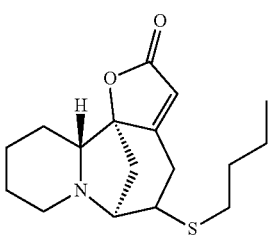
INVS-MG-20B
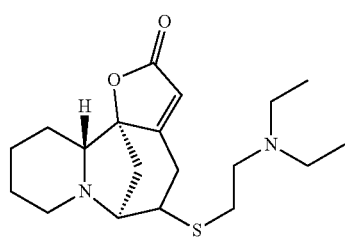
INVS-MG-21B
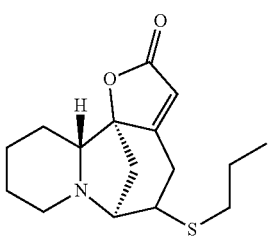
INVS-MG-34B/INV-2B
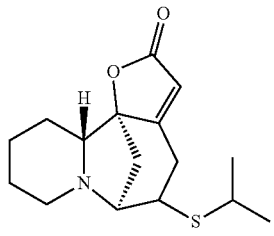
INVS-MG-37B/INV-26C
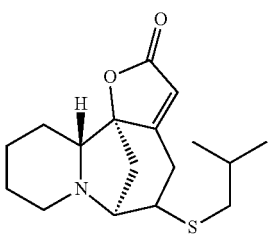
INVS-MG-57B INVS-MG-105C
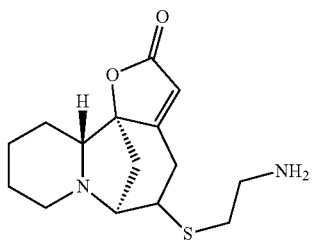
INVS-MG-106B
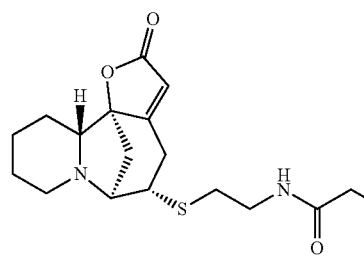
INVS-MG-25B
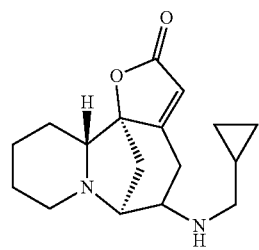
INVS-MG-26A
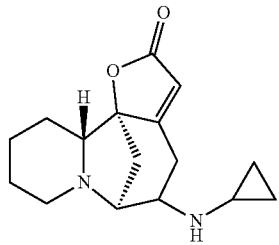
INVS-MG-27B
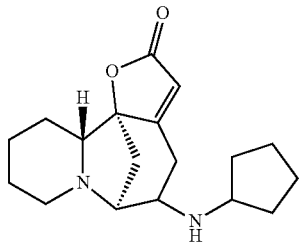
INVS-MG-28B
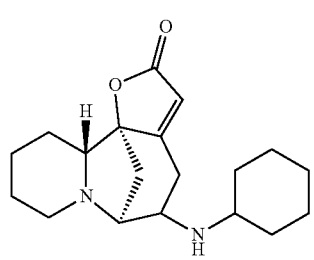
INVS-MG-29A
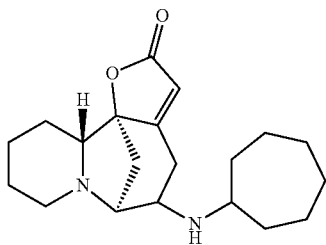
INVS-MG-30A
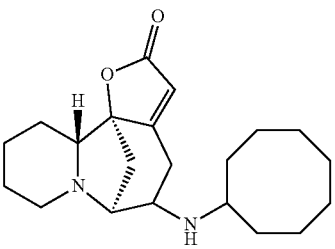
INVS-MG-46B
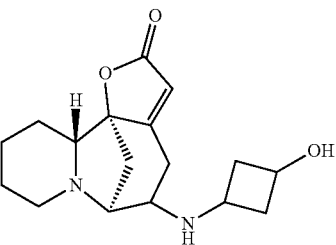
INVS-MG-86B
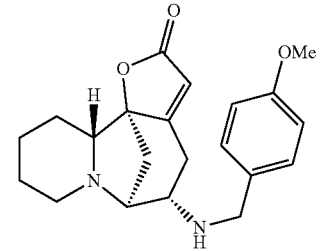
INVS-MG-172C
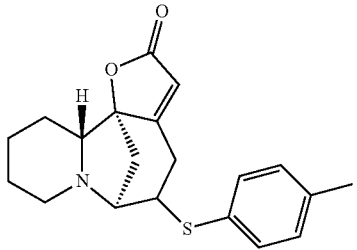
INVS-MG-184B
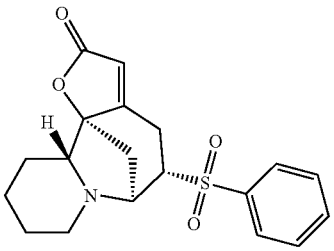

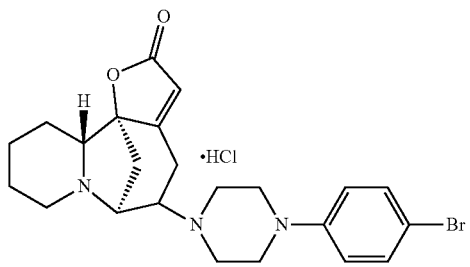
Sec-11
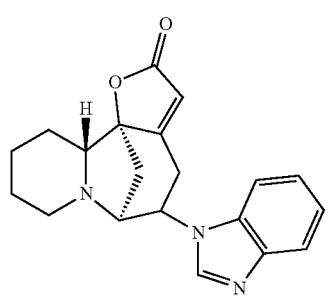
Sec-12
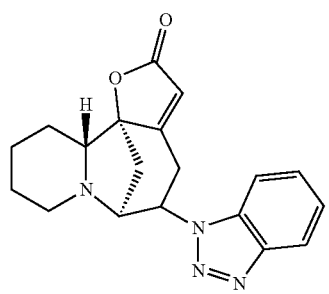
Sec-13
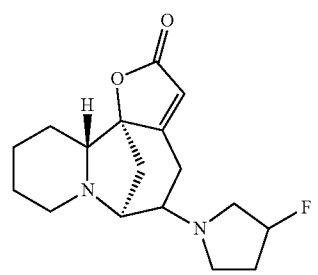
INV₂A
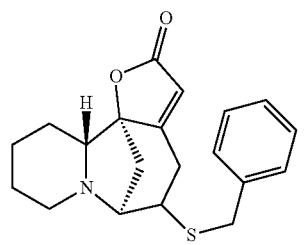
Sec 2
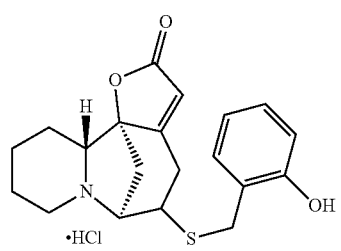
Sec 4
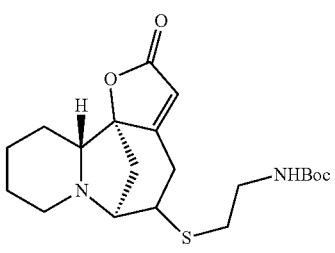
Sec 5
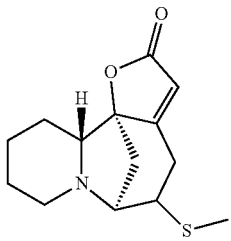
Sec 8
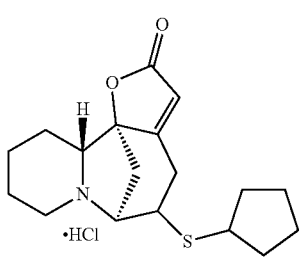
Sec 6
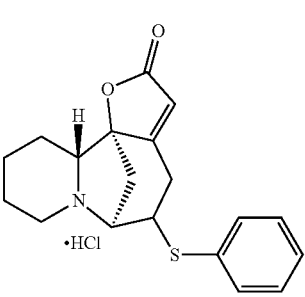
Sec 9
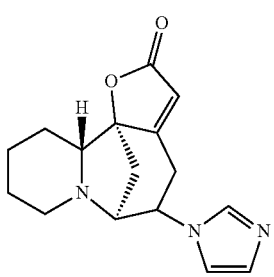
Sec 15
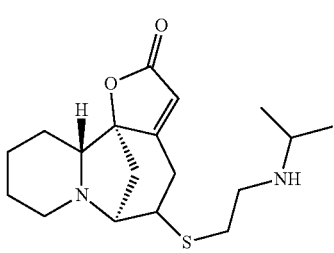
Sec 17

-continued

INVS-MG-98B

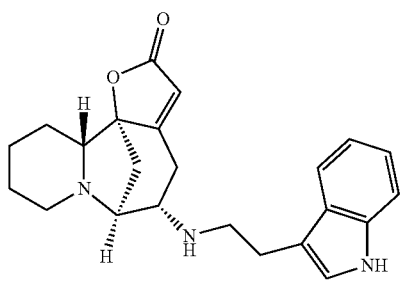

Securinine and Norsecurinine Analogs in MPO Related Conditions.

Chronic obstructive pulmonary disease (COPD) is a major global health problem, affecting over 10% of the population aged 40 years and older and contributing to 3 million deaths annually. COPD is the third leading cause of death in the United States and currently afflicts about 24 million Americans. While there is growing consensus that neutrophils play a prominent role in the pathogenesis of COPD, the role of various enzymes expressed by neutrophils has not been well studied as possible circulating biomarker in COPD. One intriguing enzyme is myeloperoxidase (MPO).

Myeloperoxidase (MPO), a neutrophil and macrophage product, is important in bacterial killing, but also drives inflammatory reactions and tissue oxidation. MPO, a member of the haem peroxidase-cyclooxygenase superfamily, is abundantly expressed in neutrophils and to a lesser extent in monocytes and certain type of macrophages. Numerous lines of evidence implicate a role for MPO in the pathogenesis of various diseases. MPO is present in wide varieties of tissue however their pathogenic roles are different depending on the types and stages of diseases. A unique activity of MPO is its ability to use chloride as a co-substrate with hydrogen peroxide to generate chlorinating oxidants such as hypochlorous acid, a potent antimicrobial agent. However, evidence has emerged that MPO-derived oxidants contribute to tissue damage and the initiation and propagation of acute and chronic vascular inflammatory disease. The fact that circulating levels of MPO have been shown to predict risks for major adverse cardiac events and that levels of MPO-derived chlorinated compounds are specific biomarkers for disease progression, has attracted considerable interest in the development of therapeutically useful MPO inhibitors. Today, detailed information on the structure of ferric MPO and its complexes with low- and high-spin ligands is available. This, together with a thorough understanding of reaction mechanisms including redox properties of intermediates, enables a rationale attempt in developing specific MPO inhibitors that still maintain MPO activity during host defense and bacterial killing but interfere with pathophysiologically persistent activation of MPO. The various approaches to inhibit enzyme activity of MPO and to ameliorate adverse effects of MPO-derived oxidants will be discussed. Emphasis will be put on mechanism-based inhibitors and high-throughput screening of compounds as well as the discussion of physiologically useful HOCl scavengers. These factors likely contribute to clinical studies demonstrating that increased systemic levels of MPO and its oxidation products predict increased risk factors for disease like COPD, cardiovascular, lung cancer, etc.

Figure 3:
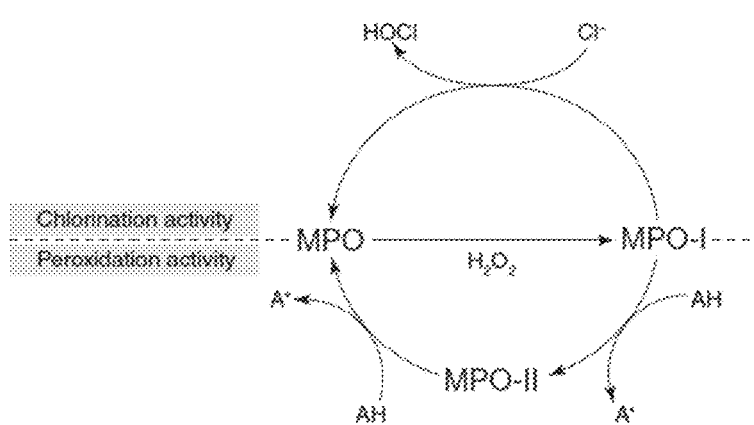
FIG. 3 shows the mechanism of chlorination and peroxidation activity of MPO.
Figure 4:
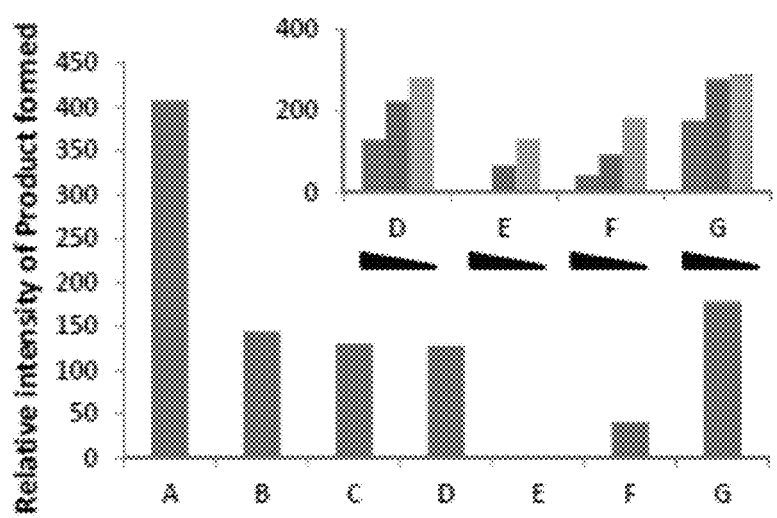
FIG. 4 shows the chlorination activity of MPO. Dose dependent chlorination inhibition is showed in inset box. The columns are represented as follows: A: Blank; B: Commercial inhibitor; C; Another commercial inhibitor (sc-204107); D: Securinine; E: INVS-MG-98B, F: 14-Iodosecurinine; G; INVS-MG-106B.

MPO is a lysosomal enzyme that neutrophils use to kill microbes by generating a potent oxidant, hypochlorous acid (See FIGS. 3 and 4). It is heavily expressed in primary (azurophilic) granules of neutrophils. Recent studies suggest a prominent role of MPO in the pathogenesis of COPD including progression of emphysema, pulmonary hypertension, and small airway remodeling and support the emerging role of myeloperoxidase in the pathogenesis of COPD progression and cardiovascular disease. Contacting MPO with the securinine and norsecurinine derivative described herein provide enzymatic inhibitors based on the securinine and norsecurinine scaffold. The results provided in Table 1 present data establishing that the analogs are potent inhibitors of MPO. More specifically, the analogs act by inhibiting chlorination activity The analogs described herein were contacted against MPO and the biological activity was assessed. Tables 1 and 2 show representative biological activity examples and that the listed compounds are potent inhibitors of MPO, specifically that the analogs inhibit chlorination activity. The compounds were tested for MPO inhibitory activity using the Myeloperoxidase Inhibitor Screening Assay Kit (Cayman Chemical Cat #700170) as described in the manufacturers manual

TABLE 1

| S.N. | Code | Structure | % Activity |
| --- | --- | --- | --- |
| 1 | K-I | Positive control | 99 |
| 2 | 4A | 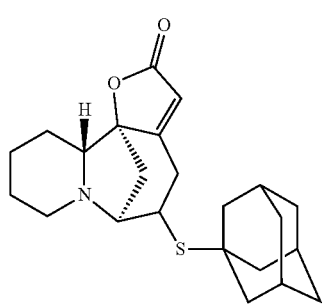 [SMILES: O=C1C=C2CC(SC34CC5CC(CC(C5)C3)C4)[C@@H]3C[C@@]2(O1)[C@H]1CCCCN31] | 1 |

TABLE 1-continued

| S.N. | Code | Structure | % Activity |
|---|---|---|---|
| 3 | 5A | 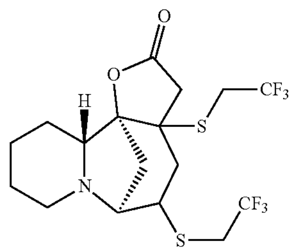 [SMILES: O=C1CC2(SCC(F)(F)F)CC(SCC(F)(F)F)[C@@H]3C[C@@]2(O1)[C@H]1CCCCN31] | 78 |
| 4 | 5B | 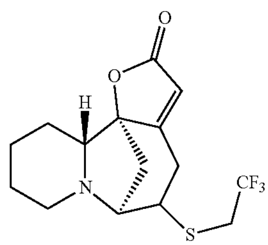 [SMILES: O=C1C=C2CC(SCC(F)(F)F)[C@@H]3C[C@@]2(O1)[C@H]1CCCCN31] | 83 |
| 5 | 9A | 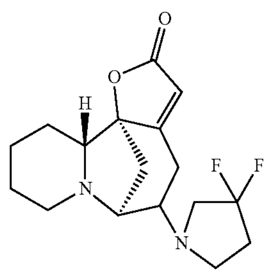 [SMILES: O=C1C=C2CC(N3CCC(F)(F)C3)[C@@H]3C[C@@]2(O1)[C@H]1CCCCN31] | 46 |
| 6 | 14B | 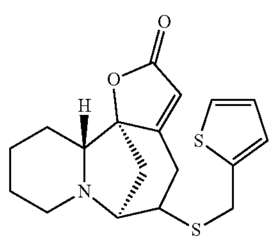 [SMILES: O=C1C=C2CC(SCc3cccs3)[C@@H]3C[C@@]2(O1)[C@H]1CCCCN31] | 83 |
| 7 | 16A | 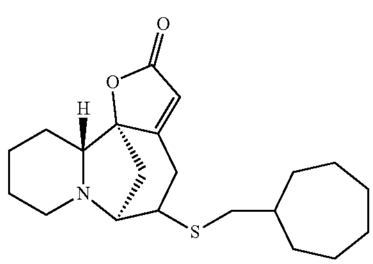 [SMILES: O=C1C=C2CC(SCC3CCCCCC3)[C@@H]3C[C@@]2(O1)[C@H]1CCCCN31] | 91 |
| 8 | 19A | 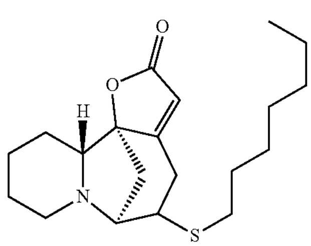 [SMILES: CCCCCCCSC1CC2=CC(=O)O[C@@]23C[C@@H]1N1CCCC[C@@H]13] | 38 |

TABLE 1-continued

| S.N. | Code | Structure | % Activity |
|---|---|---|---|
| 9 | 21B | 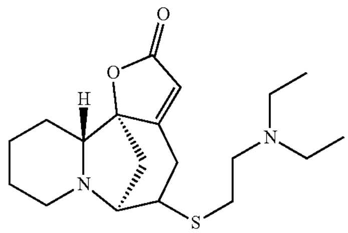 [SMILES: CCN(CC)CCSC1CC2=CC(=O)O[C@@]23C[C@@H]1N1CCCC[C@@H]13] | 30 |
| 10 | 25B | 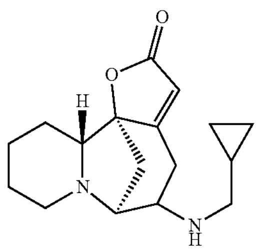 [SMILES: O=C1C=C2CC(NCC3CC3)[C@@H]3C[C@@]2(O1)[C@H]1CCCCN31] | 99 |
| 11 | 26A | 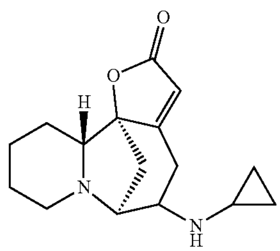 [SMILES: O=C1C=C2CC(NC3CC3)[C@@H]3C[C@@]2(O1)[C@H]1CCCCN31] | 83 |
| 12 | 27B | 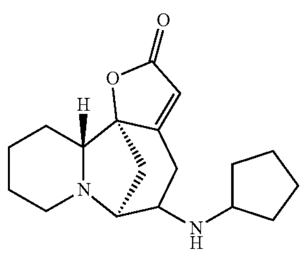 [SMILES: O=C1C=C2CC(NC3CCCC3)[C@@H]3C[C@@]2(O1)[C@H]1CCCCN31] | 46 |
| 13 | 28B | 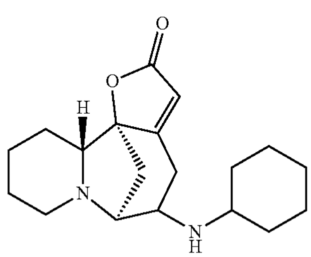 [SMILES: O=C1C=C2CC(NC3CCCCC3)[C@@H]3C[C@@]2(O1)[C@H]1CCCCN31] | 86 |
| 14 | 29A | 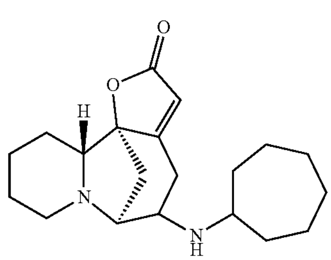 [SMILES: O=C1C=C2CC(NC3CCCCCC3)[C@@H]3C[C@@]2(O1)[C@H]1CCCCN31] | 1 |

TABLE 1-continued

| S.N. | Code | Structure | % Activity |
|------|------|-----------|------------|
| 15 | 30A | 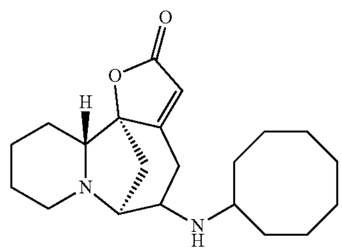 [SMILES: O=C1C=C2CC(NC3CCCCCCC3)[C@@H]3C[C@@]2(O1)[C@H]1CCCCN31] | 78 |
| 16 | 37B | 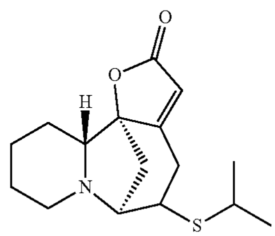 [SMILES: CC(C)SC1CC2=CC(=O)O[C@@]23C[C@@H]1N1CCCC[C@@H]13] | 97 |
| 17 | 46B | 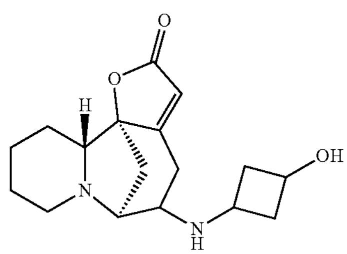 [SMILES: O=C1C=C2CC(NC3CC(O)C3)[C@@H]3C[C@@]2(O1)[C@H]1CCCCN31] | 99 |
| 18 | 57A | 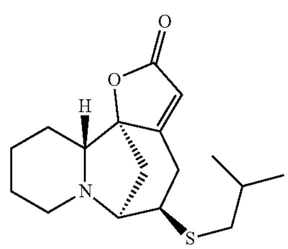 [SMILES: CC(C)CS[C@@H]1CC2=CC(=O)O[C@@]23C[C@@H]1N1CCCC[C@@H]13] | 86 |
| 19 | 57B | 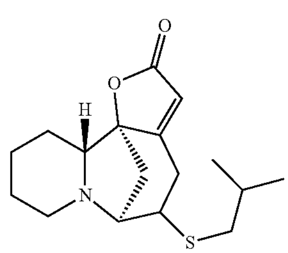 [SMILES: CC(C)CSC1CC2=CC(=O)O[C@@]23C[C@@H]1N1CCCC[C@@H]13] | 2 |
| 20 | 58C | 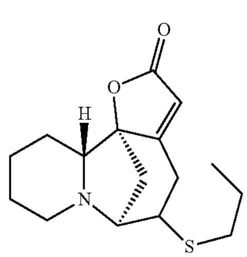 [SMILES: CCCSC1CC2=CC(=O)O[C@@]23C[C@@H]1N1CCCC[C@@H]13] | 30 |

TABLE 1-continued

| S.N. | Code | Structure | % Activity |
|---|---|---|---|
| 21 | 97-IIB | 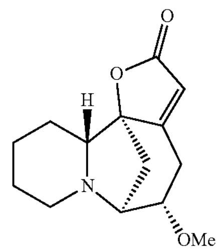 [SMILES: CO[C@H]1CC2=CC(=O)O[C@@]23C[C@@H]1N1CCCC[C@@H]13] | 97 |
| 22 | 98B | 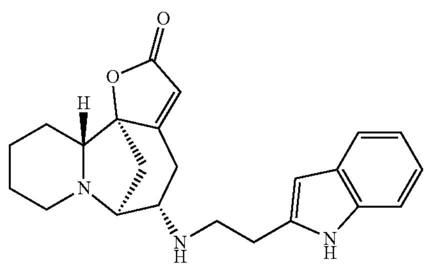 [SMILES: O=C1C=C2C[C@H](NCCc3cc4ccccc4[nH]3)[C@@H]3C[C@@]2(O1)[C@H]1CCCCN31] | 88 |
| 23 | 105 | 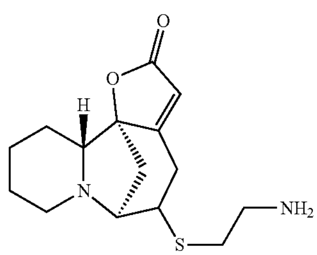 [SMILES: NCCSC1CC2=CC(=O)O[C@@]23C[C@@H]1N1CCCC[C@@H]13] | 99 |
| 24 | SEC-BIO | 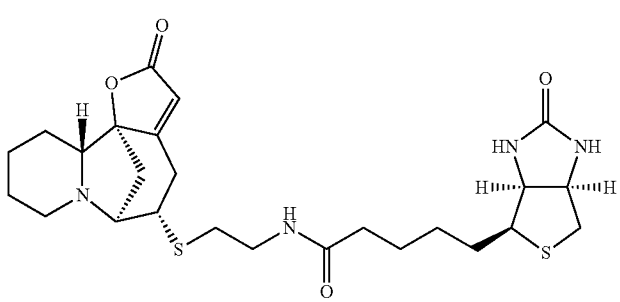 [SMILES: O=C(CCCC[C@@H]1SC[C@@H]2NC(=O)N[C@@H]21)NCCS[C@H]1CC2=CC(=O)O[C@@]23C[C@@H]1N1CCCC[C@@H]13] | 32 |
| 25 | 152A | 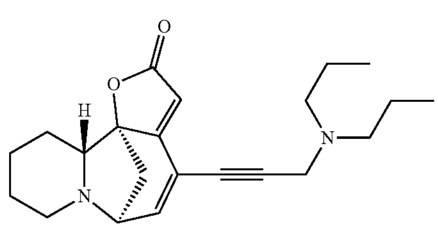 [SMILES: CCCN(CC#CC1=C[C@@H]2C[C@@]3(OC(=O)C=C13)[C@H]1CCCCN21)CCC] | 18 |
| 26 | 157B | 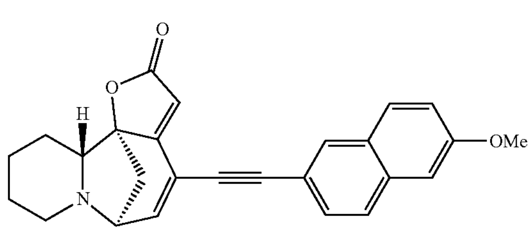 [SMILES: COc1ccc2cc(C#CC3=C[C@@H]4C[C@@]5(OC(=O)C=C35)[C@H]3CCCCN43)ccc2c1] | 80 |

TABLE 1-continued

| S.N. | Code | Structure | % Activity |
|---|---|---|---|
| 27 | 170B | 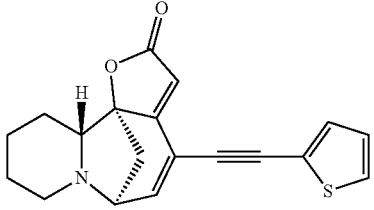 [SMILES: O=C1C=C2C(C#Cc3cccs3)=C[C@@H]3C[C@@]2(O1)[C@H]1CCCCN31] | 64 |
| 28 | 207A | 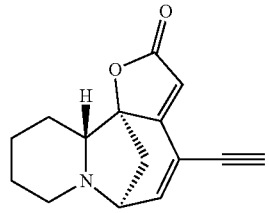 [SMILES: C#CC1=C[C@@H]2C[C@@]3(OC(=O)C=C13)[C@H]1CCCCN21] | 99 |
| 29 | 222B | 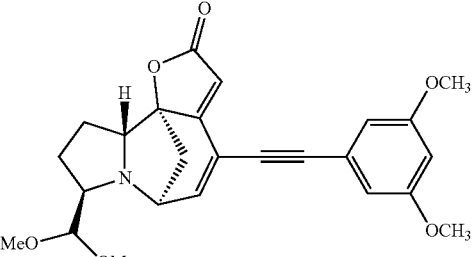 | 70 |
| 30 | SEC | 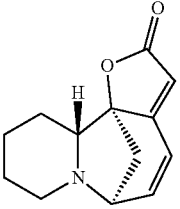 [SMILES: O=C1C=C2C=C[C@@H]3C[C@@]2(O1)[C@H]1CCCCN31] | 32 |

TABLE 2

| Sample code | IC$_{50}$ |
|---|---|
| INVS-MG-98B | 0.5 ± 0.06 |
| INVS-MG-184B | 0.7 ± 0.04 |
| INVS-MG-14B | 1.0 ± 0.8 |
| INVS-Sec-13 | 0.75 ± 0.05 |
| INVS-Sec-15 | 1.5 ± 0.04 |
| securinine | 1.1 ± 0.05 |

Studies were then aimed at establishing dose dependent relative chlorination activity results of securinine and norsecurinine analogs. As depicted in FIG. 4, the analogs of the present invention were extremely potent in inhibiting chlorination.

Figure 5:
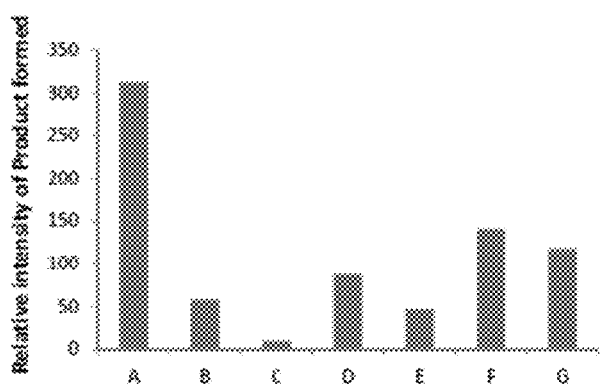
FIG. 5 shows the peroxidase activity of MPO. The columns are represented as follows: A: Blank; B: Commercial inhibitor (sc-204107); C; Another commercial inhibitor; D: Securinine; E: INVS-MG-98B, F: 14-Iodosecurinine; G; INVS-MG-106B

Further studies then worked to establish a dose dependent relative peroxidation activity As seen in FIG. 5, all tested compounds provided some degree of peroxidase inhibition.

Figure 6:
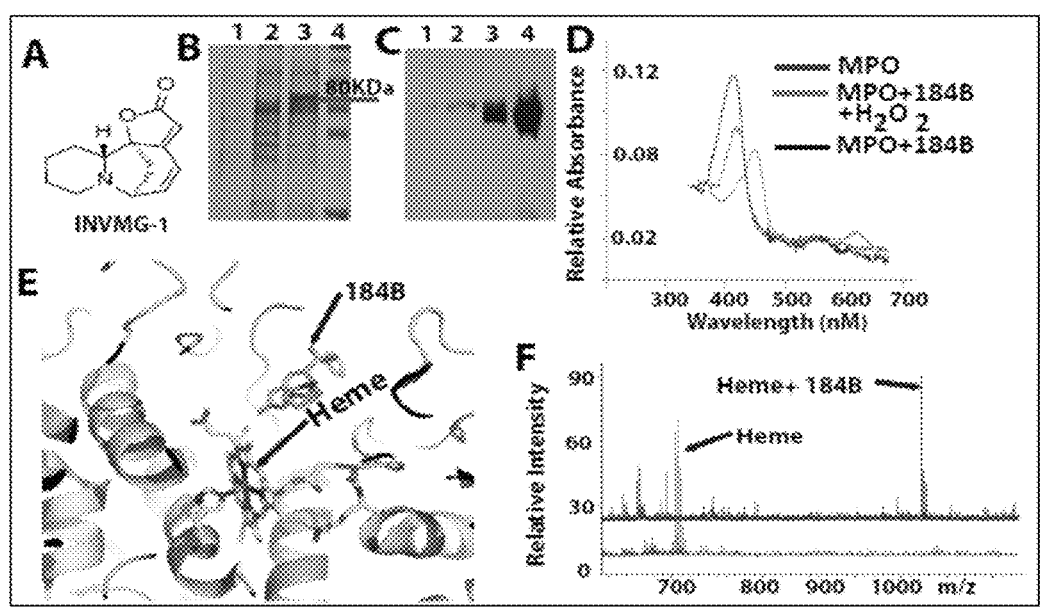
FIG. 6 shows an overview of securinine analogs affecting MPO.

It was next set about to investigate the molecular target of the analogs (FIG. 6A). Cultured HL60 cells were treated with either Biotin/Biotin-INVMG1 (securinine) (10 μM) for 2 hr and pull-down experiments using streptavidin magnetic beads were used to pulldown bound molecules, followed by SDS-PAGE analysis (FIG. 6B). SDS-PAGE analysis, using silver staining, clearly revealed the binding of INVMG1 to an 80 kDa protein (indicated by arrow in FIG. 4B). This 80 kDa protein band was excised, digested with trypsin, and the tryptic digests then analyzed using Mass Spectroscopy. MS analysis revealed that the identified protein band is MPO (FIG. 4B). The proteins bound to streptavidin beads were next separated using SDS-PAGE and incubated then with anti-human MPO antibody. Western blot analysis clearly revealed the binding of MPO to biotin-conjugated INVMG1 (Lane 3, FIG. 6C) in HL60 cells. To further confirm the binding of INVMG1 to MPO, the MPO enzyme was incubated with and without INVMG184B/H$_2$O$_2$, and analyzed absorption maxima using UV/visible. Spectrophotometric analysis clearly revealed the presence of a soret maximum at ~433 nm and a small absorbance peak at ~630 nm, which strongly indicates the direct binding of MA20 with the heme prosthetic group at ~630 nm (FIG. 6D).

To determine the binding motif/active site of MPO and the compound of interest, a computational docking analysis using a 2.5 A crystal structure (PDB id 3ZSO) was performed. The heme 'm' in myeloperoxidase contains two ester bonds at the heme 1 and 5-methyls. In addition, a unique sulfonium ion linkage was observed. INVMG1 and 184B both dock closer to the porphyrin on the left to this sulfonium-forming porphyrin group. An inhibitory action of the myeloperoxidase is predicted when such covalent links are formed. Especially docking position of 184B unique and have visible effect on the Hisitidine 336 coordinated iron (FIG. 6E). These docking results explain the observed effects of 184B on the soret peak (~433). Further MALDI-TOF analysis of heme (un conjugated) and heme/184B conjugated (in presence of $H_2O_2$) complexes are liberated from protein and analyzed ions with an ~m/z>1040, which would be the mass of conjugated heme and 184B compare to unconjugated control only heme (m/z~694) (FIG. 6F). This compelling evidence strongly suggests that the interaction of MPO and 184B is irreversible when physiological conditions were applied.

Figure 7:
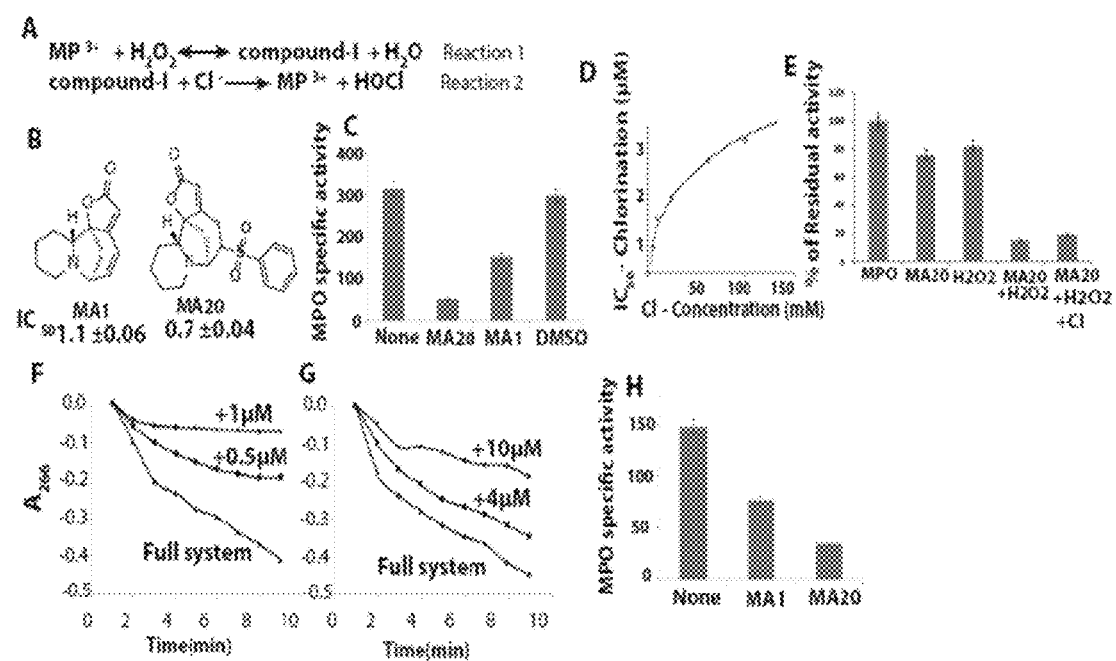
FIG. 7A shows redox intermediate of MPO when react with H2O2 and produce HOCl in presence of chloride. 7B shows 2D Structures MA1 and MA20, showed IC50 values. 7C shows Purified MPO used for chlorination assay. Bar shows the formation of HOCl by measuring fluorescent from APF by OCl—; bars from left: Only MPO; with MA20; with MA1; and with DMSO. 7D shows concentration of MA20 that inhibited production of hypochlorite by 50% (IC50) was determined over a range of chloride concentrations. 7E shows residual enzymatic activity of MPO (100 nM), various combination as indicated FG) oxidation of ascorbate by MPO, H2O2, and 100 mM chloride in the absence or presence of MA20, 7G shows, as in 7F but the system contained thyroid peroxidase and 50 μM iodide. 7H shows the effect of different analogues on HOCl production by human neutrophils stimulated by PMA: bars from left: No analogue; with MA1; and with MA20. All Results are representative of duplicate experiments

MPO's catalyzed enzymatic reaction consists of multiple stages (FIG. 3). Chlorination occurs when Complex-I produces hypochlorous acid (HOCl) in the presence of a chloride ion. C-15-substituted analogues showed variable MPO inhibition activity. Analogue MA20:

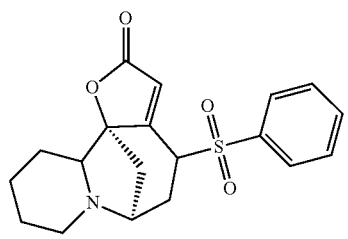 [SMILES: O=C1C=C2C(S(=O)(=O)c3ccccc3)C[C@@H]3C[C@@]2(O1)C1CCCCN13]

showed the highest MPO inhibition activity (assessed by chlorination activity, as indicated by the IC50 value in FIG. 7B-C). Furthermore, the inhibition potency (as measured by chlorination) of MA20 decreased with increasing concentrations of the chloride ion, indicating that the MPO inhibitory activity of MA20 is directly linked to chloride ion concentration (FIG. 7D). To determine the mechanism of this inhibition, the MPO enzyme was incubated with MA20 in the presence or absence of H2O2 for a set time and determined the reduction in chlorination activity of the enzyme. Residual activity was measured by diluting the reaction mixture by 150 fold. Incubation with either MA20 or H2O2 had minimal MPO inhibitory activity (approximately a 25-30% reduction in chlorination activity, FIG. 7E). Interestingly, the addition of MA20 and H2O2 completely inhibited MPO activity, when compared to the combined effects of MA20, H2O2, and chlorine (FIG. 7E).

These results suggest that compound MA20 forms a very stable MPO intermediate(s) in the presence of H2O2, which prevents the chlorination activity of MPO. To determine whether these analogues are selective for MPO, rather than being a general peroxidase inhibitor, thyroid peroxidase and lactoperoxidase were selected for oxidase evaluation. The effect of MA20 on the halogenation activities of MPO and thyroid peroxidase were compared by following the oxidation of ascorbate in the presence of chloride or iodide. At a concentration of 1.0 μM, MA20 completely blocked the oxidation of ascorbate by MPO; however, its effect on the iodination activity of thyroid peroxidase at 10 μM was negligible (FIG. 7F-G) indicating MA20 is a specific inhibitor of MPO. Similar results were observed using lactoperoxidase (data not shown).

To investigate the potency of MA20 in neutrophil in inhibiting chlorination, human neutrophils were incubated with 110 ng/ml of phorbal myristate acetate (PMA) for 30 min. The reaction was stopped by 251 μg/ml of catalase and 0.5 μM of MA20, and chlorination activity was measured. Incubation with MA20 significantly inhibited PMA-induced HOCl production by neutrophils (FIG. 7H). This effect is strikingly similar to MA20's inhibitory effect on purified MPO (FIG. 7C). In conclusion, our preliminary investigation suggests that these inhibitors (MA1 and MA20) bind avidly with the heme prosthetic groups of MPO before they can exit the active site of the enzyme. As such, they prevent the production of HOCl without concomitant release of free radicals. These preliminary data clearly indicate that the inhibitor MA20 is a suicidal substrate for the enzyme MPO.

Figure 8:
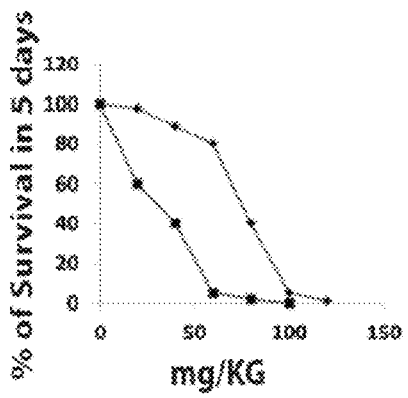
FIG. 8 shows that MA20 exhibited a significantly lower level of toxicity towards such cell types as Skin fibroblast (BJ1), HEK293, and mouse embryonic fibroblast (MEF) and a pharmacokinetics (PK) study using human liver microsomal (HLM) fraction revealed that MA20 had a longer half (~80 Min) compared to the parent compound.

The securinine analog MPO inhibitors have favorable in vitro and in vivo toxicity profiles. MA1 and majority of its analogues exhibit favorable in vitro toxicity profiles, as found by an MTT cell survival assay (Roche) to evaluate cell death under cell culture conditions. Although MA1 exhibited a higher toxicity effect on some cell lines, MA20 exhibited a significantly lower level of toxicity towards such cell types as Skin fibroblast (BJ1), HEK293, and mouse embryonic fibroblast (MEF) (FIG. 8). Finally, a pharmacokinetics (PK) study using human liver microsomal (HLM) fraction revealed that MA20 had a longer half (~80 Min) compared to the parent compound (FIG. 8).

All publications, patents and patent applications references herein are to be each individually considered to be incorporated by reference in their entirety.

The invention claimed is:

1. A method for inhibiting myeloperoxidase activity comprising contacting a myeloperoxidase enzyme with a securinine or nor securinine analog, wherein the securinine or norsecurinine analog comprises a structure selected from the group consisting of:

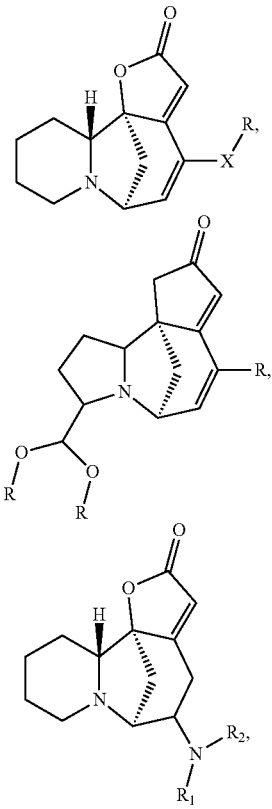

-continued

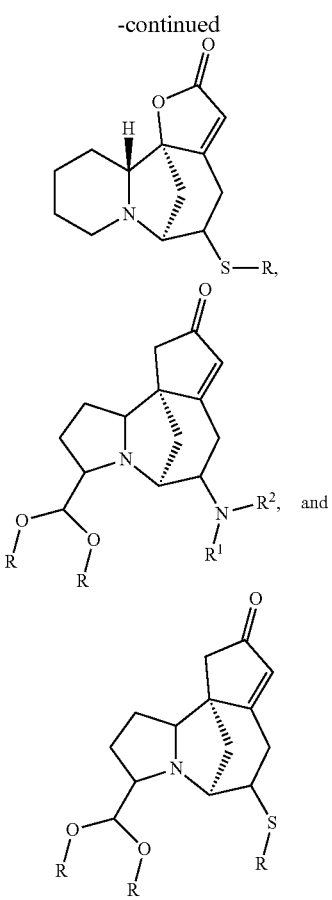

wherein X is a C, C—C, C═C or C≡C and R, $R_1$ or $R_2$ is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof.

2. The method of claim 1, wherein the structure is selected from the group consisting of:

INVS-MG-56A

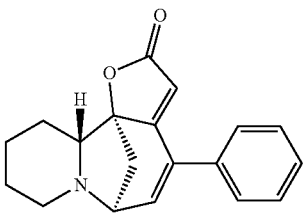

INVS-MG-54B

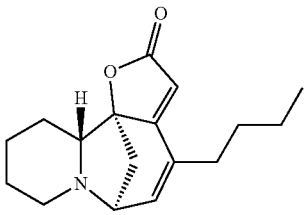

INVS-MG-63B

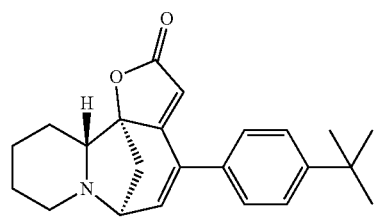

INVS-MG-64A

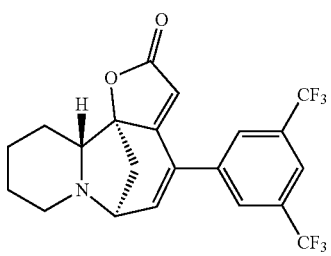

INVS-MG-65B

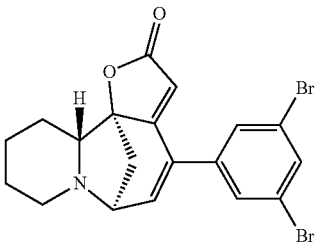

INVS-MG-108B

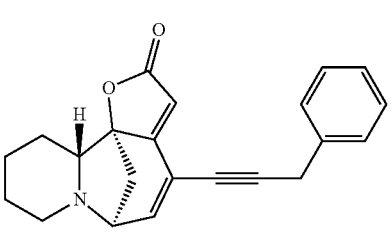

INVS-MG-109-IIA
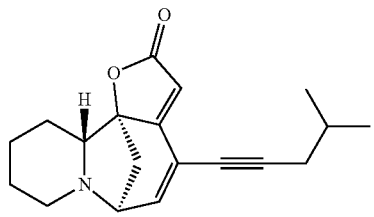
INVS-MG-110B
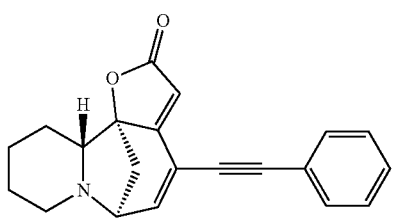
INVS-MG-111B
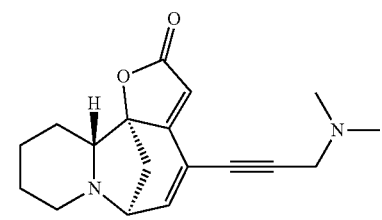
INVS-MG-113A
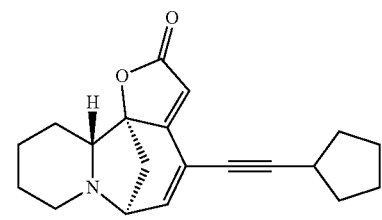
INVS-MG-117B
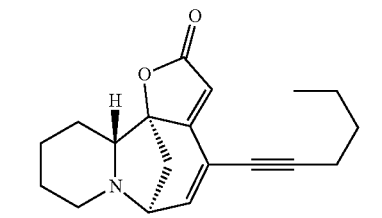
INVS-MG-118B
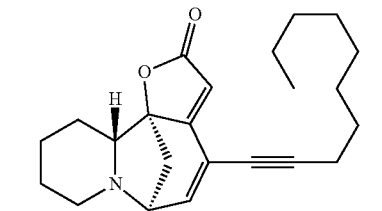
INVS-MG-120A
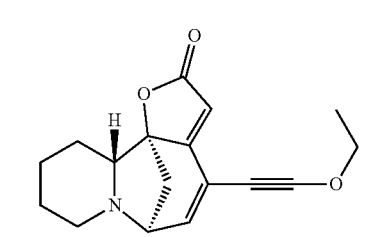
INVS-MG-121A
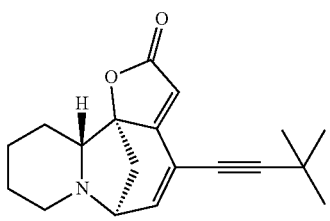
INVS-MG-123B
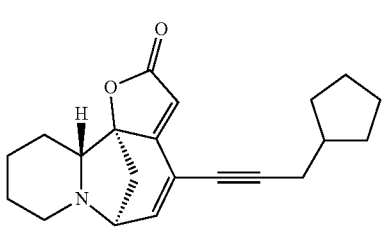
INVS-MG-124A
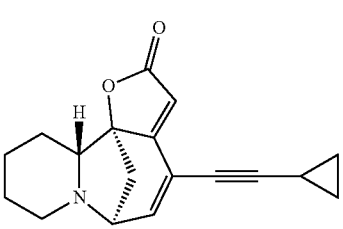
INVS-MG-125A
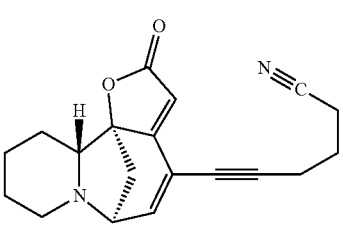
INVS-MG-131A
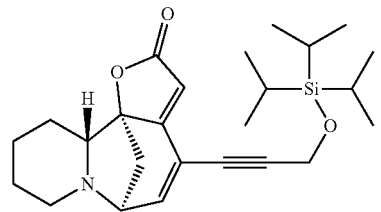
INVS-MG-132A
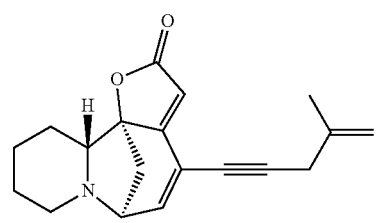

-continued
INVS-MG-134C
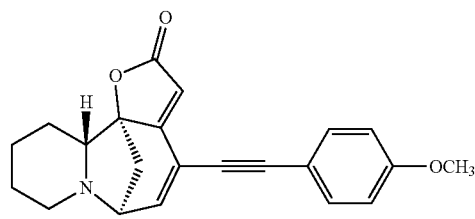
INVS-MG-138B
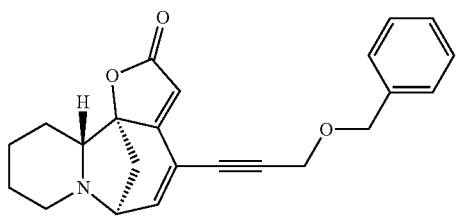
INVS-MG-135B
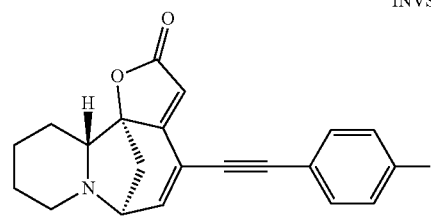
INVS-MG-145A
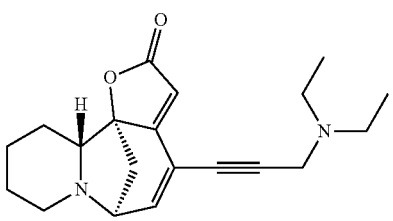
INVS-MG-136B
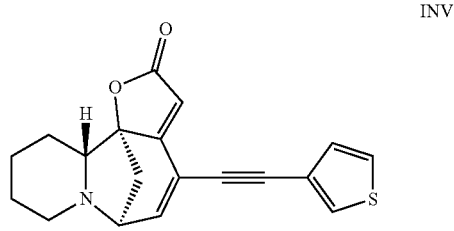
INVS-MG-146B
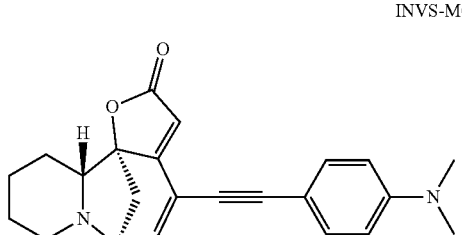
INVS-MG-133B
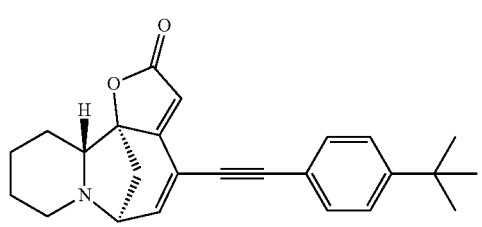
INVS-MG-150B
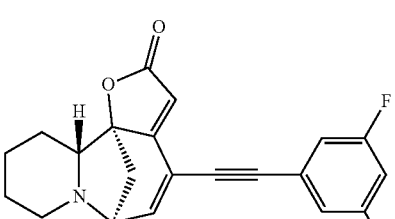
INVS-MG-133B
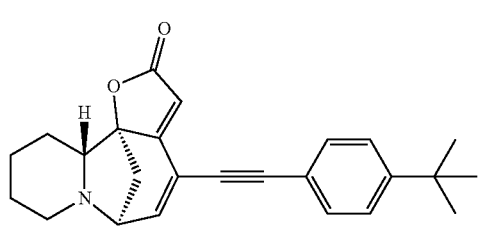
INVS-MG-151B
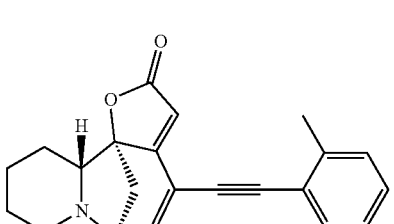
INVS-MG-137B
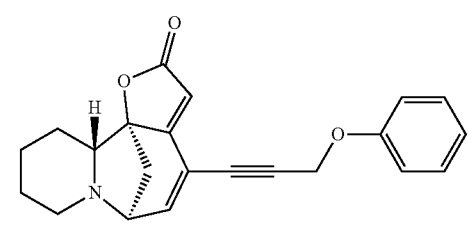
INVS-MG-152A
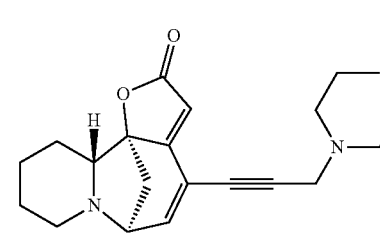

INVS-MG-157B
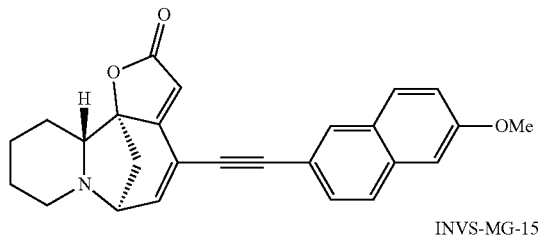
INVS-MG-158B
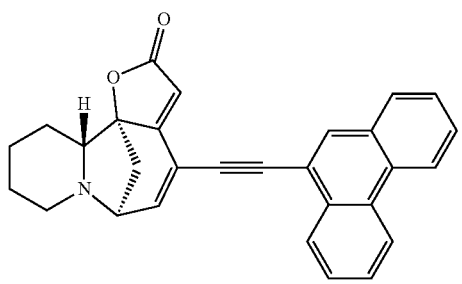
INVS-MG-159A
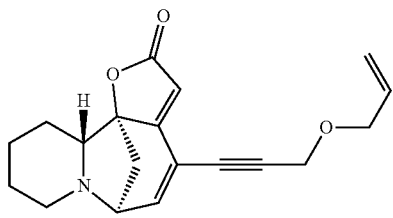
INVS-MG-160B
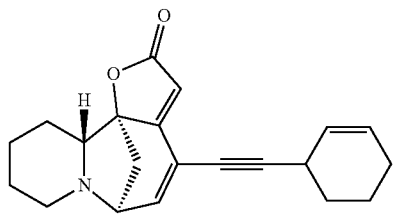
INVS-MG-161B
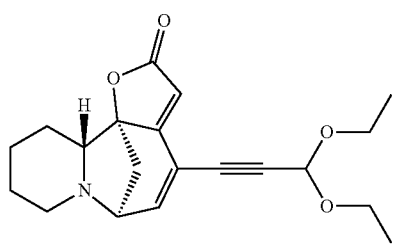
INVS-MG-162B
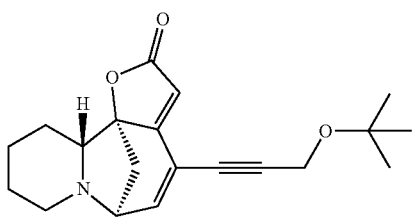
INVS-MG-164B
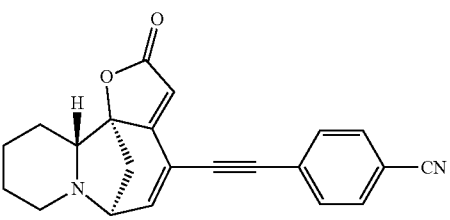
INVS-MG-165B
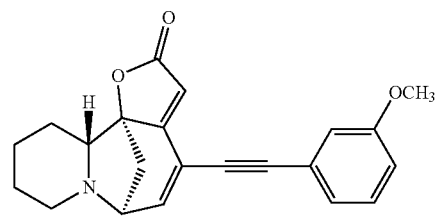
INVS-MG-166B
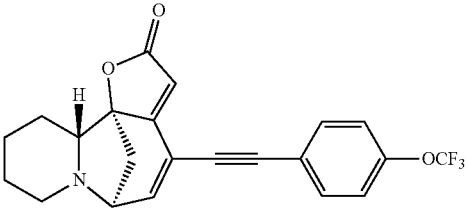
INVS-MG-167B
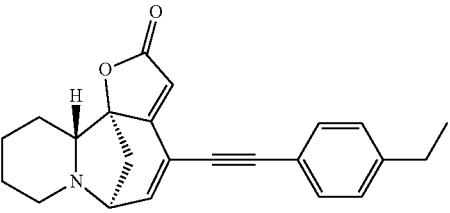
INVS-MG-168B
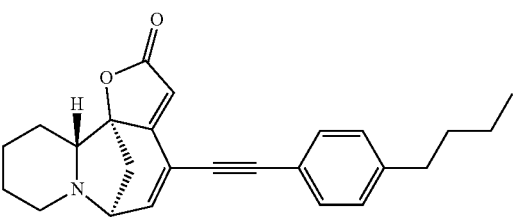
INVS-MG-169B
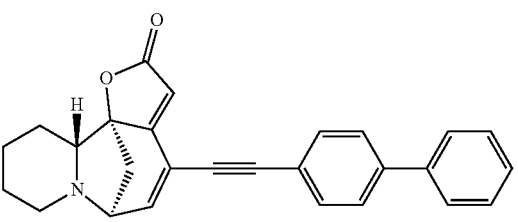

153
-continued
INVS-MG-170B
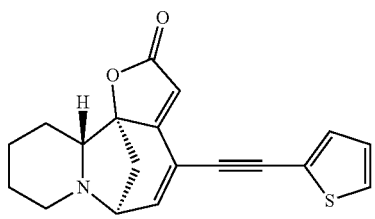
INVS-MG-175A
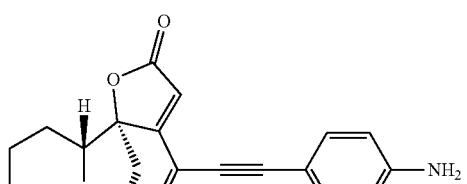
INVS-MG-193B
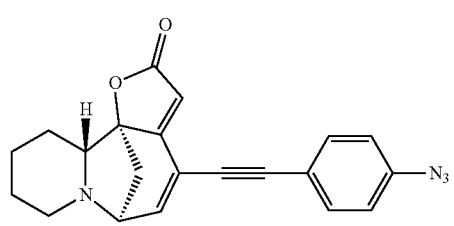
INVS-MG-70
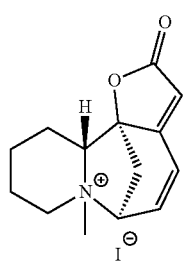
INVS-MG-72
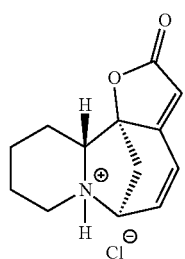
INVS-MG-83
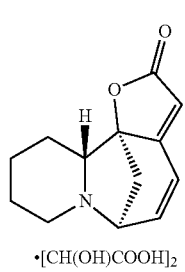
·[CH(OH)COOH]₂
154
-continued
INVS-MG-71
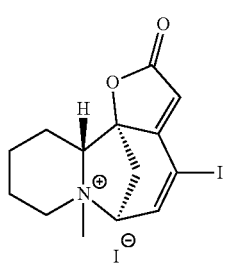
INVS-MG-73
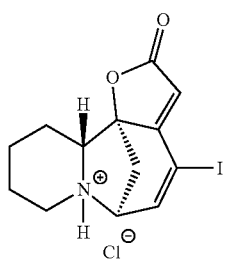
INVS-MG-84
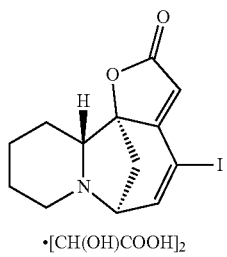
·[CH(OH)COOH]₂
INVS-MG-111-IV
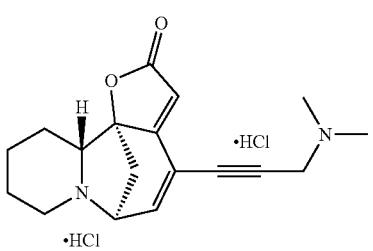
INVS-MG-125-III
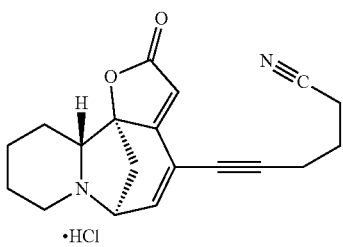
·HCl
INVS-MG-157-III
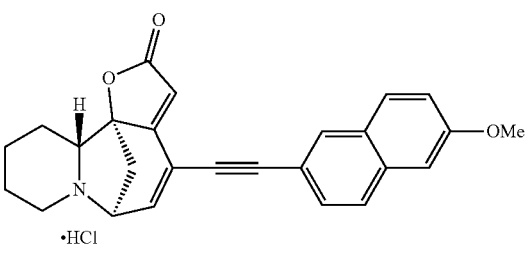
·HCl

155

-continued

INVS-MG-158-III ·HCl

INVS-MG-169-III ·HCl

INVS-MG-170-III ·HCl

INVS-MG-146-III ·2HCl

INVS-MG-152-III ·2HCl

INVS-MG-175-V ·2HCl

156

-continued

INVS-MG-193-III ·HCl

INV-SZ-113-2

INV-SZ-114-1

INV-SZ-115-1

INV-SZ-116-2

INV-SZ-117-2
INV-SZ-118-2
INV-SZ-120-1
INV-SZ-121-1
INV-SZ-122-1
INV-SZ-123-2
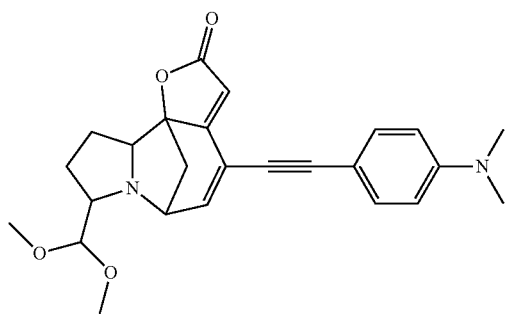
INV-SZ-123-3
INV-SZ-125-1
INV-SZ-125-2
INV-SZ-125-3
INV-SZ-127-1
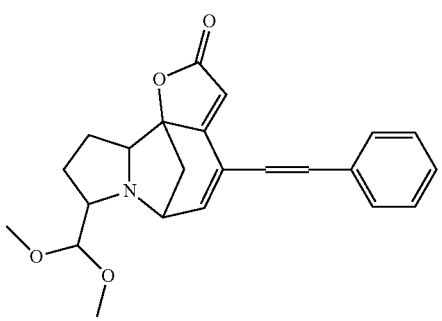
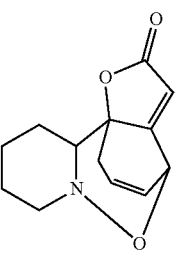
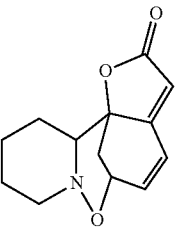
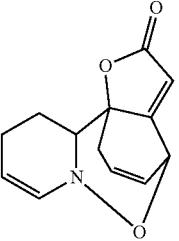
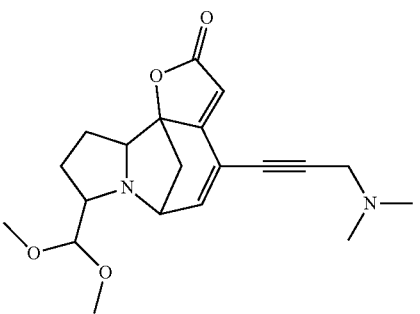
and -continued

INV-SZ-129-1

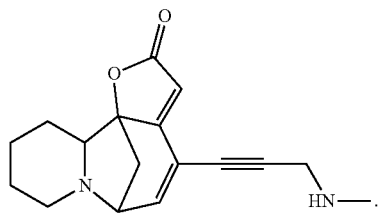

3. The method of claim 1, wherein the securinine analog has a reduced γ,δ double bond.

4. The method of claim 1, wherein the securinine or norsecurinine analog is selected from the group consisting of

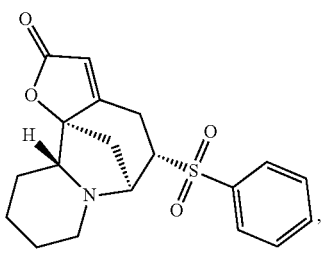,

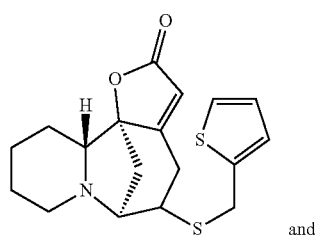 and

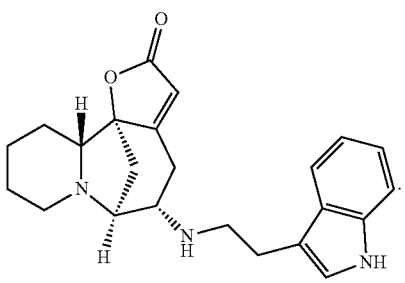.

5. The method of claim 1, wherein the securinine or norsecurinine analog has a non-reduced γ,δ double bond.

6. The method of claim 1, wherein the myeloperoxidase molecule is located in a subject.

7. The method of claim 4, wherein the MPO molecule is located within a cell.

8. The method of claim 1, wherein the MPO molecule is proximal to an exterior of a cell.

9. A method of treating cellular damage to a cell by a myeloperoxidase (MPO) enzyme comprising contacting the MPO enzyme with a securinine or norsecurinine analog, wherein the securinine or norsecurinine analog comprises a structure selected from the group consisting of:

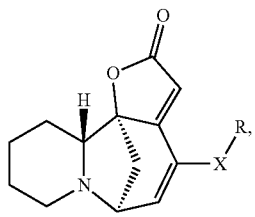

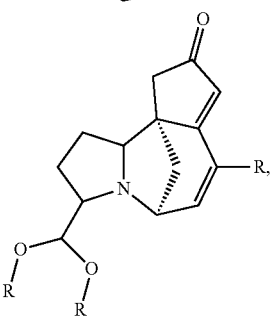

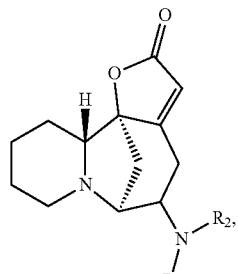

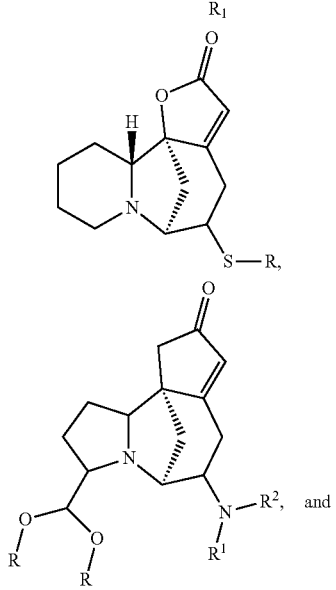, and

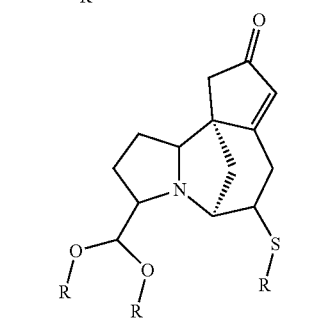

wherein X is a C, C—C, C=C or C≡C and R, $R_1$ or $R_2$ is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof.

\* \* \* \* \*

UNITED STATES PATENT AND TRADEMARK OFFICE
CERTIFICATE OF CORRECTION

PATENT NO. : 10,149,838 B2
APPLICATION NO. : 15/026818
DATED : December 11, 2018
INVENTOR(S) : Mahesh K. Gundluru et al.

Page 1 of 4

It is certified that error appears in the above-identified patent and that said Letters Patent is hereby corrected as shown below:

In the Specification

Column 3, Line 10, please replace

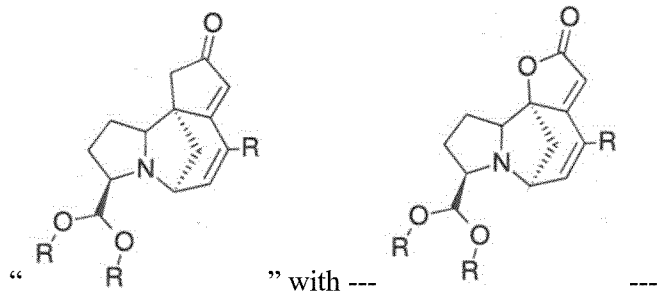

" with ---    ---

Column 3, Line 42, please replace

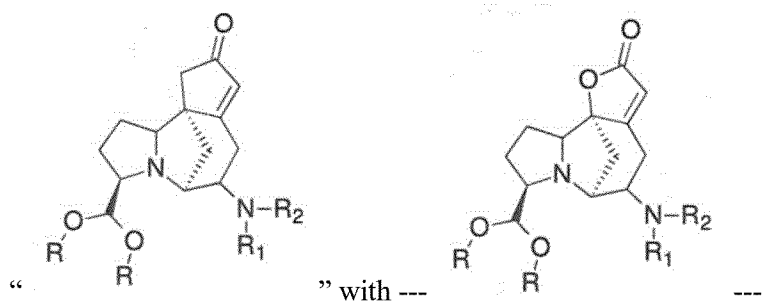

" with ---    ---

Signed and Sealed this
Twenty-sixth Day of March, 2019

Andrei Iancu
*Director of the United States Patent and Trademark Office*

CERTIFICATE OF CORRECTION (continued)
U.S. Pat. No. 10,149,838 B2

Column 3, Line 54, please replace

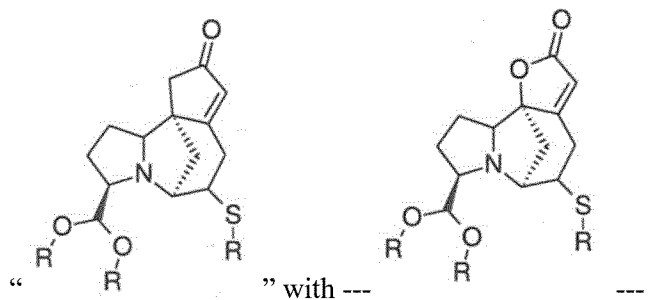

" with ---  ---

Column 7, Line 46, please replace

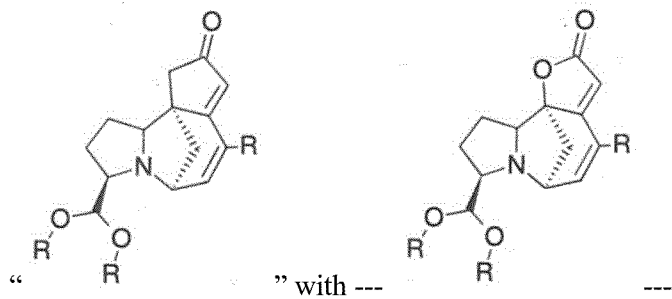

" with ---  ---

Column 26, Line 55, please replace

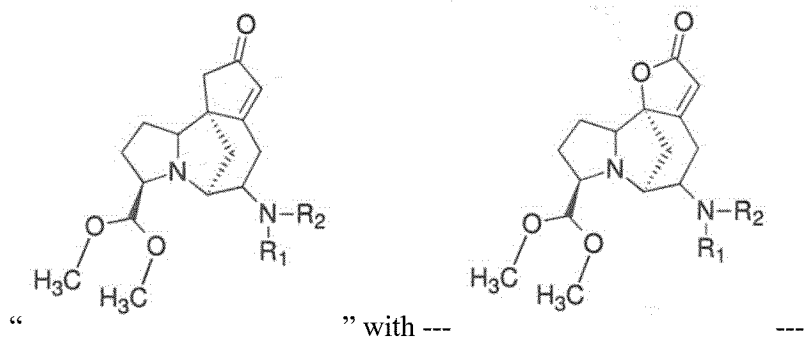

" with ---  ---

Column 27, Line 1, please replace

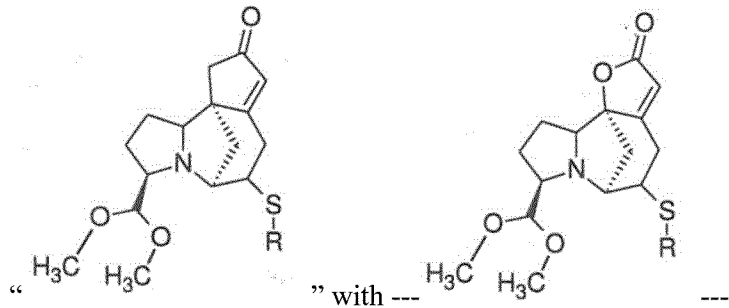

" with ---  ---

CERTIFICATE OF CORRECTION (continued)
U.S. Pat. No. 10,149,838 B2

In the Claims

Claim 1, Column 144, Line 44, please replace

" 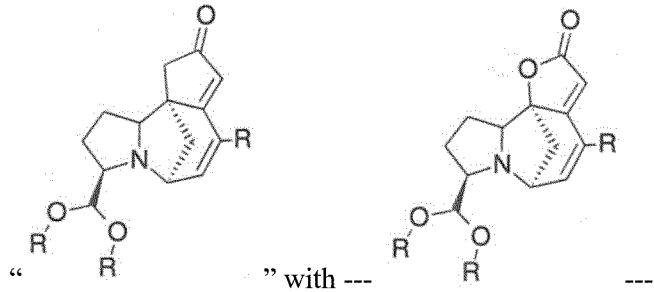 " with --- ---

Column 145, Line 11, please replace

" 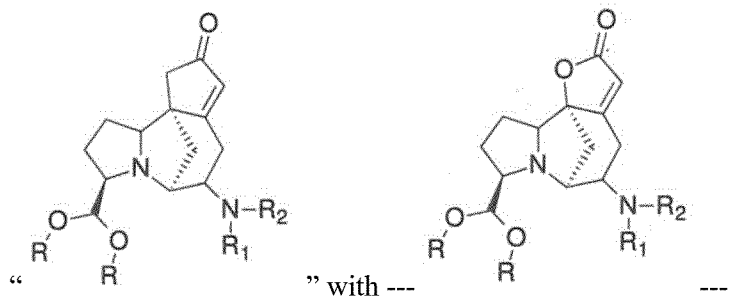 " with --- ---

Column 145, Line 22, please replace

" 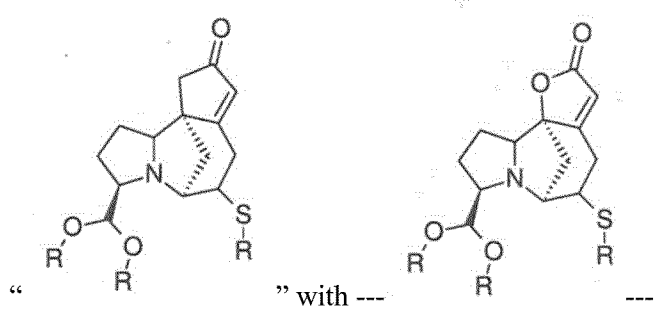 " with --- ---

Claim 9, Column 160, Line 10, please replace

" 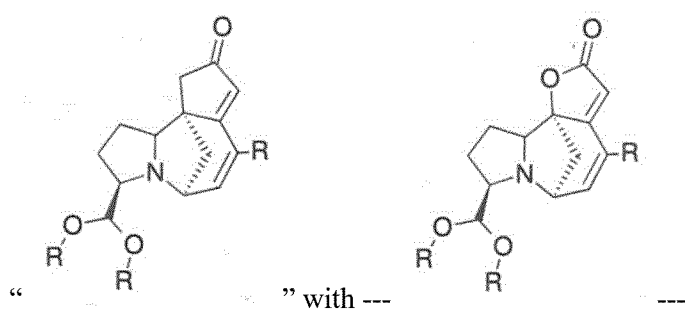 " with --- ---

CERTIFICATE OF CORRECTION (continued)
U.S. Pat. No. 10,149,838 B2

Page 4 of 4

Column 160, Line 42, please replace

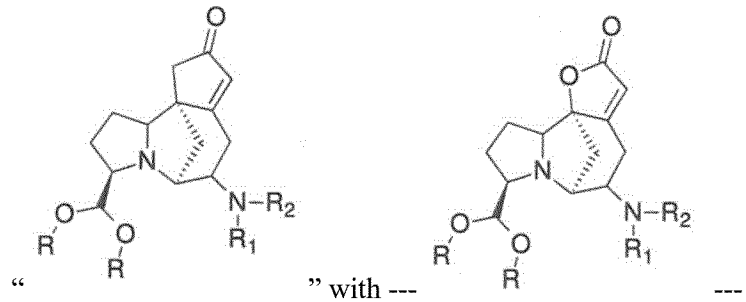 " with ---  ---

Column 160, Line 53, please replace

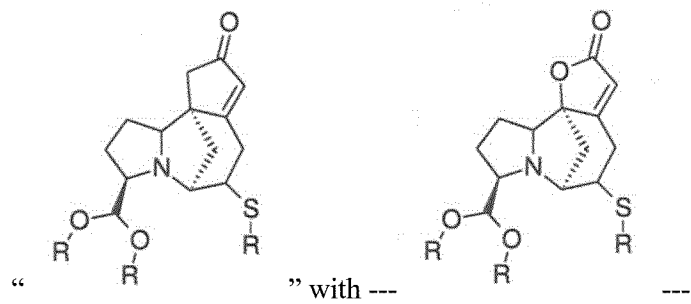 " with ---  ---